US008354254B2

(12) United States Patent
Suzuki et al.

(10) Patent No.: US 8,354,254 B2
(45) Date of Patent: Jan. 15, 2013

(54) METHOD FOR PRODUCING AN L-AMINO ACID

(75) Inventors: Shigeo Suzuki, Kanagawa (JP);
 Yoshihiro Usuda, Kanagawa (JP);
 Shuhei Hashiro, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 3 days.

(21) Appl. No.: 12/842,355

(22) Filed: Jul. 23, 2010

(65) Prior Publication Data

US 2011/0014663 A1 Jan. 20, 2011

Related U.S. Application Data

(63) Continuation of application No. PCT/JP2009/051104, filed on Jan. 23, 2009.

(30) Foreign Application Priority Data

Jan. 23, 2008 (JP) .................................. 2008-012553
May 23, 2008 (JP) .................................. 2008-135265

(51) Int. Cl.
 *C12P 13/04* (2006.01)

(52) U.S. Cl. .................... 435/106; 435/110; 435/112

(58) Field of Classification Search .................. 435/110, 435/106, 112
See application file for complete search history.

(56) References Cited

U.S. PATENT DOCUMENTS

| 5,578,472 | A | 11/1996 | Ueda et al. |
| 5,939,307 | A | 8/1999 | Wang et al. |
| 6,040,160 | A | 3/2000 | Kojima et al. |
| 6,221,636 | B1 | 4/2001 | Hayakawa et al. |
| 6,911,332 | B2 | 6/2005 | Usuda et al. |
| 7,026,149 | B2 | 4/2006 | Usuda et al. |
| 7,029,893 | B2 | 4/2006 | Usuda et al. |
| 7,060,475 | B2 | 6/2006 | Usuda et al. |
| 7,135,308 | B1 | 11/2006 | Bush et al. |
| 7,192,748 | B2 | 3/2007 | Usuda et al. |
| 7,220,570 | B2 | 5/2007 | Usuda et al. |
| 7,306,933 | B2 | 12/2007 | Dien et al. |
| 7,468,262 | B2 | 12/2008 | Usuda et al. |
| 7,695,946 | B2 | 4/2010 | Usuda et al. |
| 7,696,315 | B2 | 4/2010 | Usuda et al. |
| 2002/0110876 | A1 | 8/2002 | Miyata et al. |
| 2005/0233308 | A1 | 10/2005 | Nishio et al. |
| 2006/0135308 | A1 | 6/2006 | Abraham |
| 2007/0082399 | A1* | 4/2007 | Egorova-Zachernyuk ... 435/404 |
| 2007/0202582 | A1 | 8/2007 | Bush et al. |
| 2009/0068712 | A1 | 3/2009 | Terashita et al. |
| 2009/0093029 | A1 | 4/2009 | Usuda et al. |
| 2009/0148915 | A1 | 6/2009 | Van Dien et al. |
| 2009/0203090 | A1 | 8/2009 | Ptitsyn et al. |
| 2009/0239269 | A1 | 9/2009 | Tajima et al. |
| 2009/0246835 | A1 | 10/2009 | Iwatani et al. |
| 2009/0291478 | A1 | 11/2009 | Usuda et al. |
| 2010/0047878 | A1 | 2/2010 | Nagai et al. |
| 2010/0062497 | A1 | 3/2010 | Shiraga et al. |
| 2010/0081180 | A1 | 4/2010 | Fukui et al. |
| 2010/0093044 | A1 | 4/2010 | Terashita et al. |
| 2010/0112647 | A1 | 5/2010 | Hara et al. |

FOREIGN PATENT DOCUMENTS

| JP | 05-227977 | 9/1993 |
| JP | 05-304969 | 11/1993 |
| JP | 07-087983 | 4/1995 |
| JP | 10-165180 | 6/1998 |
| JP | 11-192088 | 7/1999 |
| JP | 2000-253879 | 9/2000 |
| JP | 2001-057896 | 3/2001 |
| WO | WO98/04715 | 2/1998 |
| WO | WO2007/100009 | 9/2007 |
| WO | WO2007/101172 | 9/2007 |
| WO | WO2008/002053 | 1/2008 |
| WO | WO2011/013707 | 2/2011 |

OTHER PUBLICATIONS

Chisti, Y., "Biodiesel from microalgae," Biotechnol. Adv. 2007;25:294-306.
International Search Report for PCT Patent App. No. PCT/JP2009/051104 (Mar. 3, 2009).
Brenner, D. J. and Farmer III, J. J., Family I., 2005, pp. 587-669, In: D. J. Brenner, N.R. Krieg and J. T. Staley, Editors, Bergey's Manual of Systemic Bacteriology, Volume Two: The Proteobacteria Part B: The Gammaproteobacteria, Springer, New York, US.
Clark, D. P. and Cronan Jr., J.E., 1996, pp. 343-357, In F.D. Neidhardt (ed.), *Escherichia coli* and *Salmonella* Cellular and Molecular Biology/Second Edition, American Society for Microbiology Press, Washington, DC, US.
Lin, E. C. C., 1996, pp. 307-342, In F. D. Neidhardt (ed.), *Escherichia coli* and *Salmonella* Cellular and Molecular Biology/Second Edition, American Society for Microbiology Press, Washington, DC, US.
Matsumoto, M., et al., "Saccharification of Marine Microalgae Using Marine Bacteria for Ethanol Production," Appl. Biochem. Biotechnol. 2003;105-108:247-254.
Vorum, H., et al., "Solubility of long-chain fatty acids in phosphate buffer at pH7.4," Biochimica et Biophysica Acta 1992;1126:135-142.
Supplementary European Search Report for EP Patent App. No. 09704195.8 (Jun. 13, 2012), plus duplicate of pp. 1 and 5 of the Report showing deficiencies as summarized in Response to Office Action.
Database WPI, Week 201115, AN 2011-B35904, Thomson Scientific, London, XP-002677099 (printed Jun. 6, 2012).
Fay, J. P., et al., "The Inhibitory Action of Fatty Acids on the Growth of *Escherichia coli*," J. Gen. Microbiol. 1975;92:233-240.
Shub, T. A., et al., "Use of *Chlorella* Hydrolysate in Culture Media and Pharmaceutical Microbiology," Pharm. Chem. J. 1994;28(7):513-515.
U.S. Appl. No. 12/749,932, filed Mar. 30, 2010, Nagai et al.
Fay, J. P., et al., "The Inhibitory Action of Fatty Acids on the Growth of *Escherichia coli*," J. Gen. Microbiol. 1975;91:233-240.

* cited by examiner

*Primary Examiner* — Tekchand Saidha

(74) *Attorney, Agent, or Firm* — Shelly Guest Cermak; Cermak Nakajima LLP

(57) ABSTRACT

An L-amino acid is produced by culturing a bacterium having an L-amino acid-producing ability in a medium containing a processed product of a microalga which promotes production and accumulation of the L-amino acid by the bacterium. The process product is produced by disrupting the culture of the microalga, and/or extracting the culture of the microalga, or fractionating the culture of the microalga or the disrupted culture. The processed product contains a mixture of organic substances produced by the microalga, a hydrolysate of the disrupted microalga culture, and/or an extract or fractionation product of the microalga culture. The processed product can also contain a saccarification product of starch or a hydrolysate of fats and oils. The bacterium is cultured to produce and accumulate the L-amino acid in culture, and the L-amino acid is collected from the culture.

32 Claims, No Drawings

METHOD FOR PRODUCING AN L-AMINO ACID

This application is a continuation under 35 U.S.C. §120 of PCT Patent Application No. PCT/JP2009/051104, filed Jan. 23, 2009, which claims priority under 35 U.S.C. §119 to Japanese Patent Application Nos. 2008-012553, filed on Jan. 23, 2008, and 2008-135265, filed on May 23, 2008, which are incorporated in their entireties by reference. The Sequence Listing in electronic format filed herewith is also hereby incorporated by reference in its entirety (File Name: 2010-07-23T_US-440_Seq_List; File Size: 73 KB; Date Created: Jul. 23, 2010).

BACKGROUND OF THE INVENTION

1. Field of the Invention

The present invention relates to a method for producing an L-amino acid using a microorganism. L-amino acids are used in various applications, such as for use in seasonings, food additives, feed additives, chemicals, and drugs.

2. Brief Description of the Related Art

L-amino acids such as L-threonine and L-lysine are industrially produced by fermentation of bacteria such as *Escherichia*. Bacterial strains isolated from nature, artificial mutants, and recombinants in which L-amino acid biosynthetic enzymes are enhanced by gene recombination, or the like, are used. Examples of the methods for producing L-threonine include, for example, the methods described in Japanese Patent Laid-open (Kokai) No. 5-304969, International Publication WO98/04715, Japanese Patent Laid-open No. 05-227977, and U.S. Patent Published Application No. 2002/0110876. Examples of the methods for producing L-lysine include, for example, the methods described in Japanese Patent Laid-open No. 10-165180, Japanese Patent Laid-open No. 11-192088, Japanese Patent Laid-open No. 2000-253879, and Japanese Patent Laid-open No. 2001-057896.

In the industrial production of L-amino acids by fermentation, saccharides, such as glucose, fructose, sucrose, blackstrap molasses, starch hydrolysate, and so forth, are used as carbon sources. Other carbon sources that are frequently used in methods for producing an L-amino acid by fermentation include saccharification products of starches derived from higher plants such as corn and cassava. These have a low moisture content and high starch content, and therefore, it is easy to industrially obtain starches from them. On the other hand, although starches in microalgae are usually present in an amount per dry weight unit comparable to that of corn or cassava, the dry weight of the algae per weight unit of culture medium does not approach 1%. The process of separating alga bodies, dehydrating them, disrupting the cells, extracting starches, and purifying the starches is complicated and difficult. Although ethanol fermentation using starches of microalgae is described in U.S. Patent Published Application No. 2006/135308, U.S. Patent Published Application No. 2007/0202582 and Matsumoto, M. et al., 2003, Appl. Biochem. Biotechnol., 105-108:247-254, the results of the ethanol fermentation are not described. Furthermore, examples using saccharified starches of microalgae for amino acid production has not been previously reported.

It is known that *Escherichia coli*, which is a typical amino acid-producing bacterium, can grow using glycerol as the sole carbon source (Lin, E. C. C., 1996, pp. 307-342, In F. D. Neidhardt (ed.), *Escherichia coli* and *Salmonella* Cellular and Molecular Biology/Second Edition, American Society for Microbiology Press, Washington, D.C.), and can grow using long chain fatty acids having 12 or more carbon atoms as the sole carbon source (Clark, D. P. and Cronan Jr., J. E., 1996, pp. 343-357, In F. D. Neidhardt (ed.), *Escherichia coli* and *Salmonella* Cellular and Molecular Biology/Second Edition, American Society for Microbiology Press, Washington, D.C.). Therefore, *Escherichia coli* can assimilate both long chain fatty acids and glycerol, both of which are hydrolysis products of fats and oils. However, *Escherichia coli* does not have lipase activity, and therefore, it cannot directly assimilate fats and oils (Brenner, D. J. and Farmer III J. J. Family I., 2005, pp. 587-669, In: D. J. Brenner, N. R. Krieg and J. T. Staley, Editors, Bergey's Manual of Systematic Bacteriology, Volume Two: The Proteobacteria Part B: The Gammaproteobacteria, Springer, N.Y.). Furthermore, it is also known that the solubility of long chain fatty acids is generally extremely low, and solubility measurements are described in Vorum, H. et al., 1992, Biochimica et Biophysica Acta, 1126:135-142. However, solubility of lauric acid is not lower than 0.1 g/L, solubility of oleic acid is not higher than 0.0003 g/L, and solubility of palmitic acid is not higher than 0.00000003 g/L. Therefore, it is difficult to simultaneously assimilate highly water-soluble glycerol and aliphatic acids. L-amino acid production based on direct fermentation utilizing an hydrolysate of fats and oils, which is a mixture of long chain fatty acids and glycerol, as the carbon source has not been previously reported.

Soybean and *Elaeis guineensis* (oil palm) are oil plants generally used for production of edible oils, beans, or fruits thereof. They typically contain about 20% of fats and oils. Microalgae is also know to produce fats and oils, and the amounts produced per area far exceeds that obtained with the oil plants, as reported in Chisti Y., 2007, Biotechnol. Adv., 25:294-306. However, the process of separating algae and alga bodies, dehydrating them, disrupting the cells, extracting fats and oils, and purifying them is complicated and difficult, as in the case of starches. Therefore, L-amino acid production based on direct fermentation utilizing fats and oils from algae has also not been previously reported.

SUMMARY OF THE INVENTION

An aspect of the present invention is to provide a more efficient method for producing an L-amino acid, especially producing an L-amino acid at a lower cost by using a carbon source derived from microalgae, as compared with conventional methods for producing an L-amino acid by fermentation using microorganisms, which mainly uses saccharides derived from higher plants as the carbon source.

It has been found that L-amino acids can be efficiently produced by culturing a bacterium having an L-amino acid-producing ability in a medium containing, as a carbon source, a saccharification product obtained by subjecting starches from microalgae to a hydrolysis treatment with an enzyme, a disruption product of alga bodies of microalgae, an extract thereof containing fats and oils, or a hydrolysate obtained by hydrolyzing a fractionation product of the extract, which are not completely purified.

It is an aspect of the present invention to provide a method for producing an L-amino acid, comprising:

(a) culturing a bacterium having the ability to produce an L-amino acid in a medium comprising a processed product of a microalga and, (b) collecting the L-amino acid from the medium or the bacterium;

wherein the processed product increases production and accumulation of the L-amino acid by the bacterium.

It is another aspect of the present invention to provide the method as described above, wherein the processed product is selected from the group consisting of (1) a disruption product of a culture of the microalga, (2) an extract or a fractionation product of a disruption product of a culture of the microalga comprising a mixture of organic substances, (3) a hydrolysate of a disruption product of a culture of the microalga, (4) a hydrolysate of an extract or a fractionation product of a culture of the microalga comprising a mixture of organic substances, and (5) combinations thereof.

It is another aspect of the present invention to provide the method as described above, wherein the processed product is selected from the group consisting of:

(1) a saccharification product of a disruption product of alga bodies of the microalga, and (2) a saccharification product of an extract or a fractionation product of a disruption product of alga bodies of the microalga, wherein the extract or fractionation product comprises starch, (3) combinations thereof.

It is another aspect of the present invention to provide the method as described above, wherein the saccharification product is obtained from the reaction of a disruption product of alga bodies of a microalga or a fractionation product thereof comprising starch with an amylase.

It is another aspect of the present invention to provide the method as described above, wherein the amylase is glucoamylase.

It is another aspect of the present invention to provide the method as described above, wherein the processed product is selected from the group consisting of:

(1) a hydrolysate of a disruption product of alga bodies of the microalga, wherein the disruption product comprises fats and oils, (2) a hydrolysate of an extract or a fractionation product of a disruption product of alga bodies of the microalga, wherein the extract or the fractionation product comprises fats and oils, and (3) combinations thereof.

It is another aspect of the present invention to provide the method as described above, wherein the hydrolysate is obtained from the reaction of a disruption product of alga bodies of a microalga or a fractionation product thereof comprising fats and oils with a lipase.

It is another aspect of the present invention to provide the method as described above, wherein the hydrolysate is subjected to an emulsification treatment.

It is another aspect of the present invention to provide the method as described above, wherein the processed product of a microalga is obtained by disrupting the microalga at a high temperature.

It is another aspect of the present invention to provide the method as described above, wherein the high temperature is 100° C. or higher.

It is another aspect of the present invention to provide the method as described above, wherein the microalga belongs to the phylum Chlorophyta or Heterokontophyta.

It is another aspect of the present invention to provide the method as described above, wherein the microalga belongs to the class Chlorophyceae, Trebouxiophyceae, or Bacillariophyceae.

It is another aspect of the present invention to provide the method as described above, wherein the microalga belongs to the class Chlorophyceae.

It is another aspect of the present invention to provide the method as described above, wherein the bacterium belongs to the family Enterobacteriaceae or coryneform bacterium.

It is another aspect of the present invention to provide the method as described above, wherein the bacterium is *Escherichia coli*.

It is another aspect of the present invention to provide the method as described above, wherein the L-amino acid is selected from the group consisting of L-lysine, L-threonine, L-glutamic acid, and combinations thereof.

It is another aspect of the present invention to provide the method as described above, wherein the L-amino acid is L-lysine; and the activity is increased of an enzyme selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl diaminopimelate deacylase, and combinations thereof; and/or the activity of lysine decarboxylase is attenuated.

It is another aspect of the present invention to provide the method as described above, wherein the L-amino acid is L-threonine; and the activity is increased of an enzyme selected from the group consisting of aspartate semialdehyde dehydrogenase, and aspartokinase I encoded by the thr operon, homoserine kinase, aspartate aminotransferase, threonine synthase, and combinations thereof.

It is another aspect of the present invention to provide the method as described above, wherein the L-amino acid is L-glutamic acid; and the activity is increased of an enzyme selected from the group consisting of glutamate dehydrogenase, citrate synthase, phosphoenolpyruvate carboxylase methyl citrate synthase, and combinations thereof; and/or the activity of $\alpha$-ketoglutarate dehydrogenase is attenuated.

It is another aspect of the present invention to provide the method as described above, wherein the processed product acts as a carbon source in the medium.

It is another aspect of the present invention to provide a method of producing an L-amino acid, which comprises:

(a) culturing a microalga in a medium, resulting in a culture product, (b) processing the culture produce by a method selected from the group consisting of disruption, extraction, fractionation, hydrolysis, and combinations thereof, resulting in a processed product of the microalga, (c) culturing a bacterium which is able to produce the L-amino acid in a second medium comprising the processed product of the microalga, and (d) collecting the L-amino acid from the second medium or the bacterium;

wherein the processed product of the microalga increases production and accumulation of the L-amino acid.

It is another aspect of the present invention to provide the method as described above, wherein the processed product is selected from the group consisting of (1) a disruption product of the culture product, (2) an extract or a fractionation product of the disruption product of the culture product, comprising a mixture of organic substances derived from the microalga, (3) a hydrolysate of the disruption product of the culture product, (4) a hydrolysate of the extract or the fractionation product of the disruption product of the culture product, and (5) combinations thereof.

It is another aspect of the present invention to provide the method as described above, wherein the disruption is performed by a method selected from the group consisting of a high temperature treatment, an organic solvent treatment, a boiling treatment, a strong alkali treatment, and combinations thereof.

It is another aspect of the present invention to provide the method as described above, wherein the step of processing the culture product comprises starch the production of starch, and the processed product is subjected to further hydrolyzation to saccharify it.

It is another aspect of the present invention to provide the method as described above, wherein the step of further hydrolyzation comprises reacting the processed product with an amylase.

It is another aspect of the present invention to provide the method as described above, wherein the amylase is glucoamylase.

It is another aspect of the present invention to provide the method as described above, wherein step of processing the culture product uct comprises the production of fats and oils, and the processed product is subjected to further hydrolyzation.

It is another aspect of the present invention to provide the method as described above, wherein the step of further hydrolyzation comprises reacting the processed product with a lipase.

It is another aspect of the present invention to provide the method as described above, wherein the processed product which is further hydrolyzed is subjected to an emulsification treatment.

It is another aspect of the present invention to provide the method as described above, wherein the microalga belongs to the phylum Chlorophyta or Heterokontophyta.

It is another aspect of the present invention to provide the method as described above, wherein the microalga belongs to the class Chlorophyceae, Trebouxiophyceae, or Bacillariophyceae.

It is another aspect of the present invention to provide the method as described above, wherein the microalga belongs to the class Chlorophyceae.

It is another aspect of the present invention to provide the method as described above, wherein the bacterium belongs to the family Enterobacteriaceae or coryneform bacterium.

It is another aspect of the present invention to provide the method as described above, wherein the bacterium is *Escherichia coli*.

DESCRIPTION OF THE PREFERRED EMBODIMENTS

<1> Microalgae and Culture Method Therefor

Any type of algae can be used. Microalgae which produce starches and/or fats and oils in alga bodies is an example.

The term "algae" refers to organisms which undergo the type of photosynthesis which results in the generation of oxygen, except for Bryophyta, Pteridophyta and Spermatophyta, which are also referred to as algae, but live mainly on the ground. Algae can include various unicellular organisms and multicellular organisms such as cyanobacteria (blue-green algae), which are prokaryotes, as well as eukaryotes, such as those classified into the phylum Glaucophyta, Rhodophyta (red algae), Chlorophyta, Cryptophyta (crypt algae), Haptophyta (haptophytes), Heterokontophyta, Dinophyta (dinoflagellates), Euglenophyta, or Chlorarachniophyta. Microalgae can refer to microscopic algae, and can include marine algae, which can be multicellular organisms (Biodiversity Series (3) Diversity and Pedigree of Algae, edited by Mitsuo Chihara, Shokabo Publishing Co., Ltd. (1999)).

Many plants, including algae, produce starches as storage polysaccharides (Ball, S. G. and Morell, M. K., 2003, Annual Review of Plant Biology, 54:207-233). Many algae which produce starches are known, and include those of the class Prasinophyceae, Chlorophyceae, Trebouxiophyceae, Ulvophyceae, Charophyceae, or the like, which all belong to the phylum Chlorophyta. Among these, algae belonging to the class Chlorophyceae or Trebouxiophyceae have been well studied. Examples of algae belonging to the class Chlorophyceae include those of the genus *Chlamydomonas*, and examples of algae belonging to the class Trebouxiophyceae include those of the genus *Chlorella*. Specifically, examples of algae belonging to the genus *Chlamydomonas* include *Chlamydomonas reinhardtii* (Ball, S. G., 1998, The Molecular Biology of Chloroplasts and Mitochondria in *Chlamydomonas*, pp. 549-567, Rochaix J.-D., Goldschmidt-Clermont M., and Merchant S. (Eds), Kluwer Academic Publishers), and examples of algae belonging to the genus *Chlorella* include *Chlorella kessleri* (formerly *Chlorella vulgaris*, Izumo A. et al, 2007, Plant Science, 172:1138-1147). More specifically, examples of *Chlamydomonas reinhardtii* include the *Chlamydomonas reinhardtii* CC125 strain, and examples of *Chlorella kessleri* include the *Chlorella kessleri* 11h strain. These strains are stored at, for example, The University of Texas at Austin, The Culture Collection of Algae (UTEX) (1 University Station A6700, Austin, Tex. 78712-0183, USA) with accession numbers of UTEX 2244 and UTEX 263, respectively, and can be obtained from UTEX. The *Chlorella kessleri* 11h strain had been stored at the independent administrative agency, the IAM Culture Collection, Institute of Molecular and Cellular Biosciences, The University of Tokyo with a storage number of C-531, but was then transferred to the Microbial Culture Collection at the National Institute for Environmental Studies (NIES). Furthermore, this strain is stored at the American Type Culture Collection (ATCC, P.O. Box 1549, Manassas, Va. 20108, 1, United States of America) under an accession number of ATCC 11468, and can also be obtained from ATCC.

It is further known that microalgae can include microalgae which accumulate fats and oils as storage substances (Chisti Y., 2007, Biotechnol. Adv., 25:294-306). As such algae, those belonging to the phylum Chlorophyta or Heterokontophyta are well known. Examples of the algae belonging to the phylum Chlorophyta include those belonging to the class Chlorophyceae, and examples of algae belonging to the class Chlorophyceae include *Neochloris oleoabundans* (Tornabene, T. G. et al., 1983, Enzyme and Microb. Technol., 5:435-440), *Nannochloris* sp. (Takagi, M. et al., 2000, Appl. Microbiol. Biotechnol., 54:112-117) and so forth. The classes Chrysophyceae, Dictyochophyceae, Pelagophyceae, Rhaphidophyceae, Bacillariophyceae, Phaeophyceae, Xanthophyceae, and Eustigmatophyceae are classified in the phylum Heterokontophyta. Examples of frequently used algae belonging to the class Bacillariophyceae include *Thalassiosira pseudonana* (Tonon, T. et al., 2002, Phytochemistry, 61:15-24). Specific examples of *Neochloris oleoabundans* include the *Neochloris oleoabundans* UTEX 1185 strain, specific examples of *Nannochloris* sp. include the *Nannochloris* sp. UTEX LB 1999 strain, and specific examples of *Thalassiosira pseudonana* include the *Thalassiosira pseudonana* UTEX LB FD2 strain. These strains can be obtained from the University of Texas at Austin, The Culture Collection of Algae (UTEX), 1 University Station A6700, Austin, Tex. 78712-0183, USA.

There is much information about culturing microalgae, and those of the genus *Chlorella* or *Arthrospira* (*Spirulina*), *Dunaliella salina*, and so forth are industrially cultured on a large scale (Spolaore, P. et al., 2006, J. Biosci. Bioeng., 101: 87-96). For *Chlamydomonas reinhardtii*, for example, the 0.3×HSM medium (Oyama Y. et al., 2006, Planta, 224:646-654) can be used, and for *Chlorella kessleri*, the 0.2× Gamborg's medium (Izumo A. et al., 2007, Plant Science, 172: 1138-1147) and so forth can be used. *Neochloris oleoabundans* and *Nannochloris* sp. can be cultured by using the modified NORO medium (Yamaberi, K. et al., 1998, J. Mar. Biotechnol., 6:44-48; Takagi, M. et al., 2000, Appl. Microbiol. Biotechnol., 54:112-117) or the Bold's basal medium (Tornabene, T. G. et al., 1983, Enzyme and Microb. Technol., 5:435-440; Archibald, P. A. and Bold, H. C., 1970, Phytomorphology, 20:383-389). For *Thalassiosira pseudonana* as an alga belonging to the class Bacillariophyceae, the F/2 medium (Lie, C.-P. and Lin, L.-P., 2001, Bot. Bull. Acad. Sin., 42:207-214) and so forth can be used. Furthermore, a photobioreactor can also be used for culture of microalgae (WO2003/094598).

The culture can be performed by adding 1 to 50% of a precultured cell suspension, usually based on the volume of the main culture. The initial pH can be around neutral, for example, 7 to 9, and the pH is not adjusted during the culture in many cases. However, the pH may be adjusted if needed. The culture temperature can be between 25 to 35° C., and in particular, a temperature around 28° C. is generally frequently used. However, the culture temperature may be a temperature suitable for the chosen alga. Usually, the culture medium is aerated at a rate of 0.1 to 2 vvm (aeration volume per unit culture medium volume per minute). Furthermore, $CO_2$ may also be added to the medium in order to promote growth, and an exemplary rate is 0.5 to 5% of the aeration rate. Although optimum illumination intensity of light also differs depending on the type of microalgae, the illumination intensity can be about 1,000 to 10,000 lux. As the light source, it is common to use a white fluorescent indoor lamp, but the light source is not limited to this. It is also possible to perform the culture outdoors with sunlight. The culture medium may be stirred at an appropriate intensity, or circulated, if needed. Furthermore, it is known that algae accumulate fats and oils in alga bodies when the nitrogen source is depleted (Thompson G. A. Jr., 1996, Biochim. Biophys. Acta, 1302:17-45), and a limited nitrogen source can be present in the main culture medium.

The culture of microalga can include a culture medium containing alga bodies, as well as alga bodies collected from a culture medium.

Alga bodies can be collected from the culture medium by centrifugation, filtration, gravitational precipitation using a flocculant, or the like (Grima, E. M. et al., 2003, Biotechnol. Advances, 20:491-515).

<2> Method for Processing Microalga and Processed Products of Microalga

The processed product of microalgae can include a mixture of organic substances derived from disrupted cells of microalgae. This product can promote or increase the production and accumulation of an L-amino acid by a bacterium, and examples include, specifically, (1) a culture of microalgae which is disrupted, that is a disruption product, (2) an extract or a fractionation product of a disruption product which contains a mixture of organic substances derived from the microalgae, and (3) a hydrolysate of the disruption product, the extract, or the fractionation product.

The expression "to promote or increase production and accumulation of an L-amino acid" can mean that the mixture of organic substances derived from the disrupted culture of cells of microalgae substantially contributes to the proliferation of a bacterium and L-amino acid production. The mixture of organic substances derived from the disrupted culture of cells of microalgae can act as a source of carbon useful for production of cellular components and L-amino acids. Any processed products that can contribute in such a manner as described above are included as "processed products which promote production and accumulation of an L-amino acid".

Whether a processed product promotes production and accumulation of an L-amino acid can be confirmed by culturing the bacterium under the same conditions in the presence and absence of the processed product, and comparing the production and accumulation amounts of the L-amino acid in the cultures.

Although the production of L-amino acids can be improved to any degree compared with the production of L-amino acids observed without the processed product, the L-amino acid production can be improved by 10% or more, or in another example, 20% or more, or in another example, 30% or more, as compared with a culture without the processed product.

The phrase "to promote production and accumulation of an L-amino acid" can also mean to improve the growth rate of the microorganism, and to increase of number of cells of the microorganism, in a culture medium by the addition of the processed product. The growth rate and number of cells can be increased by 10% or more, or in another example, 20% or more, or in another example, 30% or more, as compared with a culture without the processed product.

Furthermore, when the processed product contains a carbon source, if it can substantially contribute to growth of the bacterium and L-amino acid production, it can be a processed product which promotes production and accumulation of an L-amino acid. Therefore, although any processed product which increases L-amino acid production and accumulation amounts is included, a processed product which improves L-amino acid production and accumulation amounts as compared with when a carbon source is added which includes purified substances in the same amount as the carbon source in the processed product is one example.

Furthermore, if the processing steps for purifying the carbon source are shortened as compared with when using a carbon source of purified substances, the L-amino acid production and accumulation can be improved. In this case, the time of the processing steps can be shortened by 10% or more, or in another example, 20% or more, or in another example, 30% or more.

In addition, the processed product can be obtained by disruption, extraction, fractionation, hydrolysis, and arbitrary combinations of these methods, by determining the ability to promote production and accumulation of L-amino acid as an index.

The culture can be disrupted by any method, so long as the alga bodies are sufficiently disrupted. For example, disruption can include heating the culture to a high temperature, for example, 100° C. or higher, or in another example, 150° C. or higher, or in another example, 175 to 215° C. Disruption can also include treating the culture with an organic solvent, for example, a a mixture of methanol and chloroform, boiling the culture, treating the culture with a strong alkali, subject the culture to ultrasonication, a French press, and so forth, as well as arbitrary combinations of methods. The culture can be subjected to a high temperature and a high pressure reaction, also called a hydrothermal reaction. Furthermore, after alga bodies are dried, they can be disrupted by physical means. A solution of organic substances derived from the disrupted algae can be used as is, or it can be further subjected to hydrolysis. Furthermore, insoluble matter such as cell walls can be removed from the solution by filtration, centrifugation, or the like, or the solution can also be concentrated by lyophilization or the like. Furthermore, a solution containing starches subjected to fractionation to a certain degree can also be used. For fractionation of starches from a disruption product of alga bodies, protein fractions can be separated and collected on the basis of the difference in specific gravity, for example, precipitation rate in a suspension etc. Furthermore, fats and oils can also be fractionated from the disruption product of alga bodies. By adding 80% methanol or 80% acetone to the disruption product of alga bodies, or a concentrate of the disruption product, and extracting insoluble fats and oils in methanol or acetone with a solvent such as hexane and chloroform, fats and oils can be extracted as a crude liposoluble fraction.

The mixture of organic substances derived from the microalgae can contain a substance that can be used as a carbon source. In such a case, the carbon source can be separately added to the medium for amino acid fermentation, and can then be reduced or removed. Examples of the substance that can be used as a carbon source include hydrolysates of starches and/or fats and oils.

When the mixture of organic substances derived from microalgae contains starches, the starches can be saccharified, and the product can be added to the medium as the carbon source. The saccharification product can be obtained from, for example, an organic substance solution derived from the microalgae or a fractionation product thereof containing starches produced by a chemical method such as acidolysis or an enzymatic reaction using amylase.

Starches are high molecular weight polysaccharides, such as amylose which is made up of glucose residues linearly linked by $\alpha$-1,4-glycoside linkages, and amylopectin which is also made up of glucose residues linearly linked by $\alpha$-1,4-glycoside linkages, but also includes branches of $\alpha$-1,6-glycoside linkages. Amylase is the generic name for enzymes that hydrolyze glycoside linkages of starches etc. Depending on the active site, the amylases are roughly classified into $\alpha$-amylase (EC 3.2.1.1), $\beta$-amylase (EC 3.2.1.2) and glucoamylase (EC 3.2.1.3). $\alpha$-Amylase is an endo-type enzyme which randomly cleaves $\alpha$-1,4-glycoside linkages of starches, glycogen, and so forth. $\beta$-Amylase is an exo-type enzyme which cleaves $\alpha$-1,4-glycoside linkage to excise maltose units one by one from the non-reducing end of starch. The glucoamylase (also called amyloglucosidase) is an exo-type enzyme which cleaves $\alpha$-1,4-glycoside linkages to excise glucose units one by one from the non-reducing end of starch, and also cleaves the $\alpha$-1,6-glycoside linkages contained in amylopectin. Glucoamylase is widely used for the production of glucose from starch.

There are many examples of saccharification reactions of starches derived from grains, which have been also industrially implemented (Robertson, G. H. et al., 2006, J. Agric. Food Chem., 54:353-365). In the same manner as these examples, a saccharification product can be obtained from alga bodies by an enzymatic reaction. Boiling, ultrasonication, treatment with alkaline, and so forth in combination, can be used as a pretreatment prior to subjecting a solution containing disrupted alga bodies to an enzyme treatment (Izumo A. et al., 2007, Plant Science, 172:1138-1147).

Conditions of the enzymatic reaction can be suitably determined according to the characteristics of the chosen enzyme. For example, for amyloglucosidase (Sigma Aldrich, A-9228), an enzyme concentration of 2 to 20 U/mL, a temperature of 40 to 60° C., and pH 4 to 6 can be used. If an organic acid that can be assimilated by the chosen bacterium is used to adjust the pH, the organic acid can be used as the carbon source in addition to the saccharification product of starches. For example, the enzyme reaction product can be added to the medium.

The saccharification product of starches produced by microalgae includes material prepared by hydrolyzing starches to produce oligosaccharides or monosaccharides such as maltose or glucose, which can be assimilated by bacteria. Furthermore, in the saccharification product of starches produced by the microalgae, substantially all the starches can be saccharified, or only a portion can be saccharified. A saccharification product in which 50% by weight or more, or in another example, 70% by weight or more, or in another example, 90% by weight or more, of starches are converted into glucose can be used. Furthermore, the saccharification product of starches produced by microalgae can contain carbohydrates other than starches, which are produced by the microalgae or saccharification products thereof.

When the mixture of organic substances derived from microalgae contains fats and oils produced by the microalgae, a hydrolysate thereof can also be added to the medium as the carbon source. Although it is also possible to hydrolyze a crude extract of alga bodies of microalgae which have been disrupted by a heat treatment or the like, a mixed solution of organic substances extracted with a solvent such as ethanol, a mixture of methanol and chloroform or acetone can also be subjected to hydrolysis. These solutions can be used as they are, or they can also be concentrated by further processing such as lyophilization and evaporation. This solution contains components that can be used as an organic nitrogen source for amino acids etc., and components effective for growth of bacteria having an amino acid-producing ability such as metals, and can also be used as a medium component other than or in addition to the carbon source. The fats and oils produced by microalgae can be in any form, so long as hydrolysis, such as hydrolysis with an enzyme, of the fats and oils is possible, and specific examples include disrupted alga bodies, an extract of disrupted alga bodies containing fats and oils, a fractionation product obtained from the extract containing fats and oils, and so forth. Furthermore, the extract or the fractionation product can contain organic substances effective for amino acid fermentation other than fats and oils.

Fats and oils are esters formed from aliphatic acids and glycerol, and can also be called triglycerides. Fats and oils produced by microalgae can be aliphatic acid species generated by hydrolysis which can be utilized by the chosen bacterium as the carbon source. Examples of long chain aliphatic acid species which are able to be assimilated by L-amino acid-producing bacteria include lauric acid, myristic acid, palmitic acid, stearic acid, oleic acid, and so forth. Furthermore, besides fats and oils, organisms generally contain lipids, which release aliphatic acids by hydrolysis. These aliphatic acids produced by the hydrolysis of lipids can also be used as the carbon source. Examples of these lipids include waxes and ceramides, which are simple lipids, as well as phospholipids and glycolipids, which are complex lipids, and so forth.

The hydrolysate of fats and oils can refer to a hydrolysate obtained by hydrolyzing the aforementioned fats and oils of microalgae by either a chemical or enzymatic method. Chemical hydrolysis can be performed by heating at a continuous high temperature (250 to 260° C.) and high pressure (5 to 6 MPa) so that fats and oils and water are brought into contact with each other via countercurrents. Furthermore, it is known that hydrolysis of fats and oils can occur in the presence of a strong acid or an acid catalyst (U.S. Pat. No. 4,218, 386). Furthermore, hydrolysis at a low temperature (around 30° C.) using an enzyme has also been industrially performed (Jaeger, K. E. et al., 1994, FEMS Microbiol. Rev., 15:29-63). Lipase can be used as the enzyme catalyst of the hydrolysis reaction of fats and oils.

Specifically, for example, when using equal amounts of fats and oils and water in a small pressure vessel, and stirring the mixture for about 1 hour at 200° C., a hydrolysis rate of about 70 to 80% can be obtained. In industry, a high temperature (250 to 260° C.) and high pressure (5 to 6 MPa) are typically used. On the other hand, hydrolysis using an enzymatic method can be performed under milder conditions. Hydrolysis using an enzyme is commonly performed by stirring water and fats and oils at a temperature suitable for the lipase reaction. Lipases are industrially important enzymes, and are industrially used in various ways (Hasan, F. et al., 2006, Enzyme and Microbiol. Technol., 39:235-251). One or more kinds of enzymes may be used.

Lipases are enzymes that hydrolyze fat or oil into aliphatic acids and glycerol, and are also called triacylglycerol lipases, or triacylglyceride lipases.

Lipases are found in various organisms, and can be derived from any species sed so long as the chosen lipase catalyzes the aforementioned reaction. In recent years, various attempts have also been made to produce biodiesel fuel, which is made up of aliphatic acid esters, from fat or oil and an alcohol by using a lipase enzyme (Fukuda, H., Kondo, A., and Noda, H., 2001, J. Biosci. Bioeng., 92, 405-416).

Typical, known lipases include those derived from bacteria of the genus *Bacillus, Burkholderia, Pseudomonas* or *Staphylococcus* (Jaeger, K. E., and Eggert, T., 2002, Curr. Opin. Biotechnol., 13:390-397).

The nucleotide sequence of the gene coding for LipA derived from *Bacillus subtilis* (GenBank Accession No. M74010), and the encoded amino acid sequence are shown in SEQ ID NOS: 1 and 2, respectively.

The nucleotide sequence of the gene coding for LipA derived from *Burkholderia glumae* (GenBank Accession No. X70354), and the encoded amino acid sequence are shown in SEQ ID NOS: 3 and 4, respectively.

The nucleotide sequence of the gene coding for LipA derived from *Pseudomonas aeruginosa* (GenBank Accession No. D50587), and the encoded amino acid sequence are shown in SEQ ID NOS: 5 and 6, respectively.

The nucleotide sequence of the lipase derived from *Staphylococcus aureus* (GenBank Accession No. M12715), and the encoded amino acid sequence are shown in SEQ ID NOS: 7 and 8, respectively.

The lipase derived from yeast, such as *Candida antarctica* (GenBank Accession No. Z30645), can be used (Breivik, H., Haraldsson, G. G., and Kristinsson, B., 1997, J. Am. Oil Chem. Soc., 74, 1425-1429). The nucleotide sequence of the gene coding for this lipase and the encoded amino acid sequence are shown in SEQ ID NOS: 9 and 10, respectively.

Furthermore, five or more lipases encoded by separate genes are known for the yeast *Candida rugosa* (*Candida cylindracea*) (Alberghina, L. and Lotti, M., 1997, Methods Enzymol., 284:246-260). As major lipases, LIP1 and LIP2 are known, and the nucleotide sequence of the lip1 gene (GenBank Accession No. X64703) coding for LIP1 and its amino acid sequence are shown in SEQ ID NOS: 11 and 12, respectively. The nucleotide sequence of the lip2 gene (GenBank Accession No. X64703) coding for LIP2 and its amino acid sequence are shown in SEQ ID NOS: 13 and 14, respectively. In addition, it is known that in yeasts of the genus *Candida*, such as *Candida cylindracea*, the CTG codon codes for serine; however, this codon codes for leucine according to the universal codes (Kawaguchi, Y. et al., 1989, Nature, 341: 164-166; Ohama, T. et al., 1993, Nucleic Acids Res., 21:4039-4045). In SEQ ID NOS: 11 to 14, although the amino acids corresponding to CTG are indicated as Leu for convenience, they are actually Ser.

As the aforementioned lipases, those prepared from cells or cultures of the aforementioned microorganisms can be used, or a gene coding for each lipase can be expressed in another host microorganism using genetic engineering techniques. When a gene derived from yeast with a serine-coding CTG codon, such as in *Candida rugosa* (*Candida cylindracea*), is expressed in another host, CTG must be changed to a universal codon coding for serine (Schmidt-Dannert, C., 1999, Bioorg. Med. Chem., 7:2123-2130).

Examples of the characteristics of sequences of lipases include the presence of the GXSXG motif, called a lipase box, near the Ser in the active center, and the conservation of the three residues of Ser, Asp and His, called a catalytic triad, both of which are common to lipases, esterases and serine proteases. For example, in the amino acid sequence of LipA derived from *Bacillus subtilis* shown in SEQ ID NO: 2, the lipase box corresponds to the positions 106 to 110, and the catalytic triad corresponds to the three residues, Ser at the position 108, Asp at the position 164, and His at the position 187.

The hydrolysate of fat or oil can be a mixture of aliphatic acids and glycerol, and the weight ratio of glycerol to aliphatic acids contained in hydrolysate of common fat or oil such as palm oil is about 10%. The hydrolysate can be a reaction product of the hydrolysis reaction, or a fractionation product or purification product of the reaction product, so long as it contains carbon sources that can be assimilated by the chosen bacteria, such as aliphatic acids and glycerol. When the enzyme treatment product of fat or oil contains aliphatic acids, although glycerol and aliphatic acids can be present at an arbitrary ratio, the weight ratio of glycerol and aliphatic acids can be 2 to 50:100, or in another example, 5 to 20:100.

As described above, the hydrolysate of fat or oil usually separates into a lower layer containing glycerol (aqueous phase) and an upper layer containing aliphatic acids (oil phase) at a temperature around room temperature. The lower layer mainly contains glycerol. The upper layer mainly contains aliphatic acids. Although any of these can be used as a carbon source, both glycerol and aliphatic acids can also be used. When a hydrolysate of fat or oil containing both glycerol and aliphatic acids is used, the hydrolysate of fat or oil can be subjected to emulsification. Emulsification can be performed by, for example, adding an emulsification enhancer, stirring, homogenization, ultrasonication, and so forth. Emulsification makes it easier for bacteria to assimilate glycerol and aliphatic acids, and the L-amino acid fermentation becomes more effective. Emulsification can occur by any method, so long as it makes it easier for bacteria having an L-amino acid-producing ability to assimilate aliphatic acids and glycerol. As the emulsification method, for example, addition of an emulsification enhancer or a surfactant etc. can be used. Examples of the emulsification enhancer include phospholipids and sterols. Examples of the surfactant include, as nonionic surfactants, polyoxyethylene sorbitan fatty acid esters such as poly(oxyethylene) sorbitan monooleic acid ester (Tween 80), alkyl glucosides such as n-octyl β-D-glucoside, sucrose fatty acid esters such as sucrose stearate, polyglyceryl fatty acid esters such as polyglycerin stearic acid ester, and so forth. Examples of the surfactant include, as ampholytic surfactants, N,N-dimethyl-N-dodecylglycine betaine, which is an alkylbetaine, and so forth. Besides these, surfactants generally used in the field of biology such as Triton X-100, polyoxyethylene(20) cetyl ether (Brij-58) and nonylphenol ethoxlate (Tergitol NP-40) can be used.

Furthermore, emulsification and homogenization of barely soluble substances, i.e., aliphatic acids, can be improved. Any method which promotes emulsification and homogenization of a mixture of an aliphatic acid and glycerol can be used.

Specific examples include stirring, homogenizer treatment, homomixer treatment, ultrasonication, high pressure treatment, high temperature treatment, and so forth, and stirring, homogenizer treatment, ultrasonication, and a combination of these are particular examples.

The treatment with the aforementioned emulsification enhancer combined with stirring, homogenizer treatment and/or ultrasonication can be carried out under alkaline conditions, since aliphatic acids are more stable. The alkaline condition can be a pH of 9 or higher, or in another example, a pH of 10 or higher.

The concentration of glycerol can be measured by using a kit such as F-Kit Glycerol (Roche Diagnostics) or various biosensors. Moreover, the concentration of aliphatic acids or fat or oil can be measured by gas chromatography (Hashimoto, K. et al., 1996, Biosci. Biotechnol. Biochem., 70:22-30) or HPLC (Lin, J. T. et al., 1998, J. Chromatogr. A., 808:43-49).

<4> Bacteria

A bacterium having an L-amino acid-producing ability can be used. The bacterium is not particularly limited, so long as a bacterium is chosen which can efficiently produce an L-amino acid from the organic substances produced by microalgae, and in particular, a saccharification product of starches or a hydrolysate of fat or oil. Examples of the bacterium include, for example, bacteria belonging to the family Enterobacteriaceae such as those of the genus *Escherichia, Pantoea, Enterobacter*, and so forth, and so-called coryneform bacteria such as those belonging to the genus *Brevibacterium, Corynebacterium, Microbacterium*, or the like, but the bacterium is not limited to these.

The L-amino acid-producing bacterium can be modified to increase the ability to utilize a hydrolysate of fat or oil. Examples of such modification include, for example, deletion of the gene coding for the transcription factor FadR having a DNA-binding ability for controlling the aliphatic acid metabolism observed in enterobacteria (DiRusso, C. C. et al., 1992, J. Biol. Chem., 267:8685-8691; DiRusso, C. C. et al., 1993, Mol. Microbiol., 7:311-322). Specifically, the fadR gene of *Escherichia coli* is at the nucleotide numbers 1,234,161 to 1,234,880 of the genome sequence of *Escherichia coli* MG1655 strain registered with Genbank Accession No. U00096, and codes for the protein registered with GenBank as accession No. AAC74271. The fadR gene sequence is shown in SEQ ID NO: 15.

In the L-amino acid-producing bacterium, a gene involved in the glycerol metabolism can be modified.

As for genes involved in the glycerol metabolism, in order to enhance glycerol assimilability, expression of the glpR gene (EP 1715056) can be attenuated, or expression of the glycerol metabolism genes (EP 1715055 A) such as glpA, glpB, glpC, glpD, glpE, glpF, glpG, glpK, glpQ, glpT, glpX, tpiA, gldA, dhaK, dhaL, dhaM, dhaR, fsa, and talC genes can be enhanced.

In particular, in order to enhance glycerol assimilability, expression of the glycerol dehydrogenase gene (gldA), and the PEP-dependent dihydroxyacetone kinase gene (dhaKLM) or the ATP-dependent dihydroxyacetone kinase gene (dak) can be enhanced in combination. Furthermore, expression of fructose-6-phosphate aldolase (fsaB) can be enhanced (WO2008/102861).

Furthermore, a desensitized-type glycerol kinase gene (glpK) can be used so that the feedback inhibition by fructose-1,6-phosphate is desensitized (WO2008/081959, WO2008/107277).

The family Enterobacteriaceae encompasses bacteria belonging to the genera *Escherichia, Enterobacter, Erwinia, Klebsiella, Pantoea, Photorhabdus, Providencia, Salmonella, Serratia, Shigella, Morganella, Yersinia*, and the like. In particular, bacteria classified into the family Enterobacteriaceae according to the taxonomy used by the NCBI (National Center for Biotechnology Information) database can be used.

The bacterium belonging to the genus *Escherichia* is not particularly limited. However, examples include the bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include the *Escherichia coli* W3110 (ATCC 27325), *Escherichia coli* MG1655 (ATCC 47076) and the like derived from the prototype wild-type strain, the K12 strain.

These strains are available from, for example, the American Type Culture Collection (Address: 12301 10801 University Boulevard, Manassas, Va. 20108, United States of America). That is, registration numbers are given to each of the strains, and the strains can be ordered by these numbers. The registration numbers of the strains are listed in the catalogue of the American Type Culture Collection. The same shall apply to the strains mentioned below with ATCC numbers.

A bacterium belonging to the genus *Pantoea* means that the bacterium is classified into the genus *Pantoea* according to the classification known to a person skilled in the art of microbiology. Some species of *Enterobacter agglomerans* have been recently re-classified into *Pantoea agglomerans, Pantoea ananatis, Pantoea stewartii*, or the like, based on the nucleotide sequence analysis of 16S rRNA, etc. (Int. J. Syst. Bacteriol., 1993, 43, 162-173). Bacteria belonging to the genus *Pantoea* encompass such bacteria re-classified into the genus *Pantoea* as described above.

Typical strains of the *Pantoea* bacteria include *Pantoea ananatis, Pantoea stewartii, Pantoea agglomerans*, and *Pantoea citrea*. Specific examples include the following strains:

*Pantoea ananatis* AJ13356 (FERM BP-6615, European Patent Laid-open No. 0952221)

Although these strains are described as *Enterobacter agglomerans* in European Patent Laid-open No. 0952221, they are currently classified as *Pantoea ananatis* on the basis of recent nucleotide sequence analysis of the 16S rRNA etc., as described above.

Examples of the *Enterobacter* bacteria include *Enterobacter agglomerans, Enterobacter aerogenes*, and the like. Specifically, the strains exemplified in European Patent Application Laid-open No. 952221 can be used. Typical strains of the genus *Enterobacter* include *Enterobacter agglomerans* ATCC 12287 strain.

Examples of the *Erwinia* bacteria include *Erwinia amylovora* and *Erwinia carotovora*, and examples of the *Klebsiella* bacteria include *Klebsiella planticola*. Specific examples include the following strains:

*Erwinia amylovora* ATCC 15580 strain

*Erwinia carotovora* ATCC 15713 strain

*Klebsiella planticola* AJ13399 strain (FERM BP-6600, European Patent Laid-open No. 955368)

*Klebsiella planticola* AJ13410 strain (FERM BP-6617, European Patent Laid-open No. 955368)

The coryneform bacteria also include bacteria which have previously been classified into the genus *Brevibacterium* but have been united into the genus *Corynebacterium* (Liebl and W. et al, 1991, Int. J. Syst. Bacteriol., 41:255-260), and bacteria belonging to the genus *Brevibacterium*, which are closely related to the genus *Corynebacterium*. Specific examples of such coryneform bacteria include the followings:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of these bacteria include the following strains:

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067
*Brevibacterium immariophilum* ATCC 14068
*Brevibacterium lactofermentum* ATCC 13869 (*Corynebacterium glutamicum* TCC 13869)
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

The bacterium having an amino acid-producing ability can refer to a bacterium having the ability to produce an L-amino acid and secrete it in a medium when it is cultured in the medium, specifically so that the objective L-amino acid is produced in the medium in an amount of 0.5 g/L or more, or in another example, 1.0 g/L or more. The L-amino acid includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine. L-Threonine, L-lysine, and L-glutamic acid are particular examples.

Methods for imparting an L-amino acid-producing ability to such bacteria as mentioned above and methods for enhancing an L-amino acid-producing ability of such bacteria as mentioned above are described below.

To impart the ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an L-amino acid analogue-resistant strain, or a metabolic regulation mutant, or by constructing a recombinant strain so that it overexpresses an L-amino acid biosynthesis enzyme. Here, in the breeding of L-amino acid-producing bacteria, one or more of the above-described properties such as auxotrophy, analogue resistance, and metabolic regulation mutation can be imparted. The expression of L-amino acid biosynthesis enzyme(s) can be enhanced alone or in combinations of two or more. Furthermore, the methods of imparting properties such as an auxotrophy, analogue resistance, or metabolic regulation mutation can be combined with enhancement of the biosynthesis enzymes.

An auxotrophic mutant strain, L-amino acid analogue-resistant strain, or metabolic regulation mutant strain with the ability to produce an L-amino acid can be obtained by subjecting a parent or wild-type strain to conventional mutatagenesis, such as exposure to X-rays or UV irradiation, or treatment with a mutagen such as N-methyl-N'-nitro-N-nitrosoguanidine, then selecting those mutants which exhibit autotrophy, analogue resistance, or a metabolic regulation mutation, and which also have the ability to produce an L-amino acid.

Moreover, the L-amino acid-producing ability can also be imparted or enhanced by increasing the enzymatic activity by gene recombination. An example of the method for increasing enzymatic activity includes modifying the bacterium so that the expression of a gene coding for an enzyme involved in the biosynthesis of an L-amino acid is enhanced. Gene expression can also be increased by introducing an amplification plasmid prepared by introducing a DNA fragment containing the gene into an appropriate plasmid which contains, for example, at least a gene responsible for replication and proliferation of the plasmid in the microorganism, increasing the copy number of the gene on the chromosome by conjugation, transfer, or the like, or introducing a mutation into the promoter region of the gene (refer to International Publication WO95/34672).

When an objective gene is introduced into the aforementioned amplification plasmid or chromosome, any promoter can be used to express the gene so long as the chosen promoter functions in bacteria belonging to the coryneform bacteria. The promoter can be the native promoter for the gene, or a modified promoter. The expression of a gene can also be controlled by suitably choosing a promoter that strongly functions in bacteria belonging to coryneform bacteria, or by making the −35 and −10 regions of the promoter closer to the consensus sequence. These methods for enhancing expression of enzyme genes are fully described in International Publication WO00/18935, European Patent Publication No. 1010755, and so forth.

Specific methods for imparting an L-amino acid-producing ability to bacteria and bacteria imparted with L-amino acid-producing ability are exemplified below.

L-Threonine-Producing Bacteria

Examples of microorganisms having L-threonine-producing ability include bacteria in which one or more activities of L-threonine biosynthesis system enzymes are enhanced. Examples of L-threonine biosynthetic enzymes include aspartokinase III (lysC), aspartate semialdehyde dehydrogenase (asd), aspartokinase I (thrA) encoded by thr operon, homoserine kinase (thrB), threonine synthase (thrC), and aspartate aminotransferase (aspartate transaminase) (aspC). The names of the genes coding for the respective enzymes are mentioned in the parentheses after the names of the enzymes (the same shall apply throughout this specification). Among these enzymes, aspartate semialdehyde dehydrogenase, aspartokinase I, homoserine kinase, aspartate aminotransferase, and threonine synthase are particular examples. The genes coding for the L-threonine biosynthetic enzymes can be introduced into an *Escherichia* bacterium which has a reduced ability to decompose threonine. An example of such an *Escherichia* bacterium having a reduced ability to decompose threonine is the TDH6 strain which is deficient in threonine dehydrogenase activity (Japanese Patent Laid-open No. 2001-346578).

The enzymatic activities of the L-threonine biosynthetic enzymes are inhibited by the end product, L-threonine. Therefore, to construct L-threonine-producing strains, the genes for the L-threonine biosynthetic enzymes can be modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, the threonine operon can be modified by removing the leader sequence in the attenuation region or the attenuator (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808).

The native promoter of the threonine operon is present upstream of the threonine operon, and can be replaced with a non-native promoter (refer to WO98/04715). Alternatively, a threonine operon which has been modified so that expression of the threonine biosynthesis gene is controlled by the repressor and promoter of λ-phage can be constructed (EP 0593792). Furthermore, in order to modify a bacterium so that it is desensitized to feedback inhibition by L-threonine, a strain resistant to α-amino-β-hydroxyisovaleric acid (AHV) can be selected.

The copy number of the threonine operon that is modified to be desensitized to feedback inhibition by L-threonine can be increased, or the expression of the threonine operon can be increased by ligating it to a potent promoter. The copy number can also be increased by, besides amplification using a plasmid, transferring the threonine operon to a genome using a transposon, Mu-phage, or the like.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of such genes include the genes encoding transhydrogenase (pntAB, EP 733712 B), phosphoenolpyruvate carboxylase (pepC, WO95/06114), phosphoenolpyruvate synthase (pps, EP 877090 B), and a gene encoding pyruvate carboxylase from coryneform bacterium or *Bacillus* bacterium (WO99/18228, EP 1092776 A).

Resistance to L-threonine, L-homoserine, or both can be imparted to the host by, for example, enhancing expression of a gene that imparts resistance to L-threonine or L-homoserine. Examples of these genes include the rhtA gene (Livshits, V. A. et al., 2003, Res. Microbiol., 154:123-135), rhtB (EP 0994190 A), rhtC gene (EP 1013765 A), yfiK, and yeaS genes (EP 1016710 A). The methods for imparting L-threonine resistance to a host are described in EP 0994190 A and WO90/04636.

Examples of L-threonine-producing bacteria and parent strains which can be used to derive such bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and so forth.

The TDH-6 strain is deficient in the thrC gene, as well as being sucrose-assimilative, and the ilvA gene has a leaky mutation. This strain also has a mutation in the rhtA gene, which imparts resistance to high concentration of threonine or homoserine. The B-3996 strain contains the plasmid pVIC40, which was obtained by inserting the thrA*BC operon, including a mutant thrA gene, into the RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792 B) can also be used as an L-threonine-producing bacterium or a parent strain to derive such a strain. The B-5318 strain is prototrophic with regard to isoleucine, and a temperature-sensitive lambda-phage Cl repressor and PR promoter replace the regulatory region of the threonine operon in the plasmid pVIC40. The VKPM B-5318 strain was deposited as an international deposit at the Russian National Collection of Industrial Microorganisms (VKPM) (1 Dorozhny proezd., 1 Moscow 117545, Russia) on May 3, 1990 under the accession number of VKPM B-5318.

The thrA gene which encodes aspartokinase homoserine dehydrogenase I of *Escherichia coli* is a gene locating at the nucleotide numbers 337 to 2,799 on the genome sequence of the *Escherichia coli* MG1655 strain registered under Genbank Accession No. U00096, and coding for the protein registered under GenBank accession No. AAC73113. The thrB gene which encodes homoserine kinase of *Escherichia coli* is a gene located at the nucleotide numbers 2,801 to 3,733 on the genome sequence of the *Escherichia coli* MG1655 strain registered under Genbank Accession No. U00096, and coding for the protein registered under GenBank accession No. AAC73114. The thrC gene which encodes threonine synthase of *Escherichia coli* is at the nucleotide numbers 3,734 to 5,020 on the genome sequence of the *Escherichia coli* MG1655 strain registered under Genbank Accession No. U00096, and codes for the protein registered under GenBank accession No. AAC73115. These three genes are encoded as the threonine operon (thrLABC) downstream of the thrL gene which codes for the leader peptide. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feedback inhibition by threonine, as well as the thrB and thrC genes can be obtained as one operon from the well-known pVIC40 plasmid, which is present in the threonine-producing *E. coli* strain VKPM B-3996. pVIC40 is described in detail in U.S. Pat. No. 5,705,371.

The rhtA gene imparts resistance to homoserine and threonine (rht: resistant to threonine/homoserine), is located at the nucleotide numbers 848,433 to 849,320 (complementary strand) on the genome sequence of the *Escherichia coli* MG1655 strain registered under Genbank Accession No. U00096, and codes for the protein registered under GenBank accession No. AAC73900. Also, it was revealed that the rhtA23 mutation is an A-for-G substitution at position-1 with respect to the ATG start codon (Livshits, V. A. et al., 2003, Res. Microbiol., 154:123-135, EP 1013765 A).

The asd gene of *E. coli* is at the nucleotide numbers 3,571,798 to 3,572,901 (complementary strand) on the genome sequence of the *Escherichia coli* MG1655 strain registered under Genbank Accession No. U00096, and coding for the protein registered under GenBank accession No. AAC76458. It can be obtained by PCR (refer to White, T. J. et al., Trends Genet, 5, 185 (1989)) utilizing primers prepared based on the nucleotide sequence of the gene. The asd genes of other microorganisms can also be obtained in a similar manner.

The aspC gene of *E. coli* is at the nucleotide numbers 983,742 to 984,932 (complementary strand) on the genome sequence of the *Escherichia coli* MG1655 strain registered under Genbank Accession No. U00096, codes for the protein registered under GenBank accession No. AAC74014, and can be obtained by PCR. The aspC genes of other microorganisms can also be obtained in a similar manner.

L-Lysine-Producing Bacteria

L-Lysine-producing bacteria and methods for constructing them are exemplified below.

Examples of strains having L-lysine-producing ability include, for example, L-lysine analogue-resistant strains and metabolic regulation mutant strains. Examples of L-lysine analogues include, but are not limited to, oxalysine, lysine hydroxamate, S-(2-aminoethyl)-L-cysteine (also abbreviated as "AEC" hereinafter), γ-methyllysine, α-chlorocaprolactam and so forth. Mutant strains having resistance to these lysine analogues can be obtained by subjecting a bacterium belonging to the family Enterobacteriaceae or a coryneform bacterium to a conventional artificial mutagenesis treatment. Specific examples of L-lysine-producing bacteria include *Escherichia coli* AJ11442 (FERM BP-1543, NRRL B-12185, see Japanese Patent Laid-open No. 56-18596 and U.S. Pat. No. 4,346,170), *Escherichia coli* VL611 strain (Japanese Patent Laid-open No. 2000-189180), and so forth. As an L-lysine-producing *Escherichia coli*, the WC196 strain can also be used (see International Publication WO96/17930).

Furthermore, an L-lysine-producing bacterium can also be constructed by increasing activity of an L-lysine biosynthesis system enzyme. An increase of the activity of such an enzyme can be attained by increasing copy number of the gene coding for the enzyme in cells, or by modifying an expression control sequence thereof.

A gene can be modified to enhance expression by, for example, increasing the copy number of the gene in the cells by means of genetic recombination techniques. For example, a recombinant DNA can be prepared by ligating a DNA fragment containing the gapA gene with a vector, such as a multi-copy vector, which is able to function in a host microorganism, and introduced into a bacterium to transform it.

The copy number of a gene can also be increased by introducing multiple copies of the gene into a genomic DNA of a bacterium. In order to introduce multiple copies of a gene into a genomic DNA of a bacterium, homologous recombination is carried out by using a sequence in which multiple copies are present in the genomic DNA as targets. Sequences with multiple copies include repetitive DNA, and inverted repeats present at the end of a transposable element can be used. Another gene can be introduced in tandem with the gapA gene on the genome, or it may be introduced into an unnecessary gene on a genome in a plural number. Such gene transfer can be attained by using a temperature sensitive vector or an integration vector.

Alternatively, as disclosed in Japanese Patent Laid-open No. 2-109985, it is also possible to incorporate the gene into a transposon, and allow it to transfer to introduce multiple copies of the genes into a genomic DNA. Transfer of the gene to the genome can be confirmed by performing Southern hybridization using a part of the gene as a probe.

Furthermore, in addition to the aforementioned increase of the gene copy number, expression of a gene can be enhanced by replacing an expression control sequence such as a promoter of the gene on the genomic DNA or plasmid with a stronger one, by making the −35 and −10 regions of the gene closer to the consensus sequence, by amplifying a regulator that increases expression of the gene, or by deleting or attenuating a regulator that decreases expression of the gene according to the methods described in International Publication WO00/18935. For example, the lac promoter, trp promoter, trc promoter, tac promoter, araBA promoter, lambda phage PR promoter and PL promoter, tet promoter, T7 promoter, Φ10 promoter, and so forth are known as strong promoters. A promoter or SD region of the gapA gene can also be modified so as to become stronger by introducing a nucleotide substitution or the like. Examples of methods for evaluating the strength of a promoter and strong promoters are described in the paper of Goldstein et al. (Prokaryotic promoters in biotechnology, Biotechnol. Annu. Rev., 1995, 1, 105-128) and so forth. In addition, it is known that the substitution of several nucleotides in the spacer region between the ribosome binding site (RBS) and translation initiation codon, especially a sequence immediately upstream from the initiation codon, greatly affects mRNA translation efficiency, and therefore this sequence can be modified. Expression control regions such as promoter of a gene can also be identified by using a promoter search vector or gene analysis software such as GENETYX. By such substitution or modification of promoter as described above, expression of a gene is enhanced. Substitution of an expression control sequence can also be attained by, for example, a method using a temperature-sensitive plasmid or Red-driven integration (WO2005/010175).

Examples of genes coding for L-lysine biosynthetic enzymes include genes coding for enzymes of the diaminopimelate pathway such as the dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyrvate carboxylase gene (ppc) (Japanese Patent Laid-open No. 60-87788), aspartate aminotransferase gene (aspC) (Japanese Patent Publication (Kokoku) No. 6-102028), diaminopimelate epimerase gene (dapF) (Japanese Patent Laid-open No. 2003-135066), and aspartate semialdehyde dehydrogenease gene (asd) (WO00/61723), and genes coding for enzymes of the amino adipic acid pathway such as homoaconitate hydratase gene (Japanese Patent Laid-open No. 2000-157276). In addition, the parent strain may show an increased level of expression of the gene involved in energy efficiency (cyo) (EP 1170376 A), the gene coding for nicotinamide nucleotide transhydrogenase (pntAB) (U.S. Pat. No. 5,830,716), the ybjE gene coding for a protein having L-lysine excretion activity (WO2005/073390), the gene coding for glutamate dehydrogenase (gdhA) (Valle F. et al., 1983, Gene 23:199-209), or an arbitrary combination of these. Abbreviations for the genes are shown in the parentheses.

It is known that the wild-type dihydrodipicolinate synthase and the wild-type aspartokinase, both derived from *Escherichia coli*, are subject to feedback inhibition by L-lysine. Therefore, when the dapA and lysC genes are used, mutant forms of these genes can be used that are desensitized to the feedback inhibition by L-lysine.

Examples of DNA encoding a mutant dihydrodipicolinate synthetase desensitized to feedback inhibition by L-lysine include a DNA encoding a protein having an amino acid sequence in which the histidine residue at the position 118 is replaced by a tyrosine residue. Examples of DNA encoding a mutant aspartokinase desensitized to feedback inhibition by L-lysine include a DNA encoding an AKIII having an amino acid sequence in which the threonine residue at the position 352, the glycine residue at the position 323, and the methionine residue at the position 318 are replaced by isoleucine, asparagine and isoleucine residues, respectively (for these mutants, see U.S. Pat. Nos. 5,661,012 and 6,040,160). Such mutant DNAs can be obtained by site-specific mutagenesis using PCR or the like.

The wide host-range plasmids RSFD80, pCAB1, and pCABD2 contain a mutant dapA gene encoding a mutant dihydrodipicolinate synthase and a mutant lysC gene encoding a mutant aspartokinase (U.S. Pat. No. 6,040,160). *Escherichia coli* JM109 strain transformed with these plasmids was named AJ12396 (U.S. Pat. No. 6,040,160), and the strain was deposited at the National Institute of Bioscience and Human-Technology, Agency of Industrial Science and Technology, Ministry of International Trade and Industry (currently National Institute of Advanced Industrial Science and Technology, International Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a conventional method.

Examples of such enzymes involved in the L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

The expression of both the cadA and ldcC genes encoding lysine decarboxylase can be decreased in order to decrease or delete the lysine decarboxylase activity. Expression of the both genes can be decreased by, for example, the method described in WO2006/078039.

In order to reduce or eliminate activities of these enzymes, a mutation may be introduced into the genes encoding the enzymes on the genome by a usual mutagenesis method or gene recombination technique so that intracellular activities of the enzymes are reduced or eliminated. Such introduction of a mutation can be achieved by, for example, using genetic recombination to eliminate the genes coding for the enzymes on the genome or to modify an expression control sequence such as a promoter or the Shine-Dalgarno (SD) sequence. A mutation for amino acid substitution (missense mutation), a stop codon (nonsense mutation), or a frame shift mutation for adding or deleting one or two nucleotides into regions coding for the enzymes on the genome can be introduced, or the genes can be partially or totally deleted (Wang, J. P. et al., 2006, J. Agric. Food Chem., 54:9405-9410; Winkler W. C., 2005, Curr. Opin. Chem. Biol., 9:594-602; Qiu Z. and Goodman M. F., 1997, J. Biol. Chem., 272:8611-8617; Wente, S. R. and Schachman, H. K., 1991, J. Biol. Chem., 266:20833-20839). The enzymatic activities can also be decreased or eliminated by constructing a gene coding for a mutant enzyme, of which coding region is totally or partially deleted, and substituting it for a normal gene on a genome by homologous recombination or the like, or by introducing a transposon or IS factor into the gene.

For example, in order to introduce a mutation that decreases or eliminates the activities of the above-mentioned enzymes by genetic recombination, the following methods can be used. A mutant gene is prepared by modifying a partial sequence of an objective gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the objective gene on the genome. Examples of such gene substitution using homologous recombination include methods of using a linear DNA such as the method called Red-driven integration (Datsenko, K. A, and Wanner, B. L., 2000, Proc. Natl. Acad. Sci. USA, 97:6640-6645), and the method utilizing the Red driven integration in combination with an excisive system derived from λ phage (Cho, E. H., Gumport, R. I., Gardner, J. F., 2002, J. Bacteriol., 184:5200-5203) (WO2005/010175), a method of using a plasmid containing a temperature sensitive replication origin (U.S. Pat. No. 6,303,383, Japanese Patent Laid-open No. 05-007491), and so forth. Furthermore, such site-specific mutagenesis based on gene substitution using homologous recombination can also be performed by using a plasmid which is not able to replicate in the chosen host.

Examples of L-lysine-producing bacteria can include *Escherichia coli* WC196ΔcadAΔldc/pCABD2 (WO2006/078039). The strain was constructed by introducing the plasmid pCABD2 containing lysine biosynthesis genes (U.S. Pat. No. 6,040,160) into the WC196 strain having disrupted cadA and ldcC genes, which encode lysine decarboxylase. The WC196 strain was bred from the W3110 strain, which was derived from *Escherichia coli* K-12, by replacing the wild type lysC gene on the chromosome of the W3110 strain with a mutant lysC gene encoding a mutant aspartokinase III in which threonine at position 352 was replaced with isoleucine, resulting in desensitization of the feedback inhibition by L-lysine (U.S. Pat. No. 5,661,012), and conferring AEC resistance to the resulting strain (U.S. Pat. No. 5,827,698). The WC196 strain was designated *Escherichia coli* AJ13069, deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldc strain itself is also an exemplary L-lysine-producing bacterium. The WC196ΔcadAΔldc was designated AJ110692, and deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit and assigned an accession number of FERM BP-11027.

The plasmid pCABD2 contains a mutant dapA gene derived from *Escherichia coli* which codes for a dihydrodipicolinate synthase (DDPS) having a mutation for desensitization to the feedback inhibition by L-lysine, a mutant lysC gene derived from *Escherichia coli* which codes for aspartokinase III having a mutation for desensitization to the feedback inhibition by L-lysine, the dapB gene derived from *Escherichia coli* which codes for dihydrodipicolinate reductase, and the ddh gene derived from *Brevibacterium lactofermentum* which codes for diaminopimelate dehydrogenase (International Publications WO95/16042 and WO01/53459).

The procedures described above for enhancing gene expression of the enzymes involved in the L-lysine biosynthesis, and the methods for reducing the enzymatic activities can similarly be applied to genes coding for other L-amino acid biosynthesis enzymes.

Examples of L-lysine producing coryneform bacteria include AEC-resistant mutant strains (*Brevibacterium lactofermentum* AJ11082 (NRRL B-11470) strain etc., refer to Japanese Patent Publication Nos. 56-1914, 56-1915, 57-14157, 57-14158, 57-30474, 58-10075, 59-4993, 61-35840, 62-24074, 62-36673, 5-11958, 7-112437 and 7-112438); mutant strains requiring an amino acid such as L-homoserine for their growth (refer to Japanese Patent Publication Nos. 48-28078 and 56-6499); mutant strains showing resistance to AEC and further requiring an amino acid such as L-leucine, L-homoserine, L-proline, L-serine, L-arginine, L-alanine and L-valine (refer to U.S. Pat. Nos. 3,708,395 and 3,825,472); L-lysine-producing mutant strains showing resistance to DL-α-amino-ε-caprolactam, α-amino-lauryllactam, aspartic acid analogue, sulfa drug, quinoid and N-lauroylleucine; L-lysine-producing mutant strains showing resistance to oxaloacetate decarboxylase or a respiratory tract enzyme inhibitor (Japanese Patent Laid-open Nos. 50-53588, 50-31093, 52-102498, 53-9394, 53-86089, 55-9783, 55-9759, 56-32995, 56-39778, Japanese Patent Publication Nos. 53-43591 and 53-1833); L-lysine-producing mutant strains requiring inositol or acetic acid (Japanese Patent Laid-open Nos. 55-9784 and 56-8692); L-lysine-producing mutant strains that are susceptible to fluoropyruvic acid or a temperature of 34° C. or higher (Japanese Patent Laid-open Nos. 55-9783 and 53-86090); L-lysine-producing mutant strains of *Brevibacterium* or *Corynebacterium* bacteria showing resistance to ethylene glycol (U.S. Pat. No. 4,411,997) and so forth.

L-Cysteine-Producing Bacteria

Examples of L-cysteine-producing bacteria and parent strains which can be used to derive such bacteria include, but are not limited to, *Escherichia* bacteria such as *E. coli* JM15 transformed with multiple kinds of cysE gene alleles encoding serine acetyltransferase resistant to feedback inhibition (U.S. Pat. No. 6,218,168, Russian Patent Application No. 2003121601), *E. coli* W3110 in which a gene encoding a protein suitable for excretion of cytotoxic substances is overexpressed (U.S. Pat. No. 5,972,663), *E. coli* strain having decreased cysteine desulfhydrase activity (Japanese Patent Laid-open No. 11-155571), and *E. coli* W3110 in which activity of the positive transcriptional control factor of the cysteine regulon encoded by the cysB gene is increased (WO01/27307).

L-Leucine-Producing Bacteria

Examples of L-leucine-producing bacteria and parent strains which can be used to derive L-leucine-producing bacteria include, but are not limited to, *Escherichia* bacterial strains, such as *E. coli* strains resistant to leucine (for example, the 57 strain (VKPM B-7386, U.S. Pat. No. 6,124,121)) or leucine analogues including β-2-thienylalanine, 3-hydroxyleucine, 4-azaleucine, 5,5,5-trifluoroleucine, and so forth (Japanese Patent Publication (Kokoku) No. 62-34397 and Japanese Patent Laid-open No. 8-70879), *E. coli* strains obtained by the genetic engineering method described in WO96/06926, *E. coli* H-9068 (Japanese Patent Laid-open No. 8-70879), and so forth.

The bacterium can be improved by enhancing expression of one or more genes involved in L-leucine biosynthesis. Examples of such genes include the genes of the leuABCD operon, a typical example of which is the mutant leuA gene coding for isopropyl malate synthase which has been mutated so that it is desensitized to feedback inhibition by L-leucine (U.S. Pat. No. 6,403,342). In addition, the bacterium can be improved by enhancing expression of one or more genes coding for proteins which increase export of L-amino acid from bacterial cells. Examples of such genes include b2682 and b2683 (the ygaZH genes) (EP 1239041 A2).

Examples of L-isoleucine-producing strains of coryneform bacteria include the coryneform bacterium of which brnE gene coding for a branched chain amino acid excretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), the coryneform bacterium of which homoserine dehydrogenase is enhanced (Japanese Patent Laid-open No. 62-91193), the threonine hydroxamete resistant strain (Japanese Patent Laid-open No 62-195293), α-ketomalonic acid resistant strain (Japanese Patent Laid-open No. 61-15695), and the methyl lysine resistant strain (Japanese Patent Laid-open No. 61-15696).

L-Histidine-Producing Bacteria

Examples of L-histidine-producing bacteria and parent strains which can be used to derive L-histidine-producing bacteria include, but are not limited to, *Escherichia* bacterial strains, such as *E. coli* strain 24 (VKPM B-5945, RU2003677), *E. coli* strain 80 (VKPM B-7270, RU2119536), *E. coli* NRRL B-12116-B 12121 (U.S. Pat. No. 4,388,405), *E. coli* H-9342 (FERM BP-6675), *E. coli* H-9343 (FERM BP-6676) (U.S. Pat. No. 6,344,347), *E. coli* H-9341 (FERM BP-6674) (EP 1085087 A), *E. coli* AI80/pFM201 (U.S. Pat. No. 6,258,554), and so forth.

Examples of L-histidine-producing bacteria and parent strains which can be used to derive L-histidine-producing bacteria also include strains in which the expression of one or more genes encoding L-histidine biosynthetic enzymes is enhanced. Examples of such genes include the genes encoding ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore the ability to produce L-histidine can also be efficiently enhanced by introducing a mutation which confers resistance to feedback inhibition to the gene coding for ATP phosphoribosyltransferase (hisG) (Russian Patent Nos. 2003677 and 2119536).

Specific examples of strains which are able to produce L-histidine include *E. coli* FERM-P 5038 and 5048 which have been transformed with a vector carrying a DNA encoding an L-histidine biosynthetic enzyme (Japanese Patent Laid-open No. 56-005099), *E. coli* strains transformed with a gene encoding a protein involved in amino acid export (EP 1016710 A), *E. coli* 80 strain which is resistant to sulfaguanidine, DL-1,2,4-triazole-3-alanine, and streptomycin (VKPM B-7270, Russian Patent No. 2119536), and so forth.

L-Glutamic Acid-Producing Bacteria

Examples of L-glutamic acid-producing bacteria and parent strains which can be used to derive L-glutamic acid-producing bacteria include, but are not limited to, *Escherichia* bacterial strains, such as *E. coli* VL334thrC$^+$ (EP 1172433). *E. coli* VL334 (VKPM B-1641) is auxotrophic for L-isoleucine and L-threonine and contains mutant thrC and ilvA genes (U.S. Pat. No. 4,278,765). A wild-type allele of the thrC gene was transferred by general transduction using bacteriophage P1 grown on wild-type *E. coli* K12 (VKPM B-7) cells, resulting in the L-isoleucine auxotrophic L-glutamic acid-producing strain VL334thrC$^+$ (VKPM B-8961).

Examples of L-glutamic acid-producing bacteria and parent strains which can be used to derive L-glutamic acid-producing bacteria also include, but are not limited to, strains in which expression of one or more genes encoding an L-glutamic acid biosynthetic enzyme is enhanced. Examples of such genes include the genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (OA), methyl citrate synthase (prpC), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth. Among these enzymes, glutamate dehydrogenase, citrate synthase, phosphoenolpyruvate carboxylase, and methyl citrate synthase are particular examples.

Examples of strains which have been modified so that expression of the citrate synthetase gene, the phosphoenolpyruvate carboxylase gene, and/or the glutamate dehydrogenase gene is enhanced include those disclosed in EP 1078989 A, EP 955368 A, and EP 952221 A.

Examples of L-glutamic acid-producing bacteria and parent strains which can be used to derive L-glutamic acid-producing bacteria also include strains in which the activity of one or more enzymes that catalyze one or more reactions which direct synthesis of one or more compounds other than L-glutamic acid, for example, by directing synthesis away from the biosynthetic pathway of L-glutamic acid, is reduced or eliminated. Examples of these enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and so forth. *Escherichia* bacteria without α-ketoglutarate dehydrogenase activity or with reduced α-ketoglutarate dehydrogenase activity and methods to obtain such bacteria are described in U.S. Pat. Nos. 5,378,616 and 5,573,945.

Specifically, these strains include the following:
*E. coli* W3110sucA::Km$^r$
*E. coli* AJ12624 (FERM BP-3853)
*E. coli* AJ12628 (FERM BP-3854)
*E. coli* AJ12949 (FERM BP-4881)

*E. coli* W3110sucA::Km$^r$ is obtained by disrupting the α-ketoglutarate dehydrogenase gene (hereinafter also referred to as the "sucA gene") of *E. coli* W3110. This strain is completely deficient in α-ketoglutarate dehydrogenase.

Examples of coryneform bacteria with decreased α-ketoglutarate dehydrogenase activity include, for example, the following strains:
*Brevibacterium lactofermentum* L30-2 strain (Japanese Patent Laid-open No. 2006-340603)
*Brevibacterium lactofermentum* ΔS strain (WO95/34672)
*Brevibacterium lactofermentum* AJ12821 (FERM BP-4172, French Patent No. 9401748)
*Brevibacterium flavum* AJ12822 (FERM BP-4173, French Patent No. 9401748)
*Corynebacterium glutamicum* AJ12823 (FERM BP-4174, French Patent No. 9401748)
*Corynebacterium glutamicum* L30-2 strain (Japanese Patent Laid-open No. 2006-340603)

Other examples of L-glutamic acid-producing bacterium include *Escherichia* bacteria which are resistant to an aspartic acid antimetabolite. These strains can also be deficient in α-ketoglutarate dehydrogenase and include, for example, *E. coli* AJ13199 (FERM BP-5807) (U.S. Pat. No. 5,908,768), FFRM P-12379, which additionally is decreased in an activity to decompose L-glutamic acid (U.S. Pat. No. 5,393,671); AJ13138 (FERM BP-5565) (U.S. Pat. No. 6,110,714), and so forth.

An example of an L-glutamic acid-producing bacterium which belongs to *Pantoea ananatis* is the *Pantoea ananatis* AJ13355 strain. This strain was isolated from soil in Iwata-shi, Shizuoka-ken, Japan, and was identified for its ability to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was originally identified as *Enterobacter agglomerans* when it was isolated, and deposited as *Enterobacter agglomerans* AJ13355. However, it was recently re-classified as *Pantoea ananatis* on the basis of nucleotide sequencing of 16S rRNA and so forth.

Furthermore, examples of an L-glutamic acid-producing bacterium of *Pantoea ananatis* also include *Pantoea* bacteria deficient in α-ketoglutarate dehydrogenase (αKGDH) activity or having reduced αKGDH activity. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517) which also does not have the sucA gene, and was selected from AJ13355 for its low phlegm production properties. The AJ13356 strain was deposited at the National Institute of Bioscience and Human-Technology, Agency of Industrial Science and Technology (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted to an international deposit under the provisions of the Budapest Treaty on Jan. 11, 1999, and assigned an accession number of FERM BP-6616. Although the AJ13355 and AJ13356 strains were deposited at the aforementioned depository as *Enterobacter agglomerans*, they are referred to as *Pantoea ananatis* in this specification. The SC17sucA strain was assigned the private number of AJ417, and deposited at the National Institute of Advanced Industrial Science and Technology, International Patent Organism Depositary on Feb. 26, 2004, under an accession number of FERM BP-08646.

Examples of L-glutamic acid-producing *Pantoea ananatis* bacteria further include SC17sucA/RSFCPG+pSTVCB, AJ13601, NP106, and NA1 strains. The SC17sucA/RSFCPG+pSTVCB strain was obtained by introducing the plasmid RSFCPG containing the citrate synthase gene (OA), phosphoenolpyruvate carboxylase gene (ppsA), and glutamate dehydrogenase gene (gdhA) derived from *Escherichia coli*, and the plasmid pSTVCB containing the citrate synthase gene (OA) derived from *Brevibacterium lactofermentum*, into the SC17sucA strain. The AJ13601 strain was selected from the SC17sucA/RSFCPG+pSTVCB strain for its resistance to high concentration of L-glutamic acid at a low pH. Furthermore, the NP106 strain was derived from the AJ13601 strain by eliminating the RSFCPG+pSTVCB plasmid. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned accession number FERM P-17516. Then, the deposit was converted into an international deposit under the provisions of the Budapest Treaty on Jul. 6, 2000, and assigned an accession number FERM BP-7207.

Furthermore, the ability to produce L-glutamic acid can also be imparted to coryneform bacteria by a method of amplifying the yggB gene coding for the mechanosensitive channel (WO2006/070944), and a method of introducing a mutant yggB gene in which a mutation is introduced into the coding region. The yggB gene is located at the nucleotide numbers 1,337,692 to 1,336,091 (complementary strand) of the genome sequence of *Corynebacterium glutamicum* ATCC 13032 strain registered with Genbank Accession No. NC_003450, and coding for a membrane protein also called NCgl1221 and registered with GenBank accession No. NP_600492.

Examples of other methods for imparting or enhancing L-glutamic acid-producing ability also include a method of imparting resistance to an organic acid analogue, a respiratory chain inhibitor, etc., and a method of imparting sensitivity to a cell wall synthesis inhibitor. Examples of such methods include the methods of imparting resistance to monofluoroacetic acid (Japanese Patent Laid-open No. 50-113209), the method of resistance to adenine or thymine (Japanese Patent Laid-open No. 57-065198), the method of attenuating urease (Japanese Patent Laid-open No. 52-038088), the method of imparting resistance to malonic acid (Japanese Patent Laid-open No. 52-038088), the method of imparting resistance to benzopyrones or naphthoquinones (Japanese Patent Laid-open No. 56-1889), the method of imparting resistance to HOQNO (Japanese Patent Laid-open No. 56-140895), the method of imparting resistance to α-ketomalonic acid (Japanese Patent Laid-open No. 57-2689), the method of imparting resistance to guanidine (Japanese Patent Laid-open No. 56-35981), the method of imparting sensitivity to penicillin (Japanese Patent Laid-open No. 4-88994), and so forth.

Specific examples of such resistant strains include the following strains:

*Brevibacterium flavum* AJ3949 (FERM BP-2632; Japanese Patent Laid-open No. 50-113209)
*Corynebacterium glutamicum* AJ11628 (FERM P-5736; Japanese Patent Laid-open No. 57-065198)
*Brevibacterium flavum* AJ11355 (FERM P-5007; Japanese Patent Laid-open No. 56-1889)
*Corynebacterium glutamicum* AJ11368 (FERM P-5020; Japanese Patent Laid-open No. 56-1889)
*Brevibacterium flavum* AJ11217 (FERM P-4318; Japanese Patent Laid-open No. 57-2689)
*Corynebacterium glutamicum* AJ11218 (FERM P-4319; Japanese Patent Laid-open No. 57-2689)
*Brevibacterium flavum* AJ11564 (FERM BP-5472; Japanese Patent Laid-open No. 56-140895)
*Brevibacterium flavum* AJ11439 (FERM BP-5136; Japanese Patent Laid-open No. 56-35981)
*Corynebacterium glutamicum* H7684 (FERM BP-3004; Japanese Patent Laid-open No. 04-88994)
*Brevibacterium lactofermentum* AJ11426 (FERM P-5123; Japanese Patent Laid-open No. 56-048890)
*Corynebacterium glutamicum* AJ11440 (FERM P-5137; Japanese Patent Laid-open No. 56-048890)
*Brevibacterium lactofermentum* AJ11796 (FERM P-6402; Japanese Patent Laid-open No. 58-158192)

L-Phenylalanine-Producing Bacteria

Examples of L-phenylalanine-producing bacteria and parent strains which can be used to derive L-phenylalanine-producing bacteria include, but are not limited to, *Escherichia* bacterial strains, such as *E. coli* AJ12739 (tyrA::Tn10, tyrR) (VKPM B-8197) which lacks chorismate mutase-prephenate dehydrogenase and the tyrosine repressor (WO03/044191), *E. coli* HW1089 (ATCC 55371) which contains the pheA34 gene coding for chorismate mutase-prephenate dehydratase which has been mutated to be desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Also, the following strains can be used to derive L-phenylalanine-producing bacteria: *E. coli* K-12 [W3110(tyrA)/pPHAB (FERM BP-3566) which contains genes coding for chorismate mutase-prephenate dehydratase which has been mutated to be desensitized to feedback inhibition, *E. coli* K-12 [W3110(tyrA)/pPHAD] (FERM BP-12659), *E. coli* K-12 [W3110(tyrA)/pPHATerm] (FERM BP-12662), and *E. coli* K-12 [W3110(tyrA)/pBR-aroG4, pACMAB] (also known as AJ12604 (FERM BP-3579) (EP 488-424 B1). Furthermore, *Escherichia* L-phenylalanine-producing bacteria with enhanced activity of the protein encoded by the yedA gene or the yddG gene can also be used (U.S. Patent Published Applications Nos. 2003/0148473 and 2003/0157667, WO03/044192).

As phenylalanine-producing coryneform bacteria, the *Cornebacterium glutamicum* BPS-13 (FERM BP-1777), K77 (FERM BP-2062), and K78 (FERM BP-2063) (European Patent Laid-open No. 331145, Japanese Patent Laid-open No. 02-303495), of which phosphoenolpyruvate carboxylase or pyruvate kinase activity is reduced, tyrosine-auxotrophic strain (Japanese Patent Laid-open No. 05-049489), and so forth can be used.

A bacterium which efficiently produces phenylalanine can also be obtained by modifying a bacterium so that the bacterium incorporates by-products, for example, by increasing the expression amount of the L-tryptophan uptake gene, tnaB or mtr, or the L-tyrosine uptake gene, tyrP (European Patent No. 1484410).

L-Tryptophan-Producing Bacteria

Examples of L-tryptophan-producing bacteria and parent strains which can be used to derive L-tryptophan-producing bacteria include, but are not limited to, *Escherichia* bacterial strains, such as *E. coli* JP4735/pMU3028 (DSM10122) and *E. coli* JP6015/pMU91 (DSM10123) which lack tryptophanyl-tRNA synthetase encoded by a mutant trpS gene (U.S. Pat. No. 5,756,345), *E. coli* SV164 (pGH5) which contains the serA allele encoding phosphoglycerate dehydrogenase and the trpE allele encoding anthranilate synthase, which are desensitized to feedback inhibition by serine and tryptophan, respectively (U.S. Pat. No. 6,180,373), *E. coli* AGX17 (pGX44) (NRRL B-12263), and *E. coli* AGX6(pGX50)aroP (NRRL B-12264) which lack tryptophanase (U.S. Pat. No. 4,371,614), and *E. coli* AGX17/pGX50,pACKG4-pps in which phosphoenolpyruvate-producing ability is enhanced (WO97/08333, U.S. Pat. No. 6,319,696). L-Tryptophan-producing bacteria belonging to the genus *Escherichia* with enhanced activity of the protein encoded by the yedA gene or the yddG gene can also be used (U.S. Patent Published Application Nos. 2003/0148473 and 2003/0157667).

Examples of L-tryptophan-producing bacteria and parent strains which can be used to derive L-tryptophan-producing bacteria also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (chorismate mutase/prephenate dehydratase, CM/PDH). Among these enzymes, phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, and chorismate mutase-prephenate dehydratase are particular examples. Anthranilate synthase and phosphoglycerate dehydrogenase are both subject to feedback inhibition by L-tryptophan and L-serine, and therefore a mutation desensitizing feedback inhibition can be introduced into the genes encoding these enzymes. Specific examples of strains having such a mutation include *E. coli* SV164 having desensitized anthranilate synthase and a transformant strain obtained by introducing pGH5 (WO94/08031) containing a mutant serA gene coding for phosphoglycerate dehydrogenase desensitized to feedback inhibition into *E. coli* SV164.

Examples of L-tryptophan-producing bacteria and parent strains which can be used to derive L-tryptophan-producing bacteria also include strains which have been transformed with the tryptophan operon, which contains a gene encoding inhibition-desensitized anthranilate synthase (Japanese Patent Laid-open Nos. 57-71397, 62-244382, U.S. Pat. No. 4,371,614). Moreover, L-tryptophan-producing ability can be imparted by enhancing expression of a gene which encodes tryptophan synthase in the tryptophan operon (trpBA). Tryptophan synthase includes both α and β subunits, which are encoded by trpA and trpB, respectively. In addition, L-tryptophan-producing ability can be improved by enhancing expression of the isocitrate lyase-malate synthase operon (WO2005/103275).

As coryneform bacteria, *Corynebacterium glutamicum* AJ12118 (FERM BP-478, Japanese Patent No. 01681002), which is resistant to sulfaguanidine, the coryneform bacterium introduced with the tryptophan operon (Japanese Patent Laid-open No. 63-240794), and the coryneform bacterium introduced with a gene coding for shikimate kinase derived from a coryneform bacterium (Japanese Patent Laid-open No. 01-994749) can be used.

L-Proline-Producing Bacteria

Examples of L-proline-producing bacteria and parent strains which can be used to derive L-proline-producing bacteria include, but are not limited to, *Escherichia* bacterial strains, such as *E. coli* 702ilvA (VKPM B-8012) which lacks the ilvA gene and can produce L-proline (EP 1172433).

The bacterium can be improved by enhancing expression of one or more genes involved in L-proline biosynthesis. Examples of genes useful in L-proline-producing bacteria include the proB gene coding for glutamate kinase which is desensitized to feedback inhibition by L-proline (DE Patent 3127361). In addition, the bacterium can be improved by enhancing expression of one or more genes coding for proteins responsible for secretion of L-amino acids from the bacterial cell. Examples of such genes include the b2682 and b2683 genes (ygaZH genes) (EP 1239041 A2).

*Escherichia* bacteria which produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami Winter Symposium, 1983, p. 34), and so forth.

L-Arginine-Producing Bacteria

Examples of L-arginine-producing bacteria and parent strains which can be used to derive L-arginine-producing bacteria include, but are not limited to, *Escherichia* bacterial strains, such as *E. coli* strain 237 (VKPM B-7925) (U.S. Patent Published Application No. 2002/058315 A1) and its derivative strains harboring mutant N-acetylglutamate synthase (Russian Patent Application No. 2001112869), *E. coli* strain 382 (VKPM B-7926) (EP 1170358 A1), and an arginine-producing strain transformed with an argA gene encoding N-acetylglutamate synthetase (EP 1170361 A1).

Examples of L-arginine-producing bacteria and parent strains which can be used to derive L-arginine-producing bacteria also include strains in which the expression of one or more genes encoding an L-arginine biosynthetic enzyme is enhanced. Examples of such genes include the N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by the produced L-valine. Furthermore, the ilvA gene in the operon can be disrupted so that threonine deaminase activity is decreased.

Examples of L-valine-producing bacteria and parent strains which can be used to derive L-valine-producing bacteria also include mutants having amino-acyl t-RNA synthetase mutations (U.S. Pat. No. 5,658,766). An example is *E. coli* VL1970, which has a mutation in the ileS gene encoding isoleucine tRNA synthetase. *E. coli* VL1970 was deposited at the Russian National Collection of Industrial Microorganisms (VKPM) (1 Dorozhny proezd., 1 Moscow 117545, Russia) on Jun. 24, 1988 under the accession number VKPM B-4411.

Furthermore, mutant strains which require lipoic acid for growth and/or lack $H^+$-ATPase (WO96/06926) are also effective to derive L-valine-producing bacteria.

Examples of L-valine-producing bacteria of coryneform bacteria include, for example, strains modified so that expression of a gene encoding an L-valine biosynthetic enzyme is enhanced. Examples of the L-valine biosynthesis enzyme include enzymes encoded by genes present on the ilvBNC operon, that is, acetohydroxy acid synthetase encoded by ilvBN and isomero-reductase encoded by ilvC (WO00/50624). Since the ilvBNC operon is subject to expression regulation by L-valine and/or L-isoleucine and/or L-leucine, it is desirable to eliminate attenuation to avoid expression suppression by L-valine that is produced.

L-valine-producing ability can be imparted to coryneform bacteria by decreasing or eliminating the activity of at least one kind of enzyme which is involved in a metabolic pathway that decreases L-valine production. For example, a decrease of the activity of threonine dehydratase involved in the L-leucine synthesis, or activity of an enzyme that involved in D-panthothenate synthesis is contemplated (WO00/50624).

Examples of methods for imparting L-valine-producing ability also include imparting resistance to an amino acid analogue or the like.

Examples include, for example, mutant strains which are auxotrophic for L-isoleucine and L-methionine, and resistant to D-ribose, purine ribonucleoside or pyrimidine ribonucleoside, and have an ability to produce L-valine (FERM P-1841, FERM P-29, Japanese Patent Publication No. 53-025034), mutant strains resistant to polyketides (FERM P-1763, FERM P-1764, Japanese Patent Publication No. 06-065314), and mutant strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007, Japanese Patent No. 3006929).

L-Isoleucine-Producing Bacteria

Examples of L-isoleucine producing bacteria and parent strains which can be used to derive L-isoleucine-producing bacteria include, but are not limited to, mutants which are resistant to 6-dimethylaminopurine (Japanese Patent Laid-open No. 5-304969), mutants which are resistant to isoleucine analogues such as thiaisoleucine and isoleucine hydroxamate, and mutants which are additionally resistant to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxate synthase, are also effective to derive L-isoleucine-producing bacteria (Japanese Patent Laid-open No. 2-458, FR 0356739, and U.S. Pat. No. 5,998,178).

Examples of L-isoleucine-producing strains of coryneform bacteria include the coryneform bacterium of which brnE gene coding for a branched chain amino acid excretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), the coryneform bacterium of which homoserine dehydrogenase is enhanced (Japanese Patent Laid-open No. 62-91193), the threonine hydroxamete resistant strain (Japanese Patent Laid-open No 62-195293), α-ketomalonic acid resistant strain (Japanese Patent Laid-open No. 61-15695), and the methyl lysine resistant strain (Japanese Patent Laid-open No. 61-15696).

L-Methionine-Producing Bacteria

Examples of L-methionine-producing bacteria and parent strains for deriving L-methionine producing bacteria include, but are not limited to, L-threonine-auxotrophic mutant strain and norleucine-resistant mutant strain (Japanese Patent Laid-open No. 2000-139471). Furthermore, a methionine repressor-deficient strain and recombinant strains transformed with genes encoding proteins involved in L-methionine biosynthesis such as homoserine transsuccinylase and cystathionine γ-synthase (Japanese Patent Laid-open No. 2000-139471) can also be used as parent strains.

When the aforementioned L-amino acid-producing bacteria are bred by gene recombination, the chosen genes are not limited to genes having the genetic information described above or genes having known sequences, but also include genes having conservative mutations, such as homologues or artificially modified genes, can also be used so long as the functions of the encoded proteins are not degraded. That is, they may be genes encoding a known amino acid sequence containing one or more substitutions, deletions, insertions, additions or the like of one or several amino acid residues at one or several positions.

Although the number of the "several" amino acid residues referred to herein may differ depending on the position in the three-dimensional structure or the types of amino acid residues of the protein, specifically, it can be 1 to 20, or in another example, 1 to 10, or in another example, 1 to 5. The conservative mutation is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. The conservative mutation is typically a conservative substitution, and substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like may be a result of a naturally-occurring mutation or a variation due to an individual difference or difference of species of a microorganism from which the genes are derived (mutant or variant). Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, such genes having conservative mutation(s) as described above may encode a protein having a homology of 80% or more, or in another example, 90% or more, or in another example, 95% or more, or in another example, 97% or more, to the entire encoded amino acid sequence and having a function equivalent to that of the wild-type protein.

Moreover, codons in the gene sequences can be replaced with other codons which are preferred by the chosen host.

The genes having conservative mutation(s) may be obtained by methods usually used in mutagenesis treatments such as treatments with mutagenesis agents.

Furthermore, the genes may be a DNA which can hybridize with a complementary sequence of a known gene sequence or a probe which can be prepared from the complementary sequence under stringent conditions and encodes a protein having a function equivalent to that of the known gene product. The "stringent conditions" referred to here are conditions under which a so-called specific hybrid is formed, and a non-specific hybrid is not formed. Examples of the stringent conditions include those under which highly homologous DNAs hybridize to each other, for example, DNAs not less than 80% homologous, or in another example, not less than 90% homologous, or in another example, not less than 95% homologous, or in another example, not less than 97% homologous, hybridize to each other, and DNAs less homologous than the above do not hybridize to each other, or conditions of washing once, preferably 2 or 3 times, at a salt concentration and temperature corresponding to washing typical of Southern hybridization, i.e., 1×SSC, 0.1% SDS at 60° C., or in another example, 0.1×SSC, 0.1% SDS at 60° C., or in another example, 0.1×SSC, 0.1% SDS at 68° C.

As the probe, a part of the sequence which is complementary to the gene can also be used. Such a probe can be prepared by PCR using oligonucleotides prepared on the basis of the known gene sequence as primers and a DNA fragment containing the nucleotide sequences as a template. For example, when a DNA fragment having a length of about 300 bp is used as the probe, the washing conditions of hybridization may be 50° C., 2×SSC and 0.1% SDS.

The aforementioned descriptions concerning gene homologue and conservative mutation are similarly applied to the aforementioned lipase genes.

<3> Method for Producing L-Amino Acid

In the method for producing an L-amino acid, a bacterium having an L-amino acid-producing ability is cultured in a medium containing the aforementioned processed product of a microalga to produce and accumulate the L-amino acid in culture, and the L-amino acid is collected from the culture. Alternatively, the following steps can be included: (a) a microalga is cultured in a medium, (b) the culture is processed by disruption, extraction, fractionation, and/or hydrolysis resulting in a processed product of the microalga, (c) a bacterium is cultured in a medium containing the processed product of the microalga to produce and accumulate the L-amino acid in culture, and (d) the L-amino acid is collected from the culture. The processed product is present in the medium as the carbon source, and can include a saccharification product of starches or a hydrolysate of fat or oil.

The expression "as the carbon source" can mean that the processed product can substantially contribute to the culture as a source of carbon, which constitutes cellular components and L-amino acids in proliferation of the bacterium and L-amino acid production. If bacterial growth or L-amino acid production and accumulation are more favorable in culture in a medium to which the hydrolysate is added as compared with culture in a medium to which organic substances produced by the microalga are not added, the hydrolysate is considered to be a carbon source. The medium can contain only the organic substances produced by the microalga as the carbon source, or may contain other carbon sources.

A batch culture, fed-batch culture, and continuous culture can be used. The hydrolyzed product of fat or oil in the medium can be present in the starting medium or the feed medium, or both.

The fed-batch culture can refer to a culture method in which the medium is continuously or intermittently added into the culture vessel, and the medium is not extracted until the end of the culture. A continuous culture can refer to a method in which the medium is continuously or intermittently added into the culture vessel, and the medium is extracted from the vessel, usually in a volume equivalent to the volume of added medium, at the same time. The starting medium can mean the medium used in the fed-batch culture or continuous culture before adding the feed medium (medium used at the time of the start of the culture), and the feed medium can mean the medium which is supplied to a fermentation tank in the fed-batch culture or continuous culture. The batch culture can mean a method in which fresh medium is prepared for every culture, and a strain is inoculated into the medium, and the medium is not changed until harvest.

The organic substances produced by the microalga can be at any concentration so long as the concentration is suitable for producing an L-amino acid. The concentration of glucose as a saccharification product of starches in the medium can be about 0.05 to 50 w/v %, or in another example, about 0.1 to 40 w/v %, or in another example, about 0.2 to 20 w/v %. The amount of glycerol and aliphatic acids as a hydrolysate of fat or oil can be present in the medium in an amount of about 0.01 to 10 w/v %, or in another example, about 0.02 to 5 w/v %, or in another example, about 0.05 to 2 w/v %. The organic substances produced by the microalga can be independently used, or can also be used in combination with other carbon sources such as glucose, fructose, sucrose, blackstrap molasses, and starch hydrolysate. In this case, although the organic substances produced by the microalga and other carbon sources can be mixed at an arbitrary ratio, the ratio of the organic substances produced by the microalga in the carbon source can be 10% by weight or more, or in another example, 50% by weight or more, or in another example, 70% by weight or more. Other carbon sources can be saccharides such as glucose, fructose, sucrose, lactose, galactose, blackstrap molasses, starch hydrolysate, and a sugar solution obtained by hydrolysis of biomass, alcohols such as ethanol and glycerol, and organic acids such as fumaric acid, citric acid, and succinic acid.

Furthermore, when the enzymatic hydrolysis of starches is performed in the presence of an organic acid as a buffer, the organic acid may be added to the medium as the carbon source together with the saccharification product. Although the saccharification product of the starches and the organic acid may be present at an arbitrary ratio, the ratio can be 1:1 to 1:3. Although any organic acid that can be assimilated by the bacterium used can be used, examples include, for example, acetic acid, citric acid, succinic acid, fumaric acid, and so forth, and acetic acid is a particular example.

Although the initial concentrations of the saccharification product of starches and the hydrolysate of fat or oil produced by the microalga at the time of start of the culture are as described above, a mixture of the organic substances produced by the microalga can be added as the saccharification product of starches and the hydrolysate of fat or oil produced by the microalga is consumed during the culture.

The organic substances derived from algae can be present at a certain constant concentration throughout the culture process, and can be added only to the feed medium or the starting medium. Alternatively, if other carbon sources are sufficient, there may be a period during the culture when the hydrolysate of fat or oil temporarily is depleted. The term "temporarily" means that, for example, the hydrolysate of fat or oil may be depleted for a period of about 10%, 20%, or 30% at most, of the entire fermentation period. Also, the concentration of the hydrolysate of fat or oil may temporarily be zero, so long as there is a period during the culture when the medium contains organic substances produced by a microalga.

Media conventionally used in the production of L-amino acids by fermentation using microorganisms can be used, provided that the medium contains organic substances produced by algae. That is, conventional media containing, besides a carbon source, a nitrogen source, inorganic ions, and optionally other organic components as required can be used. As the nitrogen source, inorganic ammonium salts such as ammonium sulfate, ammonium chloride, ammonium phosphate, ammonium acetate, and urea, nitrates, organic nitrogen such as soybean hydrolysate, ammonia gas, aqueous ammonia, and so forth may be used. Furthermore, peptone, yeast extract, meat extract, malt extract, corn steep liquor, soybean hydrolysate and so forth can also be utilized. The medium may contain one or more types of these nitrogen sources. These nitrogen sources can also be used for both the starting medium and the feed medium. Furthermore, the same nitrogen source can be used for both the starting medium and the feed medium, or the nitrogen source of the feed medium may be different from that of the starting medium.

The medium can contain a phosphoric acid source and a sulfur source in addition to the carbon source and the nitrogen source. As the phosphoric acid source, potassium dihydrogenphosphate, dipotassium hydrogenphosphate, phosphate polymers such as pyrophosphoric acid and so forth can be utilized. Although the sulfur source can be any substance containing sulfur atoms, sulfuric acid salts such as sulfates, thiosulfates and sulfites, and sulfur-containing amino acids such as cysteine, cystine and glutathione can be used, and ammonium sulfate is a particular example.

Furthermore, the medium can contain a growth promoting factor (nutrient having a growth promoting effect) in addition to the aforementioned components. As the growth promoting factor, trace metals, amino acids, vitamins, nucleic acids as well as peptone, casamino acid, yeast extract, soybean protein degradation product and so forth containing the foregoing substances can be used. Examples of the trace metals include iron, manganese, magnesium, calcium and so forth. Examples of the vitamins include vitamin $B_1$, vitamin $B_2$, vitamin $B_6$, nicotinic acid, nicotinamide, vitamin $B_{12}$ and so forth. These growth promoting factors may be present in the starting medium or the feed medium.

Furthermore, when an auxotrophic mutant that requires an amino acid or the like for growth thereof is used, required nutrients can be added to the medium. In particular, since the L-lysine biosynthetic pathway is enhanced and L-lysine degrading ability is often attenuated in L-lysine-producing bacteria as described below, L-threonine, L-homoserine, L-isoleucine an/or L-methionine can be added. The starting medium and the feed medium can have the same or different composition. Furthermore, the starting medium and the feed medium can have the same or different sulfur concentration. Furthermore, when the feed medium is added at multiple stages, the compositions of the feed media added at the stages may be the same or different.

In addition, the medium can be either a natural or synthetic medium, so long as it contains a carbon source, a nitrogen source, and other components as required.

The organic substances produced by algae contain components used for amino acids in addition to the carbon source. The nitrogen source and other components in the medium used in the present invention can be reduced compared with usual media as required.

The culture can be performed for 1 to 7 days under aerobic conditions. The culture temperature can be 20 to 45° C., or in another example, 24 to 45° C., or in another example, 33 to 42° C. The culture can be performed with aeration, while controlling the oxygen concentration to be about 5 to 50%, or in another example, 10%, of the saturation concentration. Furthermore, pH can be controlled to be 5 to 9 during the culture. To adjust the pH, inorganic or organic acidic or alkaline substances, such as calcium carbonate, ammonia gas, and aqueous ammonia, can be used.

If the culture is performed under such conditions as described above for about 10 to 120 hours, a marked amount of L-amino acid can be accumulated in the culture medium. Although the concentration of the L-amino acid is not limited, so long as it enables isolation and collection of the L-amino acid from the medium or cells, it can be 1 g/L or higher, or in another example, 50 g/L or higher, or in another example, 100 g/L or higher.

When a basic amino acid such as L-lysine is produced, the production can be performed by a method by fermentation while controlling the pH of the medium during culture to be 6.5 to 9.0, the pH of the medium at the end of the culture to be 7.2 to 9.0, and controlling the pressure in the fermentation tank to be positive during the culture. Also, carbon dioxide gas or a mixed gas containing carbon dioxide gas can be added to the medium so that there is a period during the culture where the medium contains 2 g/L 20 mM or more of bicarbonate ions and/or carbonate ions. These bicarbonate ions and/or carbonate ions serve as counter ions of cations mainly consisting of a basic amino acid, and the objective basic amino acid can then be collected (Japanese Patent Laid-open No. 2002-65287, U.S. Patent Published Application No. 2002/0025564, EP 1813677 A).

Furthermore, in L-glutamic acid fermentation, the culture can be performed so that L-glutamic acid precipitates in the medium by using a liquid medium adjusted so that L-glutamic acid is precipitated. The condition under which L-glutamic acid is precipitated can be, for example, pH 5.0 to 4.0, or in another example, pH 4.5 to 4.0, or in another example, pH 4.3 to 4.0, or in another example, pH 4.0 (European Patent Laid-open No. 1078989).

The L-amino acid can be collected from the culture medium by a combination of known methods such as an ion exchange resin method and precipitation method. When the L-amino acid accumulates in the cells, the cells can be disrupted with, for example, supersonic waves or the like, and the L-amino acid can be collected by the ion exchange resin method or the like from the supernatant obtained by removing the cells from the cell-disrupted suspension by centrifugation. The L-amino acid can be in free form, or it can be a salt such as a sulfate, hydrochloride, carbonate, ammonium salt, sodium salt, and potassium salt.

The L-amino acid composition can contain bacterial cells, medium components, moisture, and by-product metabolites of the bacterium, in addition to the objective L-amino acid. The purity of the L-amino acid can be 50% or higher, or in another example, 85% or higher, or in another example, 95% or higher (Japanese Patent No. 1214636, U.S. Pat. Nos. 5,431, 933, 4,956,471, 4,777,051, 4,946,654, 5,840,358, 6,238,714, U.S. Patent Published Application No. 2005/0025878).

Example 1

Hereafter, the present invention will be explained more specifically with reference to the following non-limiting examples. In the examples, the *Chlorella kessleri* 11H strain (UTEX 263), *Neochloris oleoabundans* UTEX 1185 strain, *Nannochloris* sp. UTEX LB 1999 strain, and *Thalassiosira pseudonana* UTEX LB FD2 strain obtained from the University of Texas at Austin, The Culture Collection of Algae (UTEX) (1 University Station A6700, Austin, Tex. 78712-0183, USA) were used.

Example 1

(1) Culture of Microalga *Chlorella kessleri*

*Chlorella kessleri* was cultured at 30° C. and a light intensity of 10,000 lux (culture apparatus: CL-301, TOMY) for 6 days with shaking in 100 mL of the 0.2× Gamborg's B5 medium (NIHON PHARMACEUTICAL) in a 500 mL-volume conical flask, and the resulting culture was used as the preculture. As the light source, white light from a fluorescent lamp was used. The 16 mL of the preculture was added to 800 mL of the 0.2× Gamborg's B5 medium in a 1 L-volume medium bottle, and culture was performed at a culture temperature of 30° C. and a light intensity of 10,000 lux for 12 days with aeration at 500 mL/minute of a mixed gas of air and $CO_2$ so as to obtain a $CO_2$ concentration in the medium of 3%.

0.2× Gamborg's B5 medium:

| | |
|---|---|
| $KNO_3$ | 500 mg/L |
| $MgSO_4 \cdot 7H_2O$ | 50 mg/L |
| $NaH_2PO_4 \cdot H_2O$ | 30 mg/L |
| $CaCl_2 \cdot 2H_2O$ | 30 mg/L |
| $(NH_4)_2SO_4$ | 26.8 mg/L |
| $Na_2$-EDTA | 7.46 mg/L |
| $FeSO_4 \cdot 7H_2O$ | 5.56 mg/L |
| $MnSO_4 \cdot H_2O$ | 2 mg/L |
| $H_3BO_3$ | 0.6 mg/L |
| $ZnSO_4 \cdot 7H_2O$ | 0.4 mg/L |
| KI | 0.15 mg/L |
| $Na_2MoO_2 \cdot 2H_2O$ | 0.05 mg/L |
| $CuSO_4 \cdot 5H_2O$ | 0.005 mg/L |
| $CoCl_2 \cdot 6H_2O$ | 0.005 mg/L |

The medium was sterilized by autoclaving at 120° C. for 15 minutes.

Example 1

(2) Preparation of Saccharified Starch Solution from *Chlorella kessleri*

The alga bodies in 1 L of the culture medium from Example 1 (1) were precipitated by centrifugation, 80 mL of ethanol was added to the precipitates to suspend the alga bodies, and the suspension was boiled for 30 minutes. The suspension was centrifuged to precipitate the alga bodies, and then the alga bodies were washed twice with 80 mL of ethanol and dried in a desiccator. To the dried alga bodies, 40 mL of 0.2 M KOH was added, and the mixture was boiled for 30 minutes, and sonicated with an ultrasonication apparatus (IN-SONATOR 201MA, Kubota) at 15,000 W for 10 minutes to disrupt the cells. To the disrupted cell suspension, 8 mL of a 1 M acetic acid solution and 250 U of an amyloglucosidase (A-9228, Sigma-Aldrich) were added, and the reaction proceeded at 55° C. for 18 hours. After completion of the reaction, glucose in the reaction mixture was quantified with a Biotech Analyzer AS210 (Sakura Seiki). Since the amount of the produced glucose did not substantially change even when the enzyme concentration was doubled, it was presumed that most of starch had been converted into glucose. The disrupted alga bodies (residues) were removed by centrifugation, and the supernatant was used as the carbon source for amino acid fermentation.

Example 1

(3) L-Lysine Production Culture Using Saccharified Starch Solution Derived from *Chlorella kessleri* as the Carbon Source The *Escherichia coli* WC196ΔcadAΔldc/pCABD2 strain described in International Publication WO2006/078039 was used as an L-lysine-producing bacterium. The WC196ΔcadAΔldc/pCABD2 strain was cultured at 37° C. for 20 hours on the LB agar medium (10 g/L of tryptone, 5 g/L of yeast extract, 10 g/L of NaCl, 15 g/L of agar) containing 20 mg/L of streptomycin sulfate. The cells on the agar medium were scraped, inoculated into 40 mL of an L-lysine production medium containing 20 mg/L of streptomycin sulfate contained in a 500 ml-volume conical flask, and cultured at a culture temperature of 37° C. for 24 hours. For the main culture, the saccharified solution of Example 1 (2) prepared from starches produced by *Chlorella kessleri* (2.75 g/L in terms of glucose amount) and 4.8 g/L of acetic acid used as a buffer in the preparation of the saccharified solution were used as carbon sources. As controls, the culture was performed by using the media containing the same concentration of glucose or acetic acid, and the medium containing both glucose and acetic acid as carbon sources.

Composition of L-Lysine Production Medium:

Group A:

| Carbon source | |
|---|---|
| Glucose | 2.75 g/L |
| Acetic acid | 4.8 g/L |

Group B:

| | |
|---|---|
| $(NH_4)_2SO_4$ | 24 g/L |
| $KH_2PO_4$ | 1 g/L |
| Yeast extract | 2 g/L |
| $FeSO_4 \cdot 7H_2O$ | 10 mg/L |
| $MnSO_4 \cdot 4H_2O$ | 10 mg/L |

Group C:

| | |
|---|---|
| Calcium carbonate | 15 g/L |

The components of Groups A and B were sterilized by autoclaving at 115° C. for 10 minutes, and the component of Group C was subjected to hot air sterilization at 180° C. for 3 hours. After the components of the three groups were cooled to room temperature, they were mixed, and an $MgSO_4 \cdot 7H_2O$ solution was added to the mixture to a final concentration of 1 g/L.

After completion of the culture, consumption of the glucose was confirmed with a Biotech Analyzer AS210 (Sakura Seiki), the degree of the growth was measured in terms of live cell count, and the L-lysine amount was measured with BF-5 (Oji Scientific Instruments). Averages of the results of the culture performed in flasks in duplicate are shown in Table 1.

When reagent glucose and acetic acid were each used as the sole carbon source, 1.1 g/L and 0.3 g/L of L-lysine was produced, respectively. When a mixture of reagent glucose and acetic acid was used as the carbon source, 1.4 g/L of L-lysine was produced, which corresponds to the total of L-lysine produced when independently using the carbon sources. With glucose derived from starches produced by the alga and acetic acid at the same concentrations as used above, more than equivalent L-lysine accumulation of 1.8 g/L was observed, and thus it was demonstrated that they are effective carbon sources.

TABLE 1

| Carbon source | Live cell count (×10$^7$) | L-lysine concentration (g/L) |
|---|---|---|
| Alga-derived glucose 2.75 g/L Acetic acid 4.8 g/L | 14.7 | 1.8 |
| Reagent glucose 2.75 g/L Acetic acid 4.8 g/L | 7.6 | 1.4 |
| Reagent glucose 2.75 g/L | 83.0 | 1.1 |
| Acetic acid 4.8 g/L | 6.0 | 0.3 |

Example 2

(1) Preparation of Organic Substance Solution not Containing Starch from *Chlorella kessleri*

The alga bodies in 3.6 L of the culture medium of Example 1 (1) were precipitated by centrifugation, 100 mL of ethanol was added to the precipitates to suspend the alga bodies, and the suspension was left standing at room temperature for 30 minutes. Then, the suspension was filtered, the filtrate was collected, and the alga body residue was extracted twice with 100 mL of ethanol to obtain total 300 mL of ethanol extract. Ethanol was removed from the ethanol extract with a rotating evaporator, then the extract was dissolved in sterilized water, and the solution was adjusted to pH 7.0 with a potassium hydroxide aqueous solution resulting in 45 mL of an organic substance solution derived from the alga bodies. This organic substance solution was sterilized by autoclaving at 115° C. for 10 minutes, and then used in the medium for L-lysine fermentation. Since this organic substance solution did not contain starch, there was no carbon source which could be used by the amino acid-producing bacteria.

Example 2

(2) L-Lysine Production Culture Using Organic Substance Solution not Containing Starch Derived from *Chlorella kessleri* as a Medium Component Other than Carbon Source The L-lysine-producing bacterium, *Escherichia coli* WC196ΔcadAΔldc/pCABD2 strain, was cultured at 37° C. for 20 hours on the LB agar medium containing 20 mg/L of streptomycin sulfate. The cells on the agar medium were scraped, inoculated into 4 mL of an L-lysine production medium containing 20 mg/L of streptomycin sulfate in a large diameter test tube, and cultured at a culture temperature of 37° C. for 24 hours. For the main culture, the culture was performed in a medium obtained by adding 75 μL of the organic substance solution extracted from *Chlorella kessleri* alga bodies obtained in Example 2 (1) (corresponding to 6 mL of the culture medium) to an L-lysine production medium in which contents of the components of Group B were halved (henceforth this medium is referred to as "L-lysine production medium (half amounts for Group B components)". As controls, the culture was performed in the L-lysine production medium, the L-lysine production medium (half amounts for Group B components), and a medium obtained by adding 75 μL of the organic substance solution to the L-lysine production medium (half amounts for Group B components) not containing glucose.

Composition of L-Lysine Production Medium:

Group A:

| | |
|---|---|
| Glucose | 20 g/L |

Group B:

| | |
|---|---|
| $(NH_4)_2SO_4$ | 24 g/L |
| $KH_2PO_4$ | 1 g/L |
| Yeast extract | 2 g/L |
| $FeSO_4 \cdot 7H_2O$ | 10 mg/L |
| $MnSO_4 \cdot 4H_2O$ | 10 mg/L |

Group C:

| | |
|---|---|
| Calcium carbonate | 30 g/L |

The components of Groups A and B were sterilized by autoclaving at 115° C. for 10 minutes, and the component of Group C was subjected to hot air sterilization at 180° C. for 3 hours. After the components of the three groups were cooled to room temperature, they were mixed, and a solution of $MgSO_4 \cdot 7H_2O$ was added to the mixture to a final concentration of 1 g/L.

After completion of the culture, consumption of the glucose was confirmed with a Biotech Analyzer AS210 (Sakura Seiki), the degree of the growth was measured in terms of live cell count, and the amount L-lysine was measured with BF-5 (Oji Scientific Instruments). Averages of the results of the culture performed in large diameter test tubes in duplicate are shown in Table 2.

When the culture was performed in the L-lysine production medium and the L-lysine production medium (half amounts for Group B components), 8.09 g/L and 7.89 g/L of L-lysine was produced, respectively. Furthermore, when the culture was performed in the medium obtained by adding the organic substance solution to the L-lysine production medium (half amounts for Group B components) not containing glucose, the L-lysine amount was 0.14 g/L, and thus the organic substance solution was hardly used as the carbon source. On the other hand, when the culture was performed in the medium obtained by adding the organic substance solution extracted from the alga bodies to the L-lysine production medium (half amounts for Group B components), 8.34 g/L of L-lysine was accumulated, which exceeded the L-lysine amount observed in the L-lysine production medium. Therefore, it was demonstrated that the organic substance solution extracted from the alga bodies was effective in the medium as the carbon source.

TABLE 2

| Medium component | Live cell count (×10$^8$) | L-Lysine concentration (g/L) |
|---|---|---|
| L-Lysine production medium | 22.2 | 8.09 |
| L-Lysine production medium (half amounts for Group B components) | 43.6 | 7.89 |

TABLE 2-continued

| Medium component | Live cell count (×10$^8$) | L-Lysine concentration (g/L) |
|---|---|---|
| L-Lysine production medium (half amounts for Group B components) Organic substance solution extracted from alga bodies | 39.1 | 8.34 |
| L-Lysine production medium (half amounts for Group B components) not containing glucose Organic substance solution extracted from alga bodies | 6.3 | 0.14 |

Example 3

(1) Culture of *Chlorella kessleri* in Jar Fermenter

*Chlorella kessleri* was cultured at 30° C. and a light intensity of 20,000 lux for 7 days in 500 mL of the 0.2× Gamborg's B5 medium (NIHON PHARMACEUTICAL) contained in 2 L-volume jar fermenter (ABLE) with shaking, and the resulting culture medium was used as a preculture. This jar fermenter was a light irradiation type jar fermenter in which a circular fluorescent lamp emitting white light as a light source surrounded a glass vessel. The preculture was added in a volume of 30 mL to 1.5 L of the 0.2× Gamborg's B5 medium in the 2 L-volume mini jar fermenter, and culture was performed at a culture temperature of 30° C. and a light intensity of 20,000 lux for 14 days with aeration of 500 mL/minute of a mixed gas of air and $CO_2$ to maintain a $CO_2$ concentration of 3% in the medium.

Example 3

(2) Preparation of Mixed Solution of Organic Substance Containing Starches by High Temperature Treatment from *Chlorella kessleri* and Preparation of Saccharified Solution with Amylase The alga culture of Example 3 (1) in a volume of 300 mL was put into a reaction vessel of a high temperature reaction apparatus, heated to 175° C. or 215° C. over 60 minutes with stirring, and maintained at each temperature for 5 minutes. The disrupted alga body suspension in a volume of 200 mL subjected to the high temperature treatment at 175° C. was adjusted to pH 5.5 with 3 N HCl, then 500 U of an amyloglucosidase (A-9228, Sigma-Aldrich) was added to the suspension, and the reaction was allowed to proceed at 55° C. for 24 hours with stirring. After completion of the reaction, the suspension was filtered, and the filtrate was collected and concentrated to 10 mL by using a rotating evaporator (EYELA). The concentrate was adjusted to pH 7.8 with 1 N KOH, and after the volume thereof was adjusted to 15 mL, autoclaved at 115° C. for 10 minutes.

Example 3

(3) L-Glutamic Acid Production Culture Using Saccharified Solution Obtained by Amylase Treatment of Mixed Organic Substance Solution Containing Starches Derived from *Chlorella kessleri* Obtained by High Temperature Treatment as Carbon Source The *Brevibacterium lactofermentum* L30-2 strain described in Japanese Patent Laid-open No. 2006-340603 was used as an L-glutamic acid-producing bacterium. The L30-2 strain was inoculated on the CM-Dex plate medium, and cultured at 31.5° C. for 24 hours. One platinum loop of the cells on the plate medium were scraped, inoculated into 4 mL of an L-glutamic acid production medium contained in a large diameter test tube, and cultured at a culture temperature of 31.5° C. for 13 hours. For the main culture, the saccharified solution of Example 3 (2) prepared from the alga starch decomposition product of *Chlorella kessleri* (1.0 g/L in terms of glucose amount), and as a control, reagent glucose of the same concentration were used as carbon sources. The culture was also performed in two kinds of media, the L-glutamic acid production medium, and the L-glutamic acid production medium in which contents of the components of Group B were halved (henceforth this medium is referred to as "L-glutamic acid production medium (half amounts for Group B components)".

CM-Dex Medium:

| | |
|---|---|
| Glucose | 5 g/L |
| Polypeptone | 10 g/L |
| Yeast extract | 10 g/L |
| $KH_2PO_4$ | 1 g/L |
| $MgSO_4 \cdot 7H_2O$ | 0.4 g/L |
| $FeSO_4 \cdot 7H_2O$ | 0.01 g/L |
| $MnSO_4 \cdot 4H_2O$ | 0.01 g/L |
| Urea | 3 g/L |
| Soybean hydrolysate | 1.2 g/L |
| Biotin | 10 µg/L |

The medium was adjusted to pH 7.5 with NaOH, and sterilized by autoclaving at 120° C. for 20 minutes.

Composition of L-Glutamic Acid Production Medium

Group A:

| Carbon source | |
|---|---|
| Decomposition product of starches derived from alga | 1.0 g/L (glucose) |

Group B:

| | |
|---|---|
| $(NH_4)_2SO_4$ | 15 g/L |
| $KH_2PO_4$ | 1 g/L |
| $MgSO_4 \cdot 7H_2O$ | 0.4 g/L |
| $FeSO_4 \cdot 7H_2O$ | 10 mg/L |
| $MnSO_4 \cdot 4H_2O$ | 10 mg/L |
| VB1·HCl | 200 µg/L |
| Biotin | 300 µg/L |
| Soybean hydrolysate | 0.48 g/L |

Group C:

| | |
|---|---|
| Calcium carbonate | 50 g/L |

The component of Groups A and B were adjusted to pH 7.8 and pH 8.0 with KOH, respectively, and sterilized by autoclaving at 115° C. for 10 minutes, and the component of Group C was subjected to hot air sterilization at 180° C. for 3 hours. After the components of the three groups were cooled to room temperature, they were mixed.

After completion of the culture, the L-glutamic acid amount was measured with BF-5 (Oji Scientific Instruments).

Since the L-glutamic acid production medium and the L-glutamic acid production medium (half amounts for Group B components) originally contained 0.45 g/L and 0.24 g/L of L-glutamic acid derived from the soybean hydrolysate, values calculated by subtracting the L-glutamic acid amount in the soybean hydrolysate among the medium components from the measured values are indicated in Table 3.

When the culture was performed in the L-glutamic acid production medium and the L-glutamic acid production medium (half amounts for Group B components) using reagent glucose as a carbon source, 0.74 g/L and 0.57 g/L of L-glutamic acid was produced, respectively. On the other hand, when the decomposition product of starches derived from the alga (alga-derived glucose) was used as the carbon source, the accumulated amounts of L-glutamic acid were 0.84 g/L and 0.70 g/L, and thus it was found that the produced amount of L-glutamic acid was improved as compared with when using the regent glucose. This result demonstrated that the decomposition product of starches derived from the alga was useful as a carbon source of L-glutamic acid production culture.

TABLE 3

| Medium component<br>Carbon source | L-Glutamic acid concentration (g/L) |
|---|---|
| Glutamic acid production medium<br>Reagent glucose 1.0 g/L | 0.74 |
| Glutamic acid production medium<br>(half amounts for Group B components)<br>Reagent glucose 1.0 g/L | 0.57 |
| Glutamic acid production medium<br>Glucose derived from alga 1.0 g/L | 0.84 |
| Glutamic acid production medium<br>(half amounts for Group B components)<br>Glucose derived from alga 1.0 g/L | 0.70 |

Example 4

(1) Preparation of Decomposition Product by Amylase and Lipase of Mixed Solution of Organic Substances Containing Starches Obtained from *Chlorella kessleri* by High Temperature Treatment The disrupted alga body suspension prepared in Example 3 (2), which had been subjected to a high temperature treatment at 215° C., in a volume of 80 mL was adjusted to pH 6.0 with 1 N HCl, then 400 U of an amyloglucosidase (A-9228, Sigma-Aldrich) either alone, or both 400 U of amyloglucosidase and 1000 U of a lipase (L1754, Sigma-Aldrich) were added to the suspension, and the reaction was allowed at 50° C. for 24 hours. After completion of the reaction, each reaction mixture was concentrated to 10 mL. Then, the residue in the mixture treated with the amyloglucosidase alone was removed by centrifugation, the supernatant was adjusted to pH 7.0 with 1 N NaOH, the volume thereof was filled up to 15 mL, and the mixture was autoclaved at 120° C. for 20 minutes. On the other hand, 1.13 mL of a 10% Tween 80 aqueous solution was added to the mixture treated with both the enzymes, and the mixture was warmed to 60° C., and stirred with a vortex mixer. Then, the residue in the mixture treated with both the enzymes was removed by centrifugation, the supernatant was adjusted to pH 7.0 with 1 N NaOH, the volume thereof was filled up to 15 mL, and the mixture was autoclaved at 120° C. for 20 minutes. Glucose and aliphatic acid amounts in each carbon source were measured, and they were used for evaluation by culture.

Example 4

(2) Construction of fadR-Deficient L-Lysine-Producing *Escherichia coli* Strain

The transcription factor FadR which controls aliphatic acid metabolism of *Escherichia coli* is encoded by the fadR gene (SEQ ID NO: 15, DiRusso, C. C. et al., 1992, J. Biol. Chem., 267:8685-8691). As the parent strain used for the gene disruption in this example, the WC196ΔcadAΔldc strain described in International Publication WO2006/078039 was used as an L-lysine-producing strain of *Escherichia coli*.

Deletion of the fadR gene coding for the transcription factor controlling aliphatic acid metabolism was performed by the method called "Red-driven integration", first developed by Datsenko and Wanner (Datsenko, K. A. and Wanner, B. L., 2000, Proc. Natl. Acad. Sci. USA, 97:6640-6645), and an excision system derived from λ phage (Cho E. H., Gumport R. I., and Gardner J. F., 2002, J. Bacteriol., 184:5200-5203). According to the "Red-driven integration" method, using a PCR product obtained by using synthetic oligonucleotides in which a part of a target gene is designed on the 5' side, and a part of antibiotic resistance gene is designed on the 3' side, respectively, as primers, a gene-disrupted strain can be constructed in one step. By further using the excision system derived from λ phage in combination, the antibiotic resistance gene incorporated into the gene-disrupted strain can be removed (Japanese Patent Laid-open No. 2005-058227, WO2005/010175).

As the template for PCR, the plasmid pMW118-attL-kan-attR (Japanese Patent Laid-open No. 2005-058227, WO2005/010175) was used. pMW118-attL-kan-attR is a plasmid obtained by inserting the attachment sites of λ phage, the attL and attR genes, and the kan gene as an antibiotic resistance gene into pMW118 (Takara Bio), and they are inserted in the order of attL-kan-attR.

PCR was performed by using the synthetic oligonucleotides shown in SEQ ID NOS: 16 and 17 as primers, which had sequences corresponding to the ends of the attL and attR at the 3' ends of the primers and a sequence corresponding to a part of the fadR gene as the objective gene at the 5' ends of the primers.

The amplified PCR product was purified on agarose gel, and introduced into the *Escherichia coli* WC196ΔcadAΔldcC strain containing the plasmid pKD46 having temperature sensitive replication ability by electroporation. The plasmid pKD46 (Datsenko, K. A. and Wanner, B. L., 2000, Proc. Natl. Acad. Sci. USA., 97:6640-6645) contains the DNA fragment of 2154 nucleotides in total of λ phage (GenBank/EMBL accession number J02459, 31088th to 33241st nucleotides) containing the genes coding for the Red recombinase of λRed homologous recombination system (γ, β and exo genes) controlled by the arabinose inducible ParaB promoter. The plasmid pKD46 is required in order to incorporate the PCR product into the chromosome of the WC196ΔcadAΔldcC strain.

Competent cells for electroporation were prepared as follows. That is, the *Escherichia coli* WC196 strain cultured overnight at 30° C. in the LB medium (10 g/L of tryptone, 5 g/L of yeast extract, 10 g/L of NaCl) containing 100 mg/L of ampicillin was diluted 100 times with 5 mL of the LB medium containing ampicillin (100 mg/L) and L-arabinose (1 mM). The strain was proliferated in the diluted culture at 30° C. with aeration until the OD600 reached about 0.6, then the culture was concentrated 100 times, and the cells were washed three times with 10% glycerol and thereby made ready for use in electroporation. Electroporation was performed by using 70 μL of the competent cells and about 100 ng of the PCR product. To the cells after the electroporation were added 1 mL of the SOC medium (Sambrook, J., and Russell, D. W., 2001, Molecular Cloning A Laboratory Manual/Third Edition, Cold Spring Harbor Laboratory Press, New York), and the cells were cultured at 37° C. for 1 hour, and then cultured at 37° C. on the LB agar medium containing Km (kanamycin, 40 mg/L) as plate culture to select a Km-resistant recombinant. Then, to remove the pKD46 plasmid, the recombinant was subcultured twice at 42° C. on the LB agar medium containing Km, and the ampicillin resistance of the obtained colonies was examined to obtain an ampicillin-sensitive strain from which the pKD46 was eliminated.

Deletion of the fadR gene in the mutant identified with the kanamycin-resistant gene was confirmed by PCR. The fadR-deficient strain obtained was designated WC196ΔcadAΔldcCΔfadR::att-kan.

Then, to remove the att-kan gene introduced into the fadR gene, a helper plasmid, pMW-intxis-ts (Japanese Patent Laid-open No. 2005-058227, WO2005/010175) was used. pMW-intxis-ts is a plasmid carrying a gene coding for λ phage integrase (Int) and a gene coding for excisionase (Xis), and having temperature sensitive replication ability.

The competent cells of the WC196ΔcadAΔldcCΔfadR::att-kan strain obtained as described above were prepared in a conventional manner, transformed with the helper plasmid pMW-intxis-ts, and cultured at 30° C. on a plate of the LB agar medium containing 100 mg/L of ampicillin to select an ampicillin-resistant strain.

Then, to remove the pMW-intxis-ts plasmid, the ampicillin-resistant transformant was subcultured twice at 42° C. on the LB agar medium, ampicillin resistance and kanamycin resistance of the obtained colonies were examined to obtain a kanamycin and ampicillin-sensitive strain which is an fadR-disrupted strain from which the att-kan and pMW-intxis-ts were eliminated. This strain was designated WC196ΔcadAΔldcCΔfadR.

The WC196LCΔfadR strain was transformed with the plasmid pCABD2 (WO95/16042) for lysine production carrying the dapA, dapB, lysC, and ddh genes in a conventional manner to obtain WC196ΔcadAΔldcCΔfadR/pCABD2.

The strain prepared above was cultured at 37° C. in the LB medium containing 25 mg/L of streptomycin until $OD_{600}$ became about 0.6, then a 40% glycerol solution in the same volume as that of the culture medium was added to the medium, and the mixture was stirred, then divided into appropriate volumes, and stored at −80° C. as glycerol stocks.

Example 4

(3) L-Lysine Production Culture Using Decomposition Product by Amylase and Lipase of Mixed Solution of Organic Substances Containing Starches Obtained from *Chlorella kessleri* by High Temperature Treatment as Carbon Source The L-Lysine-Producing Bacterium, *Escherichia coli* 196ΔcadAΔldcCΔfadR/pCABD2 strain was cultured at 37° C. for 20 hours on the LB agar medium containing 20 mg/L of streptomycin sulfate. The cells on the agar medium were scraped, inoculated into 4 mL of an L-lysine production medium containing 20 mg/L of streptomycin sulfate contained in a large diameter test tube, and cultured at a culture temperature of 37° C. for 24 hours. For the main culture, the saccharified solution of Example 4 (1) prepared from starches produced by *Chlorella kessleri* (1.33 g/L in terms of glucose amount), and the hydrolysis reaction mixture of Example 4 (1) prepared from starches and fat or oil were used as carbon sources. As a control, the culture was performed in a medium containing glucose at the same concentration as a carbon source.

Composition of L-Lysine Production Medium:
Group A:

| Carbon source | |
| --- | --- |
| Decomposition product of starches derived from alga | 1.33 g/L (glucose) |

Group B:

| | |
| --- | --- |
| $(NH_4)_2SO_4$ | 24 g/L |
| $KH_2PO_4$ | 1 g/L |
| Yeast extract | 2 g/L |
| $FeSO_4 \cdot 7H_2O$ | 10 mg/L |
| $MnSO_4 \cdot 4H_2O$ | 10 mg/L |

Group C:

| | |
| --- | --- |
| Calcium carbonate | 15 g/L |

The components of Groups A and B were sterilized by autoclaving at 115° C. for 10 minutes, and the component of Group C was subjected to hot air sterilization at 180° C. for 3 hours. After the components of the three groups were cooled to room temperature, they were mixed, and a solution of $MgSO_4.7H_2O$ was added to the mixture at a final concentration of 1 g/L.

After completion of the culture, consumption of the glucose was confirmed with BF-5 (Oji Scientific Instruments), the degree of the growth was measured in terms of live cell count, and the amount of L-lysine was measured with (Sakura Seiki). Averages of the results of the culture performed in test tubes in duplicate are shown in Table 4.

When reagent glucose was used as the carbon source, 0.6 g/L of L-lysine was produced. From glucose derived from the starches produced by the alga at the same concentration, more than equivalent accumulation of L-lysine of 0.8 g/L was observed, and thus it was demonstrated that it is an effective carbon source. Furthermore, with the saccharification product of starches produced by the alga further subjected to the fat and oil decomposition treatment, 1.0 g/L of L-lysine was produced. It was confirmed that by decomposing fats and oils to convert them into aliphatic acids and glycerol to enable utilization of them by bacteria, utilization of the carbon source by the L-lysine-producing bacterium was improved, and L-lysine accumulation was improved.

TABLE 4

| Carbon source | Culture time (h) | Live cell count ($\times 10^8$) | L-Lysine concentration (g/L) |
| --- | --- | --- | --- |
| Glucose derived from alga 1.33 g/L | 24 | 0.9 | 0.8 |
| Glucose derived from alga 1.24 g/L + oil and fat decomposition product | 24 | 10.5 | 1.0 |
| Reagent glucose 1.33 g/L | 24 | 0.8 | 0.6 |

Example 5

(1) Culture of Microalga *Neochloris oleoabundans*

The *Neochloris oleoabundans* UTEX 1185 strain was cultured at 30° C. and a light intensity of 10,000 lux (culture apparatus: CL-301, TOMY) for 6 days with shaking in 100 mL of the Modified NORO medium contained in a 500 mL-volume conical flask, and the resulting culture was used as a preculture. As the light source, white light from a fluorescent lamp was used. The preculture in a volume of 32 mL was added to 800 mL of the Modified NORO medium contained in a 1 L-volume medium bottle, and culture was performed at a culture temperature of 30° C. and a light intensity of 10,000 lux for 14 days with blowing 500 mL/minute of a mixed gas of air and $CO_2$ into the medium so as to obtain a $CO_2$ concentration of 3%.

Modified NORO Medium:

| | |
|---|---|
| NaCl | 29.22 g/L |
| $KNO_3$ | 1.0 g/L |
| $MgCl_2 \cdot 6H_2O$ | 1.5 g/L |
| $MgSO_4 \cdot 7H_2O$ | 0.5 g/L |
| KCl | 0.2 g/L |
| $CaCl_2 \cdot 2H_2O$ | 0.2 g/L |
| $K_2HPO_4$ | 0.045 g/L |
| Tris(hydroxymethyl)aminomethane | 2.45 g/L |
| $Na_2$-EDTA | 1.89 mg/L |
| $ZnSO_4 \cdot 7H_2O$ | 0.087 mg/L |
| $H_3BO_3$ | 0.61 mg/L |
| $CoCl_2 \cdot 6H_2O$ | 0.015 mg/L |
| $CuSO_4 \cdot 5H_2O$ | 0.06 mg/L |
| $MnCl_2$ | 0.23 mg/L |
| $(NH_4)_6Mo_7O_{24} \cdot 4H_2O$ | 0.38 mg/L |
| Fe(III)•EDTA | 3.64 mg/L |
| Vitamin B1 | 0.1 mg/L |
| Vitamin B12 | 0.5 mg/L |
| Biotin | 0.5 mg/L |

The medium was adjusted to pH 8.0 with 1 N HCl, and then sterilized by autoclaving at 120° C. for 10 minutes.

Example 5

(2) Extraction of Fats and Oils from *Neochloris oleoabundans* and Preparation of Hydrolysate Thereof The alga bodies in 3.6 L of the culture medium of Example 5 (1) were precipitated by centrifugation, and extracted three times as follows. First, the alga bodies were suspended in 100 mL of methanol:chloroform=2:1, and subjected to ultrasonication at 15,000 W for 10 minutes with an ultrasonication apparatus (INSONATOR 201MA, Kubota) to disrupt the cells. The disrupted cell suspension was left standing overnight for extraction, and then the solid matters were removed by filtration to collect the extract.

The extract obtained above was divided into equal volume portions, and each portion was concentrated and used as a crude extract. The crude extract was suspended in 100 mL of 80% methanol, and the suspension and 100 mL of hexane were put into a separating funnel to perform liquid-liquid distribution three times and thereby obtain a hexane layer containing fats and oils (referred to as the fat-and-oil fraction) and a 80% methanol layer containing substantial fraction of water-soluble organic substances (referred to as the water-soluble fraction). The crude extract and the fat-and-oil fraction were mixed with 45 mL of hot water warmed beforehand, 500 U of a lipase (L1754, Sigma-Aldrich, *Candida rugosa*-derived type VII lipase) was added to the mixture, and the reaction was allowed at 42° C. for 20 hours. Aliphatic acid concentrations and glycerol concentrations in the reaction mixtures of the crude extract and the fat-and-oil fraction, and the water-soluble fraction were measured, and they were each used as a carbon source of amino acid fermentation.

Example 5

(3) L-Lysine Production Culture Using Fat and Oil Hydrolysate Derived from *Neochloris oleoabundans* as the Carbon Source The glycerol stocks of the L-lysine-producing bacterium, *Escherichia coli* WC196ΔcadAΔldcC/pCABD2 strain, were thawed, 100 μL of each was uniformly applied to an L-plate containing 25 mg/L of streptomycin, and culture was performed at 37° C. for 20 hours. The cells in an amount of about ⅛ of the cells obtained on one plate were inoculated in 20 mL of the fermentation medium described below containing 25 mg/L of streptomycin, which was contained in a Sakaguchi flask, and cultured at 37° C. for 24 hours on a reciprocally shaking culture apparatus. Each of the samples derived from the alga obtained in Example 5 (2) was suspended in distilled water, Tween 80 was added to the suspension at a concentration of 1%, and the mixture was adjusted to pH 7.0 with 3 N KOH, autoclaved at 120° C. for 20 minutes, and used as the carbon source solution. The medium composition (final concentrations) used for the culture is shown below. The hydrolysate of the crude extract derived from the alga, the hydrolysate of the fat-and-oil fraction derived from the alga, or the water-soluble fraction derived from the alga was used as the carbon source. The totals of the measured aliphatic acid concentration and glycerol concentration of the carbon sources are indicated. Furthermore, as a control, a carbon source of reagent aliphatic acids and reagent glycerol was adjusted so that each were present in equal concentration. Based on the amount of aliphatic acids and glycerol present in the hydrolysate of fats and oils extracted from the microalga *Neochloris oleoabundans*, the control carbon source was prepared so as to contain oleic acid (first grade, Junsei Chemical), linolic acid (Nakarai Tesque), and palmitic acid (special grage, Nakarai Tesque), which were the major aliphatic acids in the hydrolysate, at a weight composition ratio of 4.2:3.8:1.0. The weight composition ratio of aliphatic acids and glycerol was 11.4:1.

L-Lysine Production Medium for *Escherichia* Bacteria

As the carbon source, one of:

Reagent aliphatic acids+reagent glycerol, 1.09 g/L (aliphatic acid concentration+glycerol concentration)

Hydrolysate of the crude extract derived from the alga, 1.09 g/L (aliphatic acid concentration+glycerol concentration)

Hydrolysate of the fat-and-oil fraction derived from the alga, 1.19 g/L (aliphatic acid concentration+glycerol concentration) and Water-soluble fraction derived from the alga, 0.04 g/L (aliphatic acid concentration+glycerol concentration)

| | |
|---|---|
| $MgSO_4 \cdot 7H_2O$ | 1.0 g/L |
| $(NH_4)_2SO_4$ | 24 g/L |
| $KH_2PO_4$ | 1 g/L |
| $FeSO_4 \cdot 7H_2O$ | 0.01 g/L |
| $MnSO_4 \cdot 4H_2O$ | 0.01 g/L |

-continued

| Yeast extract | 2.0 g/L |
| Calcium carbonate | 30 g/L |

The medium was adjusted to pH 7.0 with KOH, and autoclaved at 115° C. for 10 minutes, except that the carbon source and $MgSO_4 \cdot 7H_2O$ were separately sterilized and mixed. Calcium carbonate was subjected to hot air sterilization at 180° C. for 3 hours, and separately added.

After 24 hours, the amount of L-lysine in the culture supernatant was measured with a Biotech Analyzer AS310 (Sakura Seiki). The degree of growth in this medium was determined by measuring the live cell count. Averages of the results of the culture performed in flasks in duplicate are shown in Table 5. The L-lysine concentration obtained by using only a 0.5% solution of the surfactant, Tween 80, as the carbon source as a control was that of L-lysine originally contained in the medium, and thus L-lysine production was not observed. On the other hand, when the enzymatic hydrolysis product of the crude extract derived from the alga was used, favorable L-lysine production was observed. When the hydrolysate of the fat-and-oil fraction extracted from the crude extract derived from the alga was used, more than equivalent L-lysine production was observed compared with that observed with the control carbon source of reagent aliphatic acids and reagent glycerol. Furthermore, even when the water-soluble fraction derived from the crude extract hardly containing aliphatic acids was used as the carbon source, L-lysine production was observed. These results demonstrate that L-lysine production is possible not only with the hydrolysate of the fat-and-oil fraction extracted from the alga bodies of microalga, but also with the water-soluble organic substances. Furthermore, L-lysine production with the hydrolysate of the crude extract of alga bodies greatly exceeded that obtained with the control carbon source of reagent aliphatic acids and reagent glycerol.

TABLE 5

| Carbon source | Live cell count ($\times 10^8$) | L-Lysine concentration (g/L) |
|---|---|---|
| 0.5% Tween 80 | 2.1 | 0.21 |
| Reagent aliphatic acids + reagent glycerol (1.09 g/L) + 0.5% Tween 80 | 6.1 | 0.68 |
| Hydrolysate of crude extract derived from alga (1.09 g/L) + 0.5% Tween 80 | 1.2 | 1.06 |
| Hydrolysate of fat-and-oil fraction derived from alga (1.19 g/L) + 0.5% Tween 80 | 4.5 | 0.73 |
| Water-soluble fraction derived from alga (0.04 g/L) + 0.5% Tween 80 | 4.8 | 0.62 |

Example 6

(1) Culture of *Neochloris oleoabundans*

The *Neochloris oleoabundans* UTEX 1185 strain was cultured at 30° C. and a light intensity of 5,000 lux (culture apparatus: CL-301, TOMY) for 6 days with shaking in 100 mL of the Modified NORO medium contained in a 500 mL-volume conical flask, and the resulting culture was used as a preculture. As the light source, white light from a fluorescent lamp was used. The preculture in a volume of 32 mL was added to 800 mL of the Modified NORO medium contained in a 1 L-volume medium bottle, and culture was performed at a culture temperature of 30° C. and a light intensity of 5,000 lux for 14 days with blowing 500 mL/minute of a mixed gas of air and $CO_2$ into the medium so as to obtain a $CO_2$ concentration of 3%.

Modified NORO Medium:

| NaCl | 29.22 g/L |
| $KNO_3$ | 1.0 g/L |
| $MgCl_2 \cdot 6H_2O$ | 1.5 g/L |
| $MgSO_4 \cdot 7H_2O$ | 0.5 g/L |
| KCl | 0.2 g/L |
| $CaCl_2 \cdot 2H_2O$ | 0.2 g/L |
| $K_2HPO_4$ | 0.045 g/L |
| Tris(hydroxymethyl)aminomethane | 2.45 g/L |
| $Na_2$-EDTA | 1.89 mg/L |
| $ZnSO_4 \cdot 7H_2O$ | 0.087 mg/L |
| $H_3BO_3$ | 0.61 mg/L |
| $CoCl_2 \cdot 6H_2O$ | 0.015 mg/L |
| $CuSO_4 \cdot 5H_2O$ | 0.06 mg/L |
| $MnCl_2$ | 0.23 mg/L |
| $(NH_4)_6Mo_7O_{24} \cdot 4H_2O$ | 0.38 mg/L |
| Fe(III)•EDTA | 3.64 mg/L |
| Vitamin B1 | 0.1 mg/L |
| Vitamin B12 | 0.5 µg/L |
| Biotin | 0.5 µg/L |

The medium was adjusted to pH 8.0 with 1 N HCl, and then sterilized by autoclaving at 120° C. for 10 minutes.

Example 6

(2) Extraction of Lipids from *Neochloris oleoabundans* and Preparation of Hydrolysate Thereof The alga bodies contained in 1.8 L of the culture medium of Example 6 (1) were precipitated by centrifugation, 50 mL of methanol:chloroform=2:1 were added to the precipitates, and the following extraction procedure was repeated three times. First, the alga bodies were suspended in 50 mL of methanol:chloroform=2:1, and left standing overnight for extraction, and then the solid matters were removed by filtration to collect the extract.

The obtained crude extract was suspended in 80 mL of 80% methanol, and the suspension and 100 mL of hexane were put into a separating funnel to perform liquid-liquid distribution three times and thereby obtain a hexane layer containing lipids (referred to as lipid fraction). The lipid fraction were mixed with 50 mL of hot water warmed beforehand, 700 U of a lipase (L1754, Sigma-Aldrich) was added to the mixture, and the reaction was allowed at 42° C. for 18 hours. After completion of the reaction, the solution was concentrated to 30 mL, and divided into 15-mL portions, and one of them was used as a fat-and-oil hydrolysate. Furthermore, in order to hydrolyze glycolipids and phospholipids in another fat-and-oil decomposition product, alkali hydrolysis of the decomposition product was performed as follows. First, the solution of the fat-and-oil decomposition product was prepared so as to contain 0.1 N NaOH as a final molar concentration, and the solution was heated to 95° C. for 90 minutes with stirring on a hot plate to perform alkali hydrolysis. This solution subjected to the lipase treatment and the alkali hydrolysis was used as a total lipid-hydrolyzed hydrolysate.

Example 6

(3) L-Lysine Production Culture Using Lipid Hydrolysate Derived from *Neochloris oleoabundans* as the Carbon Source The glycerol stocks of the L-lysine-producing bacterium, *Escherichia coli* WC196ΔcadAΔldcC/pCABD2 strain, were thawed, 100 μL of each was uniformly applied to an L-plate containing 25 mg/L of streptomycin, and culture was performed at 37° C. for 20 hours. The cells in an amount of about 1/40 of the cells obtained on one plate were inoculated in 4 mL of the fermentation medium described below and containing 25 mg/L of streptomycin, which was in a large diameter test tube, and cultured at 37° C. for 24 hours on a reciprocally shaking culture apparatus. Tween 80 was added at a concentration of 2% to a hydrolysis solution of each of the samples derived from the alga obtained in of Example 6 (2), and the mixture was adjusted to pH 7.0 with 3 N KOH, autoclaved at 120° C. for 20 minutes, and used as the carbon source solution. The medium composition used for the culture is shown below. The component of Group A was the carbon source, and the totals of the measured aliphatic acid concentration and glycerol concentration are indicated.

L-Lysine Production Medium for *Escherichia* Bacteria:
Group A:
Hydrolysate of fats and oils derived from alga, 1.22 g/L (aliphatic acid concentration+glycerol concentration), or
Hydrolysate of total lipids derived from alga, 2.14 g/L (aliphatic acid concentration+glycerol concentration)
Group B:

| | |
|---|---|
| $(NH_4)_2SO_4$ | 24 g/L |
| $KH_2PO_4$ | 1.0 g/L |
| $FeSO_4 \cdot 7H_2O$ | 0.01 g/L |
| $MnSO_4 \cdot 4H_2O$ | 0.01 g/L |
| Yeast extract | 2.0 g/L |

Group C:

| | |
|---|---|
| Calcium carbonate | 30 g/L |

The components of Groups A and B were sterilized by autoclaving at 115° C. for 10 minutes, and the component of Group C was subjected to hot air sterilization at 180° C. for 3 hours. After the components of the three groups were cooled to room temperature, they were mixed, and an $MgSO_4 \cdot 7H_2O$ solution was added to the mixture to a final concentration of 1 g/L.

Since the fat-and-oil decomposition product derived from the alga was subjected to only the lipase treatment, most of glycolipids, phospholipids etc. were hardly decomposed, and only the fats and oils were decomposed. On the other hand, the total lipid decomposition product derived from the alga was subjected to lipase treatment, and then further subjected to the alkali hydrolysis treatment, and therefore not only fats and oils, but also the glycolipids and phospholipids were decomposed. When the totals of aliphatic acid amounts and glycerol amount in those carbon sources were compared, it was confirmed that not only fats and oils, but also glycolipids and phospholipids were decomposed in the total lipid decomposition product, and the carbon source amount thereof was increased to 2.14 g/L from 1.22 g/L of the fat-and-oil hydrolysate. Culture was performed by using these hydrolysates as carbon sources, and L-lysine amounts in the culture supernatants after 24 hours were measured with a Biotech Analyzer AS310 (Sakura Seiki). The degree of the growth in this medium was determined by measuring the live cell count. Averages of the results of the culture performed in duplicate are shown in Table 6. The L-lysine concentration obtained by using only a 0.5% solution of the surfactant Tween 80 as the carbon source as a control was that of L-lysine originally present in the medium, and thus L-lysine production was not observed. On the other hand, when the fat-and-oil decomposition product derived from the alga was used, L-lysine production was observed. When the total lipid decomposition product derived from the alga was used, favorable L-lysine production was observed. These results demonstrated that L-lysine production was possible not only with fats and oils extracted from the alga bodies of the microalga, but also with glycolipids or phospholipids extracted from the alga bodies of the microalga, and L-lysine production was possible with the total lipids of the alga bodies.

TABLE 6

| Carbon source | Live cell count ($\times 10^8$) | L-Lysine concentration (g/L) |
|---|---|---|
| 0.5% Tween 80 | 2.6 | 0.19 |
| Hydrolysate fats and oils derived from alga (1.22 g/L) + 0.5% Tween 80 | 12.3 | 1.00 |
| Total lipid decomposition product derived from alga (2.14 g/L) + 0.5% Tween 80 | 20.0 | 1.51 |

Example 7

(1) Culture of Microalga *Nannochloris* sp

The *Nannochloris* sp. UTEX LB 1999 strain was cultured at 30° C. and a light intensity of 10,000 lux (culture apparatus: CL-301, TOMY) for 6 days with shaking in 100 mL of the Modified NORO medium contained in a 500 mL-volume conical flask, and the resulting culture was used as a preculture. As the light source, white light from a fluorescent lamp was used. The preculture in a volume of 32 mL was added to 800 mL of the Modified NORO medium contained in a 1 L-volume medium bottle, and culture was performed at a culture temperature of 30° C. and a light intensity of 10,000 lux for 14 days with aeration of 500 mL/minute of a mixed gas of air and $CO_2$ into the medium so as to obtain a $CO_2$ concentration of 3%.

Example 7

(2) Extraction of Fats and Oils from *Nannochloris* sp. and Preparation of Hydrolysate Thereof The alga bodies contained in 3.6 L of the culture medium of Example 7 (2) were precipitated by centrifugation, and extracted three times as follows. First, the alga bodies were suspended in 100 mL of methanol:chloroform=2:1, and subjected to ultrasonication at 15,000 W for 10 minutes with an ultrasonication apparatus (INSONATOR 201MA, Kubota) to disrupt the cells. The disrupted cell suspension was left standing overnight for extraction, and then the solid matters were removed by filtration to collect the extract. The obtained extract was concentrated and then suspended in 100 mL of 80% methanol, and the suspension and 100 mL of hexane were put into a separating funnel to perform liquid-liquid distribution three times and thereby obtain a hexane layer containing fats and oils (fat-and-oil fraction) and a 80% methanol layer containing a substantial fraction of water-soluble organic substances (water-soluble fraction). Then, the fat-and-oil fraction was suspended in 40 mL of hot water warmed beforehand, 500 U of a lipase (L1754, Sigma) was added to the suspension, and the reaction was allowed to proceed at 42° C. for 20 hours. Aliphatic acid concentration and glycerol concentration of the reaction mixture and the water-soluble fraction were measured, and they were each used as the carbon source for amino acid fermentation.

Example 7

(3) L-Lysine Production Culture Using Fat-and-Oil Hydrolysate Derived from *Nannochloris* sp. as the Carbon Source The glycerol stocks of the *Escherichia coli* WC196ΔcadAΔldcC/pCABD2 strain were thawed, 100 μL of each was uniformly applied to an L-plate containing 25 mg/L of streptomycin, and culture was performed at 37° C. for 20 hours. The cells in an amount of about ⅛ of the cells obtained on one plate were inoculated in 20 mL of the fermentation medium described below containing 25 mg/L of streptomycin in a Sakaguchi flask, and cultured at 37° C. for 16 hours or 20 hours on a reciprocally shaking culture apparatus. Each of the samples derived from the alga obtained in of Example 7 (2) was suspended in distilled water, Tween 80 was added to the suspension at a concentration of 1%, and the mixture was adjusted to pH 7.0 with 3 N KOH, autoclaved at 120° C. for 20 minutes, and used as the carbon source solution. The medium composition used for the culture is shown below. The hydrolysate of the fat-and-oil fraction derived from the alga, or the water-soluble fraction derived from the alga was used as the carbon source. The totals of the measured aliphatic acid concentration and glycerol concentration of the carbon sources are indicated.

L-Lysine Production Medium for *Escherichia* Bacteria:
One of the following was used as the carbon source:
Hydrolysate of the fat-and-oil fraction derived from the alga, 1.06 g/L (aliphatic acid concentration+glycerol concentration) and
Water-soluble fraction derived from the alga, 0.00 g/L (aliphatic acid concentration+glycerol concentration)

| | |
|---|---|
| MgSO$_4$•7H$_2$O | 1.0 g/L |
| (NH$_4$)$_2$SO$_4$ | 24 g/L |
| KH$_2$PO$_4$ | 1.0 g/L |
| FeSO$_4$•7H$_2$O | 0.01 g/L |
| MnSO$_4$•4H$_2$O | 0.01 g/L |
| Yeast extract | 2.0 g/L |
| Calcium carbonate | 30 g/L |

The medium was adjusted to pH 7.0 with KOH, and autoclaved at 115° C. for 10 minutes, except that the carbon source and MgSO$_4$.7H$_2$O were separately sterilized and mixed. Calcium carbonate was subjected to hot air sterilization at 180° C. for 3 hours, and separately added.

After completion of the culture, the L-lysine amount in the culture supernatant was measured with a Biotech Analyzer AS310 (Sakura Seiki). The degree of the growth in this medium was determined by measuring the live cell count. Averages of the results of the culture performed in flasks in duplicate are shown in Table 7. The L-lysine concentration obtained by using only a 0.5% solution of the surfactant Tween 80 as the carbon source as a control was the same as the L-lysine originally present in the medium, and thus L-lysine production was not observed. On the other hand, when the hydrolysate of the fat-and-oil fraction derived from *Nannochloris* sp. was used, favorable L-lysine production was observed. Furthermore, even when the water-soluble organic substances not containing aliphatic acids as carbon source was used, L-lysine production was also observed.

TABLE 7

| Carbon source | Culture time (h) | Live cell count (×10$^8$) | L-Lysine concentration (g/L) |
|---|---|---|---|
| 0.5% Tween 80 | 20 | 2.1 | 0.12 |
| Hydrolysate of fat-and-oil fraction derived from alga (1.06 g/L) + 0.5% Tween 80 | 16 | 11.1 | 1.02 |
| Water-soluble fraction derived from alga (0.00 g/L) + 0.5% Tween 80 | 20 | 0.5 | 1.23 |

Example 8

(1) Extraction of Crude Organic Substances from *Nannochloris* sp. and Preparation of Hydrolysate of Fats and Oils Alga bodies in 1.2 L of a culture medium of the *Nannochloris* sp. UTEX LB 1999 strain cultured in the same manner as that of Example 7 (1) were precipitated by centrifugation, and were extracted three times as follows. First, the alga bodies were suspended in 100 mL of methanol:chloroform=2:1, and subjected to ultrasonication at 15,000 W for 10 minutes with an ultrasonication apparatus (INSONATOR 201MA, Kubota) to disrupt the cells. The disrupted cell suspension was left standing overnight for extraction, then the solid matters were removed by filtration to collect the extract, and the extract was concentrated. Then, the extract was suspended in 40 mL of hot water warmed beforehand, 500 U of a lipase (L1754, Sigma-Aldrich) was added to the suspension, and the reaction was allowed to proceed at 42° C. for 20 hours. The aliphatic acid and glycerol concentrations were measured in preparation for their use as the carbon source for amino acid fermentation.

Example 8

(2) L-Lysine Production Culture Using Crude Organic Substances Derived from *Nannochloris* sp. as Carbon Source The glycerol stocks of the *Escherichia coli* WC196LC/pCABD2 strain were thawed, 100 μL of each was uniformly applied to an L-plate containing 25 mg/L of streptomycin, and culture was performed at 37° C. for 20 hours. The cells in an amount of about ⅛ of the cells obtained on one plate were inoculated in 20 mL of the fermentation medium described below containing 25 mg/L of streptomycin, which was contained in a Sakaguchi flask, and cultured at 37° C. for 16 hours or 20 hours on a reciprocally shaking culture apparatus. Each of the samples derived from the alga obtained in Example 8 (1) serving as the carbon source was suspended in distilled water, Tween 80 was added to the suspension at a concentration of 1%, and the mixture was adjusted to pH 7.0 with 3 N KOH, autoclaved at 120° C. for 20 minutes, and used as the carbon source solution. The medium composition used for the culture is shown below. The total of the measured aliphatic acid and glycerol concentrations of the hydrolysate of the crude extract derived from the alga is indicated.

L-Lysine Production Medium for *Escherichia* Bacteria:

Hydrolysate of the crude extract derived from the alga, 0.37 g/L (aliphatic acid concentration+glycerol concentration)

| | |
|---|---|
| $MgSO_4 \cdot 7H_2O$ | 1.0 g/L |
| $(NH_4)_2SO_4$ | 24 g/L |
| $KH_2PO_4$ | 1.0 g/L |
| $FeSO_4 \cdot 7H_2O$ | 0.01 g/L |
| $MnSO_4 \cdot 4H_2O$ | 0.01 g/L |
| Yeast extract | 2.0 g/L |
| Calcium carbonate | 30 g/L |

The medium was adjusted to pH 7.0 with KOH, and sterilized by autoclaving at 115° C. for 10 minutes, except that the carbon source and $MgSO_4 \cdot 7H_2O$ were separately sterilized and mixed. Calcium carbonate was subjected to hot air sterilization at 180° C. for 3 hours, and separately added.

After completion of the culture, the L-lysine amount in the culture supernatant was measured with a Biotech Analyzer AS310 (Sakura Seiki). The degree of the growth in this medium was determined by measuring the live cell count. Averages of the results of the culture performed in flasks in duplicate are shown in Table 8. The L-lysine concentration obtained by using only a 0.5% solution of the surfactant Tween 80 as the carbon source as a control was the same as the L-lysine originally present in the medium, and thus L-lysine production was not observed. On the other hand, when the hydrolysate of the crude extract derived from *Nannochloris* sp. was used, L-lysine production was observed.

TABLE 8

| Carbon source | Culture time (h) | Live cell count ($\times 10^8$) | L-lysine concentration (g/L) |
|---|---|---|---|
| 0.5% Tween 80 | 24 | 4.2 | 0.22 |
| Hydrolysate of crude extract derived from alga (0.37 g/L) + 0.5% Tween 80 | 24 | 13.1 | 0.56 |

Example 9

(1) Culture of Diatom *Thalassiosira pseudonana* UTEX LB FD2 Strain

The *Thalassiosira pseudonana* UTEX LB FD2 strain was cultured at a culture temperature of 25° C. and a light intensity of 7,000 lux for 3 days in 500 mL of the F/2 medium in a 1 L-volume medium bottle with aeration of 200 mL/minute of a mixed gas of air and $CO_2$ into the medium so as to obtain a $CO_2$ concentration of 1%, and the resulting culture was used as a preculture. As the seawater component of the F/2 medium, artificial seawater, Aquamarine S (YASHIMA PURE CHEMICALS), was used. The preculture in a volume of 32 mL was added to 800 mL of the F/2 medium in a 1 L-volume medium bottle, and culture was performed at a culture temperature of 25° C. and a light intensity of 7,000 lux for 7 days with aeration of 200 mL/minute of a mixed gas of air and $CO_2$ into the medium so as to obtain a $CO_2$ concentration of 1%. As the light source, white light from a fluorescent lamp was used.

F/2 medium:

| | |
|---|---|
| $NaNO_3$ | 75 mg/L |
| $NaH_2PO_4 \cdot H_2O$ | 5 mg/L |
| $Na_2SiO_3 \cdot 9H_2O$ | 20 mg/L |
| $FeCl_3 \cdot 6H_2O$ | 6.4 mg/L |
| $MnSO_4 \cdot H_2O$ | 0.304 mg/L |
| $ZnSO_4 \cdot 7H_2O$ | 0.046 mg/L |
| $Na_2MoO_4 \cdot 2H_2O$ | 14.6 µg/L |
| $CuCl_2 \cdot 2H_2O$ | 13.6 µg/L |
| $Na_2EDTA \cdot 2H_2O$ | 8.8 mg/L |
| $CoCl_2 \cdot 6H_2O$ | 23.8 µg/L |
| Vitamin B12 | 0.135 mg/L |
| Biotin | 0.025 mg/L |
| Vitamin B1 | 1.1 mg/L |
| Aquamarine S artificial seawater | 40 g/L |

The medium was sterilized at 120° C. for 10 minute by autoclaving.

Example 9

(2) Extraction of Crude Organic Substances from *Thalassiosira pseudonana* and Preparation of Hydrolysate Thereof The alga bodies in 1.8 L of the culture medium of Examples 9 (1) were precipitated by centrifugation, 50 mL of methanol:chloroform=2:1 were added to the precipitates, and the following extraction procedure was repeated three times. First, the alga bodies were suspended in 50 mL of methanol:chloroform=2:1, and left to stand overnight for extraction, and then the solid matters were removed by filtration to collect the extract. Then, the obtained extract was concentrated and suspended in 40 mL of hot water, 500 U of a lipase (L1754, Sigma) was added to the suspension, and the reaction was allowed to proceed at 42° C. for 18 hours. Aliphatic acid concentration and glycerol concentration of the reaction mixture were measured, and it was used as a carbon source of amino acid fermentation.

Example 9

(3) L-Lysine Production Culture Using Fat-and-Oil Hydrolysate Derived from *Thalassiosira pseudonana* as the Carbon Source The glycerol stocks of the *Escherichia coli* WC196LC/pCABD2 strain were thawed, 100 µL of each was uniformly applied to an L-plate containing 25 mg/L of streptomycin, and culture was performed at 37° C. for 20 hours. The cells in an amount of about 1/40 of the cells obtained on one plate were inoculated in 4 mL of the fermentation medium described below containing 25 mg/L of streptomycin, which was contained in a large diameter test tube, and cultured at 37° C. for 24 hours on a reciprocally shaking culture apparatus. To a hydrolyzed solution of each of the samples derived from the alga obtained in Example 9 (2) serving as the carbon source was added Tween 80 at a concentration of 2%, and the mixture was adjusted to pH 7.0 with 3 N KOH, autoclaved at 120° C. for 20 minutes, and used as the carbon source solution. The medium composition used for the culture is shown below. The component of Group A was the carbon source, and the total of the measured aliphatic acid concentration and glycerol concentration is indicated.

L-Lysine Production Medium for *Escherichia* Bacteria:
Group A:
Hydrolysate of crude extract derived from alga, 1.09 g/L (aliphatic acid concentration+glycerol concentration)
Group B:

| | |
|---|---|
| $(NH_4)_2SO_4$ | 24 g/L |
| $KH_2PO_4$ | 1.0 g/L |
| $FeSO_4 \cdot 7H_2O$ | 0.01 g/L |
| $MnSO_4 \cdot 4H_2O$ | 0.01 g/L |
| Yeast extract | 2.0 g/L |

Group C:

| | |
|---|---|
| Calcium carbonate | 30 g/L |

The components of Groups A and B were sterilized by autoclaving at 115° C. for 10 minutes, and the component of Group C was subjected to hot air sterilization at 180° C. for 3 hours. After the components of the three groups were cooled to room temperature, they were mixed, and an $MgSO_4 \cdot 7H_2O$ solution was added to the mixture at a final concentration of 1 g/L.

After completion of the culture, the L-lysine amount in the culture supernatant was measured with a Biotech Analyzer AS310 (Sakura Seiki). The degree of growth in this medium was determined by measuring the live cell count. The averages of the results of the culture performed in flasks in duplicate are shown in Table 9. The L-lysine concentration obtained by using only a 0.5% solution of the surfactant Tween 80 as the carbon source as a control was of the same as the L-lysine originally present in the medium, and thus L-lysine production was not observed. On the other hand, when the hydrolysate of the crude extract derived from *Thalassiosira pseudonana* was used, favorable L-lysine production was observed.

TABLE 9

| Carbon source | Culture time (h) | Live cell count ($\times 10^8$) | L-Lysine concentration (g/L) |
|---|---|---|---|
| 0.5% Tween 80 | 20 | 4.2 | 0.21 |
| Hydrolysate of crude extract derived from alga (1.09 g/L) + 0.5% Tween 80 | 20 | 4.1 | 0.81 |

Explanation of Sequence Listing:
SEQ ID NO: 1: Nucleotide sequence of LipA gene derived from *Bacillus subtilis*
SEQ ID NO: 2: Amino acid sequence of LipA derived from *Bacillus subtilis*
SEQ ID NO: 3: Nucleotide sequence of LipA gene derived from *Burkholderia glumae*
SEQ ID NO: 4: Amino acid sequence of LipA derived from *Burkholderia glumae*
SEQ ID NO: 5: Nucleotide sequence of LipA gene derived from *Pseudomonas eruginosa*
SEQ ID NO: 6: Amino acid sequence of LipA derived from *Pseudomonas aeruginosa*
SEQ ID NO: 7: Nucleotide sequence of lipase gene derived from *Staphylococcus aureus*
SEQ ID NO: 8: Amino acid sequence of lipase derived from *Staphylococcus aureus*
SEQ ID NO: 9: Nucleotide sequence of lipase gene derived from *Candida Antarctica*
SEQ ID NO: 10: Amino acid sequence of lipase derived from *Candida Antarctica*
SEQ ID NO: 11: Nucleotide sequence of lipase gene lip1 derived from *Candida rugosa*
SEQ ID NO: 12: Amino acid sequence of lipase LIP1 derived from *Candida rugosa*
SEQ ID NO: 13: Nucleotide sequence of lipase gene lip2 derived from *Candida rugosa*
SEQ ID NO: 14: Amino acid sequence of lipase LIP2 derived from *Candida rugosa*
SEQ ID NO: 15: Nucleotide sequence of *Escherichia coli* transcription factor gene fadR
SEQ ID NO: 16: Primer for fadR amplification
SEQ ID NO: 17: Primer for fadR amplification

INDUSTRIAL APPLICABILITY

L-Amino acids can be efficiently produced. In particular, L-amino acids can be produced at lower cost by using a carbon source derived from microalgae.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid comprising:
A) culturing a bacterium able to produce an L-amino acid in a medium comprising a processed product of a microalga, and
B) collecting the L-amino acid from the medium or the bacterium;
wherein the processed product increases production and accumulation of the L-amino acid by the bacterium compared to when culturing is performed in a medium that does not comprise the processed product,
wherein the processed product is obtained by a method selected from the group consisting of:
(1) hydrolyzing a disruption product of a culture of the microalga,
(2) hydrolyzing an extract or a fractionation product of a disruption product of a culture of the microalga comprising a mixture of organic substances, and
(3) combinations thereof.

2. The method according to claim 1, wherein the processed product is selected from the group consisting of:
(1) a saccharification product of a disruption product of alga bodies of the microalga,
(2) a saccharification product of an extract or a fractionation product of a disruption product of alga bodies of the microalga, wherein the extract or fractionation product comprises starch, and
(3) combinations thereof.

3. The method according to claim 2, wherein the saccharification product is obtained from the reaction of a disruption product of alga bodies of the microalga or a fractionation product thereof comprising starch with an amylase.

4. The method according to claim 3, wherein the amylase is glucoamylase.

5. The method according to claim 1, wherein the processed product is selected from the group consisting of:
   (1) a hydrolysate of a disruption product of alga bodies of the microalga, wherein the disruption product comprises fats and oils,
   (2) a hydrolysate of an extract a fractionation product of a disruption product of alga bodies of the microalga, wherein the extract or fractionation product comprises fats and oils, and
   (3) combinations thereof.

6. The method according to claim 5, wherein the hydrolysate is obtained from the reaction of a disruption product of alga bodies of a microalga or a fractionation product thereof comprising fats and oils with a lipase.

7. The method according to claim 5, wherein the hydrolysate is subjected to an emulsification treatment.

8. The method according to claim 1, wherein the processed product of a microalga is obtained by disrupting the microalga at a high temperature.

9. The method according to claim 8, wherein the high temperature is 100° C. or higher.

10. The method according to claim 1, wherein the microalga belongs to the phylum Chlorophyta or Heterokontophyta.

11. The method according to claim 10, wherein the bacterium belongs to the class Chlorophyceae, Trebouxiophyceae, or Bacillariophyceae.

12. The method according to claim 1, wherein the microalga belongs to the class Chlorophyceae.

13. The method according to claim 1, wherein the bacterium belongs to the family Enterobacteriaceae or coryneform bacterium.

14. The method according to claim 13, wherein the bacterium is *Escherichia coli*.

15. The method according to claim 1, wherein the L-amino acid is selected from the group consisting of L-lysine, L-threonine, L-glutamic acid, and combinations thereof.

16. The method according to claim 14, wherein the L-amino acid is L-lysine; and the activity is increased of an enzyme selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl diaminopimelate deacylase, and combinations thereof; and/or the activity of lysine decarboxylase is attenuated.

17. The method according to claim 14, wherein the L-amino acid is L-threonine; and the activity is increased of an enzyme selected from the group consisting of aspartate semialdehyde dehydrogenase, and aspartokinase I encoded by the thr operon, homoserine kinase, aspartate aminotransferase, threonine synthase, and combinations thereof.

18. The method according to claim 14, wherein the L-amino acid is L-glutamic acid; and
   the activity is increased of an enzyme selected from the group consisting of glutamate dehydrogenase, citrate synthase, phosphoenolpyruvate carboxylase methyl citrate synthase, and combinations thereof; and/or the activity of α-ketoglutarate dehydrogenase is attenuated.

19. The method according to claim 1, wherein the processed product acts as a carbon source in the medium.

20. A method for producing an L-amino acid, which comprises:
   (a) culturing a microalga in a medium, resulting in a culture product,
   (b) processing the culture product by a method selected from the group consisting of disruption, extraction, fractionation, hydrolysis, and, combinations thereof, resulting in a processed product of the microalga,
   (c) culturing a bacterium which is able to produce the L-amino acid in a second medium comprising the processed product of the microalga, and
   (d) collecting the L-amino acid from the second medium or the bacterium;
wherein the processed product increases production and accumulation of the L-amino acid compared to when the culturing is performed in a medium that does not comprise the processed product,
   wherein the processed product is selected from the group consisting of:
   (1) a hydrolysate of the disruption product of the culture product,
   (2) a hydrolysate of the extract or the fractionation product of the disruption product of the culture product, and
   (3) combinations thereof.

21. The method according to claim 20, wherein the disruption is performed by a method selected from the group consisting of a high temperature treatment, an organic solvent treatment, a boiling treatment, a strong alkali treatment, and combinations thereof.

22. The method according to claim 20, wherein the step of processing the culture product comprises the production of starch, and the processed product is subjected to further hydrolyzation to saccharify it.

23. The method according to claim 22, wherein the step of the further hydrolyzation comprises reacting the processed product with an amylase.

24. The method according to claim 23, wherein the amylase is a glucoamylase.

25. The method according to claim 20, wherein the step of processing the culture product comprises the production of fats and oils, and the processed product is subjected to further hydrolyzation, resulting in a hydrolysate.

26. The method according to claim 25, wherein the step of further hydrolyzation comprises reacting the processed product with a lipase.

27. The method according to claim 25, wherein the hydrolysate is subjected to an emulsification treatment.

28. The method according to claim 20, wherein the microalga belongs to the phylum Chlorophyta or Heterokontophyta.

29. The method according to claim 28, wherein the microalga belongs to the class Chlorophyceae, Treboaxiophyceae, or Bacillariophyceae.

30. The method according to claim 29, wherein the microalga belongs to the class Chlorophyceae.

31. The method according to claim 20, wherein the bacterium belongs to the family Enterobacteriaceae or coryneform bacterium.

32. The method according to claim 31, wherein the bacterium is *Escherichia coli*.

* * * * *

SEQUENCE LISTING

```
<160> NUMBER OF SEQ ID NOS: 17

<210> SEQ ID NO 1
<211> LENGTH: 639
<212> TYPE: DNA
<213> ORGANISM: Bacillus subtilis
<220> FEATURE:
<221> NAME/KEY: CDS
<222> LOCATION: (1)..(639)

<400> SEQUENCE: 1 atg aaa ttt gta aaa aga agg atc att gca ctt gta aca att ttg atg      48
Met Lys Phe Val Lys Arg Arg Ile Ile Ala Leu Val Thr Ile Leu Met
1               5                   10                  15
```

| | | |
|---|---|---|
| ctg tct gtt aca tcg ctg ttt gcg ttg cag ccg tca gca aaa gcc gct<br>Leu Ser Val Thr Ser Leu Phe Ala Leu Gln Pro Ser Ala Lys Ala Ala<br>20                         25                     30 | | 96 |
| gaa cac aat cca gtc gtt atg gtt cac ggt att gga ggg gca tca ttc<br>Glu His Asn Pro Val Val Met Val His Gly Ile Gly Gly Ala Ser Phe<br>35                     40                    45 | | 144 |
| aat ttt gcg gga att aag agc tat ctc gta tct cag ggc tgg tcg cgg<br>Asn Phe Ala Gly Ile Lys Ser Tyr Leu Val Ser Gln Gly Trp Ser Arg<br>50                        55                    60 | | 192 |
| gac aag ctg tat gca gtt gat ttt tgg gac aag aca ggc aca aat tat<br>Asp Lys Leu Tyr Ala Val Asp Phe Trp Asp Lys Thr Gly Thr Asn Tyr<br>65                 70                    75                    80 | | 240 |
| aac aat gga ccg gta tta tca cga ttt gtg caa aag gtt tta gat gaa<br>Asn Asn Gly Pro Val Leu Ser Arg Phe Val Gln Lys Val Leu Asp Glu<br>85                     90                    95 | | 288 |
| acg ggt gcg aaa aaa gtg gat att gtc gct cac agc atg ggg ggc gcg<br>Thr Gly Ala Lys Lys Val Asp Ile Val Ala His Ser Met Gly Gly Ala<br>100                   105                 110 | | 336 |
| aac aca ctt tac tac ata aaa aat ctg gac ggc gga aat aaa gtt gca<br>Asn Thr Leu Tyr Tyr Ile Lys Asn Leu Asp Gly Gly Asn Lys Val Ala<br>115                   120                 125 | | 384 |
| aac gtc gtg acg gtt ggc ggc gcg aac cgt ttg acg aca ggc aag gcg<br>Asn Val Val Thr Val Gly Gly Ala Asn Arg Leu Thr Thr Gly Lys Ala<br>130                   135                 140 | | 432 |
| ctt ccg gga aca gat cca aat caa aag att tta tac aca tcc att tac<br>Leu Pro Gly Thr Asp Pro Asn Gln Lys Ile Leu Tyr Thr Ser Ile Tyr<br>145                   150                 155                 160 | | 480 |
| agc agt gcc gat atg att gtc atg aat tac tta tca aga tta gat ggt<br>Ser Ser Ala Asp Met Ile Val Met Asn Tyr Leu Ser Arg Leu Asp Gly<br>165                   170                 175 | | 528 |
| gct aga aac gtt caa atc cat ggc gtt gga cac atc ggc ctt ctg tac<br>Ala Arg Asn Val Gln Ile His Gly Val Gly His Ile Gly Leu Leu Tyr<br>180                   185                 190 | | 576 |
| agc agc caa gtc aac agc ctg att aaa gaa ggg ctg aac ggc ggg ggc<br>Ser Ser Gln Val Asn Ser Leu Ile Lys Glu Gly Leu Asn Gly Gly Gly<br>195                   200                 205 | | 624 |
| cag aat acg aat taa<br>Gln Asn Thr Asn<br>210 | | 639 |

```
<210> SEQ ID NO 2
<211> LENGTH: 212
<212> TYPE: PRT
<213> ORGANISM: Bacillus subtilis

<400> SEQUENCE: 2
```

Met Lys Phe Val Lys Arg Arg Ile Ile Ala Leu Val Thr Ile Leu Met
1                  5                  10                  15

Leu Ser Val Thr Ser Leu Phe Ala Leu Gln Pro Ser Ala Lys Ala Ala
                  20                  25                  30

Glu His Asn Pro Val Val Met Val His Gly Ile Gly Gly Ala Ser Phe
               35                  40                  45

Asn Phe Ala Gly Ile Lys Ser Tyr Leu Val Ser Gln Gly Trp Ser Arg
 50                  55                  60

Asp Lys Leu Tyr Ala Val Asp Phe Trp Asp Lys Thr Gly Thr Asn Tyr
65                  70                  75                  80

Asn Asn Gly Pro Val Leu Ser Arg Phe Val Gln Lys Val Leu Asp Glu
               85                  90                  95

Thr Gly Ala Lys Lys Val Asp Ile Val Ala His Ser Met Gly Gly Ala
              100                105               110

```
Asn Thr Leu Tyr Tyr Ile Lys Asn Leu Asp Gly Gly Asn Lys Val Ala
            115                 120                 125

Asn Val Val Thr Val Gly Gly Ala Asn Arg Leu Thr Thr Gly Lys Ala
        130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Arg Leu Asp Gly
                165                 170                 175

Ala Arg Asn Val Gln Ile His Gly Val Gly His Ile Gly Leu Leu Tyr
            180                 185                 190

Ser Ser Gln Val Asn Ser Leu Ile Lys Glu Gly Leu Asn Gly Gly Gly
        195                 200                 205

Gln Asn Thr Asn
    210

<210> SEQ ID NO 3
<211> LENGTH: 1077
<212> TYPE: DNA
<213> ORGANISM: Burkholderia glumae
<220> FEATURE:
<221> NAME/KEY: CDS

```
cac aac acc gac cag gac gcg ctc gcg gcg ctg cgc acg ctc acc acc      624
His Asn Thr Asp Gln Asp Ala Leu Ala Ala Leu Arg Thr Leu Thr Thr
            195                 200                 205 gcg cag acc gcc acc tac aac cgg aac ttc ccg agc gcg ggc ctg ggc      672
Ala Gln Thr Ala Thr Tyr Asn Arg Asn Phe Pro Ser Ala Gly Leu Gly
        210                 215                 220 gcg ccc ggt tcg tgc cag acg ggc gcc gcg acc gaa acc gtc ggc ggc      720
Ala Pro Gly Ser Cys Gln Thr Gly Ala Ala Thr Glu Thr Val Gly Gly
225                 230                 235                 240 agc cag cac ctg ctc tat tcg tgg ggc ggc acc gcg atc cag ccc acc      768
Ser Gln His Leu Leu Tyr Ser Trp Gly Gly Thr Ala Ile Gln Pro Thr
            245                 250                 255 tcc acc gtg ctc ggc gtg acc ggc gcg acc gac acc agc acc ggc acg      816
Ser Thr Val Leu Gly Val Thr Gly Ala Thr Asp Thr Ser Thr Gly Thr
        260                 265                 270 ctc gac gtc gcg aac gtg acc gac ccg tcc acg ctc gcg ctg ctc gcc      864
Leu Asp Val Ala Asn Val Thr Asp Pro Ser Thr Leu Ala Leu Leu Ala
    275                 280                 285 acc ggc gcg gtg atg atc aat cgc gcc tcg ggg cag aac gac ggg ctc      912
Thr Gly Ala Val Met Ile Asn Arg Ala Ser Gly Gln Asn Asp Gly Leu
290                 295                 300 gtc tcg cgc tgc agc tcg ctg ttc ggg cag gtg atc agc acc agc tac      960
Val Ser Arg Cys Ser Ser Leu Phe Gly Gln Val Ile Ser Thr Ser Tyr
305                 310                 315                 320 cac tgg aac cat ctc gac gag atc aac cag ctg ctc ggc gtg cgc ggc     1008
His Trp Asn His Leu Asp Glu Ile Asn Gln Leu Leu Gly Val Arg Gly
            325                 330                 335 gcc aac gcg gaa gat ccg gtc gcg gtg atc cgc acg cac gtg aac cgg     1056
Ala Asn Ala Glu Asp Pro Val Ala Val Ile Arg Thr His Val Asn Arg
        340                 345                 350 ctc aag ctg cag ggc gtg tga                                         1077
Leu Lys Leu Gln Gly Val
    355
```

<210> SEQ ID NO 4
<211> LENGTH: 358
<212> TYPE: PRT
<213> ORGANISM: Burkholderia glumae

<400> SEQUENCE: 4

```
Met Val Arg Ser Met Arg Ser Arg Val Ala Ala Arg Ala Val Ala Trp
1               5                   10                  15

Ala Leu Ala Val Met Pro Leu Ala Gly Ala Ala Gly Leu Thr Met Ala
            20                  25                  30

Ala Ser Pro Ala Ala Val Ala Ala Asp Thr Tyr Ala Ala Thr Arg Tyr
        35                  40                  45

Pro Val Ile Leu Val His Gly Leu Ala Gly Thr Asp Lys Phe Ala Asn
    50                  55                  60

Val Val Asp Tyr Trp Tyr Gly Ile Gln Ser Asp Leu Gln Ser His Gly
65                  70                  75                  80

Ala Lys Val Tyr Val Ala Asn Leu Ser Gly Phe Gln Ser Asp Asp Gly
                85                  90                  95

Pro Asn Gly Arg Gly Glu Gln Leu Leu Ala Tyr Val Lys Gln Val Leu
            100                 105                 110

Ala Ala Thr Gly Ala Thr Lys Val Asn Leu Ile Gly His Ser Gln Gly
        115                 120                 125

Gly Leu Thr Ser Arg Tyr Val Ala Ala Val Ala Pro Gln Leu Val Ala
    130                 135                 140
```

```
Ser Val Thr Thr Ile Gly Thr Pro His Arg Gly Ser Glu Phe Ala Asp
145                 150                 155                 160

Phe Val Gln Asp Val Leu Lys Thr Asp Pro Thr Gly Leu Ser Ser Thr
                165                 170                 175

Val Ile Ala Ala Phe Val Asn Val Phe Gly Thr Leu Val Ser Ser Ser
            180                 185                 190

His Asn Thr Asp Gln Asp Ala Leu Ala Ala Leu Arg Thr Leu Thr Thr
        195                 200                 205

Ala Gln Thr Ala Thr Tyr Asn Arg Asn Phe Pro Ser Ala Gly Leu Gly
    210                 215                 220

Ala Pro Gly Ser Cys Gln Thr Gly Ala Ala Thr Glu Thr Val Gly Gly
225                 230                 235                 240

Ser Gln His Leu Leu Tyr Ser Trp Gly Gly Thr Ala Ile Gln Pro Thr
                245                 250                 255

Ser Thr Val Leu Gly Val Thr Gly Ala Thr Asp Thr Ser Thr Gly Thr
            260                 265                 270

Leu Asp Val Ala Asn Val Thr Asp Pro Ser Thr Leu Ala Leu Leu Ala
        275                 280                 285

Thr Gly Ala Val Met Ile Asn Arg Ala Ser Gly Gln Asn Asp Gly Leu
    290                 295                 300

Val Ser Arg Cys Ser Ser Leu Phe Gly Gln Val Ile Ser Thr Ser Tyr
305                 310                 315                 320

His Trp Asn His Leu Asp Glu Ile Asn Gln Leu Leu Gly Val Arg Gly
                325                 330                 335

Ala Asn Ala Glu Asp Pro Val Ala Val Ile Arg Thr His Val Asn Arg
            340                 345                 350

Leu Lys Leu Gln Gly Val
        355

<210> SEQ ID NO 5
<211> LENGTH: 936
<212> TYPE: DNA
<213> ORGANISM: Pseudomonas aeruginosa
<220> FEATURE:
<221> NAME/KEY: CDS
<222> LOCATION: (1)..(936)

<400> SEQUENCE: 5 atg aag aag aag tct ctg ctc ccc ctc ggc ctg gcc atc ggc ctc gcc        48
Met Lys Lys Lys Ser Leu Leu Pro Leu Gly Leu Ala Ile Gly Leu Ala
1               5                   10                  15 tct ctc gct gcc agc cct ctg atc cag gcc agc acc tac acc cag acc        96
Ser Leu Ala Ala Ser Pro Leu Ile Gln Ala Ser Thr Tyr Thr Gln Thr
            20                  25                  30 aaa tac ccc atc gtg ctg gcc cac ggc atg ctc ggc ttc gac aac atc       144
Lys Tyr Pro Ile Val Leu Ala His Gly Met Leu Gly Phe Asp Asn Ile
        35                  40                  45 ctc ggg gtc gac tac tgg ttc ggc att ccc agc gcc ttg cgc cgt gac       192
Leu Gly Val Asp Tyr Trp Phe Gly Ile Pro Ser Ala Leu Arg Arg Asp
    50                  55                  60 ggt gcc cag gtc tac gtc acc gaa gtc agc cag ttg gac acc tcg gaa       240
Gly Ala Gln Val Tyr Val Thr Glu Val Ser Gln Leu Asp Thr Ser Glu
65                  70                  75                  80 gtc cgc ggc gag cag ttg ctg caa cag gtg gag gaa atc gtc gcc ctc       288
Val Arg Gly Glu Gln Leu Leu Gln Gln Val Glu Glu Ile Val Ala Leu
                85                  90                  95 agc ggc cag ccc aag gtc aac ctg atc ggc cac agc cac ggc ggg ccg       336
Ser Gly Gln Pro Lys Val Asn Leu Ile Gly His Ser His Gly Gly Pro
            100                 105                 110
```

```
acc atc cgc tac gtc gcc gcc gta cgt ccc gac ctg atc gct tcc gcc    384
Thr Ile Arg Tyr Val Ala Ala Val Arg Pro Asp Leu Ile Ala Ser Ala
        115                 120                 125 acc agc gtc ggc gcc ccg cac aag ggt tcg gac acc gcc gac ttc ctg    432
Thr Ser Val Gly Ala Pro His Lys Gly Ser Asp Thr Ala Asp Phe Leu
130                 135                 140 cgc cag atc cca ccg ggt tcg gcc ggc gag gca atc ctc tcc ggg ctg    480
Arg Gln Ile Pro Pro Gly Ser Ala Gly Glu Ala Ile Leu Ser Gly Leu
145                 150                 155                 160 gtc aac agc ctc ggc gcg ctg atc agc ttc ctt tcc agc ggc agc acc    528
Val Asn Ser Leu Gly Ala Leu Ile Ser Phe Leu Ser Ser Gly Ser Thr
                165                 170                 175 ggt acg cag aat tca ctg ggc tcg ctg gag tcg ctg aac agc gag ggg    576
Gly Thr Gln Asn Ser Leu Gly Ser Leu Glu Ser Leu Asn Ser Glu Gly
            180                 185                 190 gcc gcg cgc ttc aac gcc aag tac ccg cag ggc gtc ccc acc tcg gcc    624
Ala Ala Arg Phe Asn Ala Lys Tyr Pro Gln Gly Val Pro Thr Ser Ala
        195                 200                 205 tgc ggc gag ggc gcc tac aag gtc aac ggc gtg agc tat tac tcc tgg    672
Cys Gly Glu Gly Ala Tyr Lys Val Asn Gly Val Ser Tyr Tyr Ser Trp
    210                 215                 220 agc ggt tcc tcg ccg ctg acc aac ttc ctc gat ccg agc gac gcc ttc    720
Ser Gly Ser Ser Pro Leu Thr Asn Phe Leu Asp Pro Ser Asp Ala Phe
225                 230                 235                 240 ctc ggc gcc tcg tcg ctg acc ttc aag aac ggc acc gcc aac gac ggc    768
Leu Gly Ala Ser Ser Leu Thr Phe Lys Asn Gly Thr Ala Asn Asp Gly
                245                 250                 255 ctg gtc ggc acc tgc agt tcg cac ctg ggc atg gtg atc cgc gac aac    816
Leu Val Gly Thr Cys Ser Ser His Leu Gly Met Val Ile Arg Asp Asn
            260                 265                 270 tac cgg atg aac cac ctg gac gag gtg aac cag gtc ttc ggc ctc acc    864
Tyr Arg Met Asn His Leu Asp Glu Val Asn Gln Val Phe Gly Leu Thr
        275                 280                 285 agc ctg ttc gag acc agc ccg gtc agc gtc tac cgc cag cac gcc aac    912
Ser Leu Phe Glu Thr Ser Pro Val Ser Val Tyr Arg Gln His Ala Asn
    290                 295                 300 cgc ctg aag aac gcc agc ctg tag                                    936
Arg Leu Lys Asn Ala Ser Leu
305                 310

<210> SEQ ID NO 6
<211> LENGTH: 311
<212> TYPE: PRT
<213> ORGANISM: Pseudomonas aeruginosa

<400> SEQUENCE: 6

Met Lys Lys Lys Ser Leu Leu Pro Leu Gly Leu Ala Ile Gly Leu Ala
1               5                   10                  15

Ser Leu Ala Ala Ser Pro Leu Ile Gln Ala Ser Thr Tyr Thr Gln Thr
            20                  25                  30

Lys Tyr Pro Ile Val Leu Ala His Gly Met Leu Gly Phe Asp Asn Ile
        35                  40                  45

Leu Gly Val Asp Tyr Trp Phe Gly Ile Pro Ser Ala Leu Arg Arg Asp
    50                  55                  60

Gly Ala Gln Val Tyr Val Thr Glu Val Ser Gln Leu Asp Thr Ser Glu
65                  70                  75                  80

Val Arg Gly Glu Gln Leu Leu Gln Gln Val Glu Glu Ile Val Ala Leu
                85                  90                  95

Ser Gly Gln Pro Lys Val Asn Leu Ile Gly His Ser His Gly Gly Pro
            100                 105                 110
```

```
Thr Ile Arg Tyr Val Ala Ala Val Arg Pro Asp Leu Ile Ala Ser Ala
        115                 120                 125

Thr Ser Val Gly Ala Pro His Lys Gly Ser Asp Thr Ala Asp Phe Leu
    130                 135                 140

Arg Gln Ile Pro Pro Gly Ser Ala Gly Glu Ala Ile Leu Ser Gly Leu
145                 150                 155                 160

Val Asn Ser Leu Gly Ala Leu Ile Ser Phe Leu Ser Ser Gly Ser Thr
                165                 170                 175

Gly Thr Gln Asn Ser Leu Gly Ser Leu Glu Ser Leu Asn Ser Glu Gly
            180                 185                 190

Ala Ala Arg Phe Asn Ala Lys Tyr Pro Gln Gly Val Pro Thr Ser Ala
        195                 200                 205

Cys Gly Glu Gly Ala Tyr Lys Val Asn Gly Val Ser Tyr Tyr Ser Trp
    210                 215                 220

Ser Gly Ser Ser Pro Leu Thr Asn Phe Leu Asp Pro Ser Asp Ala Phe
225                 230                 235                 240

Leu Gly Ala Ser Ser Leu Thr Phe Lys Asn Gly Thr Ala Asn Asp Gly
                245                 250                 255

Leu Val Gly Thr Cys Ser Ser His Leu Gly Met Val Ile Arg Asp Asn
            260                 265                 270

Tyr Arg Met Asn His Leu Asp Glu Val Asn Gln Val Phe Gly Leu Thr
        275                 280                 285

Ser Leu Phe Glu Thr Ser Pro Val Ser Val Tyr Arg Gln His Ala Asn
    290                 295                 300

Arg Leu Lys Asn Ala Ser Leu
305                 310

<210> SEQ ID NO 7
<211> LENGTH: 2073
<212> TYPE: DNA
<213> ORGANISM: Staphylococcus aureus
<220> FEATURE:
<221> NAME/KEY: CDS
<222> LOCATION: (1)..(2073)

<400> SEQUENCE: 7 atg tta aga gga caa gaa gaa aga aag tat agt att aga aag tat tca        48
Met Leu Arg Gly Gln Glu Glu Arg Lys Tyr Ser Ile Arg Lys Tyr Ser
1               5                   10                  15 ata ggc gtg gtg tca gtg tta gcg gct aca atg ttt gtt gtg tca tca        96
Ile Gly Val Val Ser Val Leu Ala Ala Thr Met Phe Val Val Ser Ser
                20                  25                  30 cat gaa gca caa gcc tcg gaa aaa aca tca act aat gca gcg gca caa       144
His Glu Ala Gln Ala Ser Glu Lys Thr Ser Thr Asn Ala Ala Ala Gln
            35                  40                  45 aaa gaa aca cta aat caa ccg gga gaa caa ggg aat gcg ata acg tca       192
Lys Glu Thr Leu Asn Gln Pro Gly Glu Gln Gly Asn Ala Ile Thr Ser
        50                  55                  60 cat caa atg cag tca gga aag caa tta gac gat atg cat aaa gag aat       240
His Gln Met Gln Ser Gly Lys Gln Leu Asp Asp Met His Lys Glu Asn
65                  70                  75                  80 ggt aaa agt gga aca gtg aca gaa ggt aaa gat acg ctt caa tca tcg       288
Gly Lys Ser Gly Thr Val Thr Glu Gly Lys Asp Thr Leu Gln Ser Ser
                85                  90                  95 aag cat caa tca aca caa aat agt aaa aca atc aga acg caa aat gat       336
Lys His Gln Ser Thr Gln Asn Ser Lys Thr Ile Arg Thr Gln Asn Asp
            100                 105                 110
```

```
aat caa gta aag caa gat tct gaa cga caa ggt tct aaa cag tca cac    384
Asn Gln Val Lys Gln Asp Ser Glu Arg Gln Gly Ser Lys Gln Ser His
        115                 120                 125 caa aat aat gcg act aat aat act gaa cgt caa aat gat cag gtt caa    432
Gln Asn Asn Ala Thr Asn Asn Thr Glu Arg Gln Asn Asp Gln Val Gln
130                 135                 140 aat acc cat cat gct gaa cgt aat gga tca caa tcg aca acg tca caa    480
Asn Thr His His Ala Glu Arg Asn Gly Ser Gln Ser Thr Thr Ser Gln
145                 150                 155                 160 tcg aat gat gtt gat aaa tca caa cca tcc att ccg gca caa aag gta    528
Ser Asn Asp Val Asp Lys Ser Gln Pro Ser Ile Pro Ala Gln Lys Val
                165                 170                 175 ata ccc aat cat gat aaa gca gca cca act tca act aca ccc ccg tct    576
Ile Pro Asn His Asp Lys Ala Ala Pro Thr Ser Thr Thr Pro Pro Ser
            180                 185                 190 aat gat aaa act gca cct aaa tca aca aaa gca caa gat gca acc acg    624
Asn Asp Lys Thr Ala Pro Lys Ser Thr Lys Ala Gln Asp Ala Thr Thr
        195                 200                 205 gac aaa cat cca aat caa caa gat aca cat caa cct gcg cat caa atc    672
Asp Lys His Pro Asn Gln Gln Asp Thr His Gln Pro Ala His Gln Ile
210                 215                 220 ata gat gca aag caa gat gat act gtt cgc caa agt gaa cag aaa cca    720
Ile Asp Ala Lys Gln Asp Asp Thr Val Arg Gln Ser Glu Gln Lys Pro
225                 230                 235                 240 caa gtt ggc gat tta agt aaa cat atc gat ggt caa aat tcc cca gag    768
Gln Val Gly Asp Leu Ser Lys His Ile Asp Gly Gln Asn Ser Pro Glu
                245                 250                 255 aaa ccg aca gat aaa aat act gat aat aaa caa cta atc aaa gat gcg    816
Lys Pro Thr Asp Lys Asn Thr Asp Asn Lys Gln Leu Ile Lys Asp Ala
            260                 265                 270 ctt caa gcg cct aaa aca cgt tcg act aca aat gca gca gca gat gct    864
Leu Gln Ala Pro Lys Thr Arg Ser Thr Thr Asn Ala Ala Ala Asp Ala
        275                 280                 285 aaa aag gtt cga cca ctt aaa gcg aat caa gta caa cca ctt aac aaa    912
Lys Lys Val Arg Pro Leu Lys Ala Asn Gln Val Gln Pro Leu Asn Lys
290                 295                 300 tat cca gtt gtt ttt gta cat gga ttt tta gga tta gta ggc gat aat    960
Tyr Pro Val Val Phe Val His Gly Phe Leu Gly Leu Val Gly Asp Asn
305                 310                 315                 320 gca cct gct tta tat cca aat tat tgg ggt gga aat aaa ttt aaa gtt   1008
Ala Pro Ala Leu Tyr Pro Asn Tyr Trp Gly Gly Asn Lys Phe Lys Val
                325                 330                 335 atc gaa gaa ttg aga aag caa ggc tat aat gta cat caa gca agt gta   1056
Ile Glu Glu Leu Arg Lys Gln Gly Tyr Asn Val His Gln Ala Ser Val
            340                 345                 350 agt gca ttt ggt agt aac tat gat cgc gct gta gaa ctt tat tat tac   1104
Ser Ala Phe Gly Ser Asn Tyr Asp Arg Ala Val Glu Leu Tyr Tyr Tyr
        355                 360                 365 att aaa ggt ggt cgc gta gat tat ggc gca gca cat gca gct aaa tac   1152
Ile Lys Gly Gly Arg Val Asp Tyr Gly Ala Ala His Ala Ala Lys Tyr
370                 375                 380 gga cat gag cgc tat ggt aag act tat aaa gga atc atg cct aat tgg   1200
Gly His Glu Arg Tyr Gly Lys Thr Tyr Lys Gly Ile Met Pro Asn Trp
385                 390                 395                 400 gaa cct ggt aaa aag gta cat ctt gta ggg cat agt atg ggt ggt caa   1248
Glu Pro Gly Lys Lys Val His Leu Val Gly His Ser Met Gly Gly Gln
                405                 410                 415
```

```
aca att cgt tta atg gaa gag ttt tta aga aat ggt aac aaa gaa gaa      1296
Thr Ile Arg Leu Met Glu Glu Phe Leu Arg Asn Gly Asn Lys Glu Glu
            420                 425                 430 att gcc tat cat aaa gcg cat gga gaa ata tca cca tta ttc act          1344
Ile Ala Tyr His Lys Ala His Gly Gly Glu Ile Ser Pro Leu Phe Thr
    435                 440                 445 ggt ggt cat aac aat atg gtt gca tca atc aca aca tta gca aca cca      1392
Gly Gly His Asn Asn Met Val Ala Ser Ile Thr Thr Leu Ala Thr Pro
450                 455                 460 cat aat ggt tca caa gca gct gat aag ttt gga aat aca gaa gct gtt      1440
His Asn Gly Ser Gln Ala Ala Asp Lys Phe Gly Asn Thr Glu Ala Val
465                 470                 475                 480 aga aaa atc atg ttc gct tta aat cga ttt atg ggt aac aag tat tcg      1488
Arg Lys Ile Met Phe Ala Leu Asn Arg Phe Met Gly Asn Lys Tyr Ser
                485                 490                 495 aat atc gat tta gga tta acg caa tgg ggc ttt aaa caa tta cca aat      1536
Asn Ile Asp Leu Gly Leu Thr Gln Trp Gly Phe Lys Gln Leu Pro Asn
            500                 505                 510 gag agt tac att gac tat ata aaa cgc gtt agt aaa agc aaa att tgg      1584
Glu Ser Tyr Ile Asp Tyr Ile Lys Arg Val Ser Lys Ser Lys Ile Trp
        515                 520                 525 aca tca gac gac aat gct gcc tat gat tta acg tta gat ggc tct gca      1632
Thr Ser Asp Asp Asn Ala Ala Tyr Asp Leu Thr Leu Asp Gly Ser Ala
    530                 535                 540 aaa ttg aac aac atg aca agt atg aat cct aat att acg tat acg act      1680
Lys Leu Asn Asn Met Thr Ser Met Asn Pro Asn Ile Thr Tyr Thr Thr
545                 550                 555                 560 tat aca ggt gta tca tct cat act ggt cca tta ggt tat gaa aat cct      1728
Tyr Thr Gly Val Ser Ser His Thr Gly Pro Leu Gly Tyr Glu Asn Pro
                565                 570                 575 gat tta ggt aca ttt ttc tta atg gct aca acg agt aga att att ggt      1776
Asp Leu Gly Thr Phe Phe Leu Met Ala Thr Thr Ser Arg Ile Ile Gly
            580                 585                 590 cat gat gca aga gaa gaa tgg cgt aaa aat gat ggt gtc gta cca gtg      1824
His Asp Ala Arg Glu Glu Trp Arg Lys Asn Asp Gly Val Val Pro Val
        595                 600                 605 att tcg tca tta cat ccg tcc aat caa cca ttt gtt aat gtt acg aat      1872
Ile Ser Ser Leu His Pro Ser Asn Gln Pro Phe Val Asn Val Thr Asn
    610                 615                 620 gat gaa cct gcc aca cgc aga ggt atc tgg caa gtt aaa cca atc ata      1920
Asp Glu Pro Ala Thr Arg Arg Gly Ile Trp Gln Val Lys Pro Ile Ile
625                 630                 635                 640 caa gga tgg gat cat gtc gat ttt atc ggt gtg gac ttc ctg gat ttc      1968
Gln Gly Trp Asp His Val Asp Phe Ile Gly Val Asp Phe Leu Asp Phe
                645                 650                 655 aaa cgt aaa ggt gca gaa ctt gcc aac ttc tat aca ggt att tat aat      2016
Lys Arg Lys Gly Ala Glu Leu Ala Asn Phe Tyr Thr Gly Ile Ile Asn
            660                 665                 670 gac ttg ttg cgt gtt gaa gcg act gaa agt aaa gga aca caa ttg aaa      2064
Asp Leu Leu Arg Val Glu Ala Thr Glu Ser Lys Gly Thr Gln Leu Lys
        675                 680                 685 gca agt taa                                                          2073
Ala Ser
    690

<210> SEQ ID NO 8
<211> LENGTH: 690
<212> TYPE: PRT
<213> ORGANISM: Staphylococcus aureus
```

<400> SEQUENCE: 8

| | | | | | | | | | | | | | | |
|---|---|---|---|---|---|---|---|---|---|---|---|---|---|---|
| Met | Leu | Arg | Gly | Gln | Glu | Glu | Arg | Lys | Tyr | Ser | Ile | Arg | Lys | Tyr | Ser |
| 1 | | | | 5 | | | | | 10 | | | | | 15 | |
| Ile | Gly | Val | Val | Ser | Val | Leu | Ala | Ala | Thr | Met | Phe | Val | Val | Ser | Ser |
| | | | 20 | | | | | 25 | | | | | 30 | | |
| His | Glu | Ala | Gln | Ala | Ser | Glu | Lys | Thr | Ser | Thr | Asn | Ala | Ala | Ala | Gln |
| | | | | 35 | | | | | 40 | | | | 45 | | |
| Lys | Glu | Thr | Leu | Asn | Gln | Pro | Gly | Glu | Gln | Gly | Asn | Ala | Ile | Thr | Ser |
| | 50 | | | | | 55 | | | | | 60 | | | | |
| His | Gln | Met | Gln | Ser | Gly | Lys | Gln | Leu | Asp | Asp | Met | His | Lys | Glu | Asn |
| 65 | | | | | 70 | | | | | 75 | | | | | 80 |
| Gly | Lys | Ser | Gly | Thr | Val | Thr | Glu | Gly | Lys | Asp | Thr | Leu | Gln | Ser | Ser |
| | | | | 85 | | | | | 90 | | | | | 95 | |
| Lys | His | Gln | Ser | Thr | Gln | Asn | Ser | Lys | Thr | Ile | Arg | Thr | Gln | Asn | Asp |
| | | | 100 | | | | | 105 | | | | | 110 | | |
| Asn | Gln | Val | Lys | Gln | Asp | Ser | Glu | Arg | Gln | Gly | Ser | Lys | Gln | Ser | His |
| | | | | 115 | | | | | 120 | | | | 125 | | |
| Gln | Asn | Asn | Ala | Thr | Asn | Thr | Glu | Arg | Gln | Asn | Asp | Gln | Val | Gln |
| | 130 | | | | | 135 | | | | | 140 | | | | |
| Asn | Thr | His | His | Ala | Glu | Arg | Asn | Gly | Ser | Gln | Ser | Thr | Thr | Ser | Gln |
| 145 | | | | | 150 | | | | | 155 | | | | | 160 |
| Ser | Asn | Asp | Val | Asp | Lys | Ser | Gln | Pro | Ser | Ile | Pro | Ala | Gln | Lys | Val |
| | | | | 165 | | | | | 170 | | | | | 175 | |
| Ile | Pro | Asn | His | Asp | Lys | Ala | Ala | Pro | Thr | Ser | Thr | Thr | Pro | Pro | Ser |
| | | | 180 | | | | | 185 | | | | | 190 | | |
| Asn | Asp | Lys | Thr | Ala | Pro | Lys | Ser | Thr | Lys | Ala | Gln | Asp | Ala | Thr | Thr |
| | | | 195 | | | | | 200 | | | | | 205 | | |
| Asp | Lys | His | Pro | Asn | Gln | Gln | Asp | Thr | His | Gln | Pro | Ala | His | Gln | Ile |
| | 210 | | | | | 215 | | | | | 220 | | | | |
| Ile | Asp | Ala | Lys | Gln | Asp | Asp | Thr | Val | Arg | Gln | Ser | Glu | Gln | Lys | Pro |
| 225 | | | | | 230 | | | | | 235 | | | | | 240 |
| Gln | Val | Gly | Asp | Leu | Ser | Lys | His | Ile | Asp | Gly | Gln | Asn | Ser | Pro | Glu |
| | | | | 245 | | | | | 250 | | | | | 255 | |
| Lys | Pro | Thr | Asp | Lys | Asn | Thr | Asp | Asn | Lys | Gln | Leu | Ile | Lys | Asp | Ala |
| | | | 260 | | | | | 265 | | | | | 270 | | |
| Leu | Gln | Ala | Pro | Lys | Thr | Arg | Ser | Thr | Thr | Asn | Ala | Ala | Ala | Asp | Ala |
| | | | | 275 | | | | | 280 | | | | | 285 | |
| Lys | Lys | Val | Arg | Pro | Leu | Lys | Ala | Asn | Gln | Val | Gln | Pro | Leu | Asn | Lys |
| | 290 | | | | | 295 | | | | | 300 | | | | |
| Tyr | Pro | Val | Val | Phe | Val | His | Gly | Phe | Leu | Gly | Leu | Val | Gly | Asp | Asn |
| 305 | | | | | 310 | | | | | 315 | | | | | 320 |
| Ala | Pro | Ala | Leu | Tyr | Pro | Asn | Tyr | Trp | Gly | Gly | Asn | Lys | Phe | Lys | Val |
| | | | | 325 | | | | | 330 | | | | | 335 | |
| Ile | Glu | Glu | Leu | Arg | Lys | Gln | Gly | Tyr | Asn | Val | His | Gln | Ala | Ser | Val |
| | | | 340 | | | | | 345 | | | | | 350 | | |
| Ser | Ala | Phe | Gly | Ser | Asn | Tyr | Asp | Arg | Ala | Val | Glu | Leu | Tyr | Tyr | Tyr |
| | | | 355 | | | | | 360 | | | | | 365 | | |
| Ile | Lys | Gly | Gly | Arg | Val | Asp | Tyr | Gly | Ala | Ala | His | Ala | Ala | Lys | Tyr |
| | 370 | | | | | 375 | | | | | 380 | | | | |
| Gly | His | Glu | Arg | Tyr | Gly | Lys | Thr | Tyr | Lys | Gly | Ile | Met | Pro | Asn | Trp |
| 385 | | | | | 390 | | | | | 395 | | | | | 400 |
| Glu | Pro | Gly | Lys | Lys | Val | His | Leu | Val | Gly | His | Ser | Met | Gly | Gly | Gln |
| | | | | 405 | | | | | 410 | | | | | 415 | |

```
Thr Ile Arg Leu Met Glu Glu Phe Leu Arg Asn Gly Asn Lys Glu Glu
            420                 425                 430

Ile Ala Tyr His Lys Ala His Gly Glu Ile Ser Pro Leu Phe Thr
            435                 440                 445

Gly Gly His Asn Asn Met Val Ala Ser Ile Thr Thr Leu Ala Thr Pro
450                 455                 460

His Asn Gly Ser Gln Ala Ala Asp Lys Phe Gly Asn Thr Glu Ala Val
465                 470                 475                 480

Arg Lys Ile Met Phe Ala Leu Asn Arg Phe Met Gly Asn Lys Tyr Ser
                    485                 490                 495

Asn Ile Asp Leu Gly Leu Thr Gln Trp Gly Phe Lys Gln Leu Pro Asn
            500                 505                 510

Glu Ser Tyr Ile Asp Tyr Ile Lys Arg Val Ser Lys Ser Lys Ile Trp
            515                 520                 525

Thr Ser Asp Asp Asn Ala Ala Tyr Asp Leu Thr Leu Asp Gly Ser Ala
530                 535                 540

Lys Leu Asn Asn Met Thr Ser Met Asn Pro Asn Ile Thr Tyr Thr Thr
545                 550                 555                 560

Tyr Thr Gly Val Ser Ser His Thr Gly Pro Leu Gly Tyr Glu Asn Pro
                    565                 570                 575

Asp Leu Gly Thr Phe Phe Leu Met Ala Thr Thr Ser Arg Ile Ile Gly
            580                 585                 590

His Asp Ala Arg Glu Glu Trp Arg Lys Asn Asp Gly Val Val Pro Val
            595                 600                 605

Ile Ser Ser Leu His Pro Ser Asn Gln Pro Phe Val Asn Val Thr Asn
610                 615                 620

Asp Glu Pro Ala Thr Arg Arg Gly Ile Trp Gln Val Lys Pro Ile Ile
625                 630                 635                 640

Gln Gly Trp Asp His Val Asp Phe Ile Gly Val Asp Phe Leu Asp Phe
                    645                 650                 655

Lys Arg Lys Gly Ala Glu Leu Ala Asn Phe Tyr Thr Gly Ile Ile Asn
            660                 665                 670

Asp Leu Leu Arg Val Glu Ala Thr Glu Ser Lys Gly Thr Gln Leu Lys
            675                 680                 685

Ala Ser
690

<210> SEQ ID NO 9
<211> LENGTH: 1029
<212> TYPE: DNA
<213> ORGANISM: Candida antarctica
<220> FEATURE:
<221> NAME/KEY: CDS
<222> LOCATION: (1)..(1029)

<400> SEQUENCE: 9 atg aag cta ctc tct ctg acc ggt gtg gct ggt gtg ctt gcg act tgc     48
Met Lys Leu Leu Ser Leu Thr Gly Val Ala Gly Val Leu Ala Thr Cys
1               5                   10                  15 gtt gca gcc act cct ttg gtg aag cgt cta cct tcc ggt tcg gac cct     96
Val Ala Ala Thr Pro Leu Val Lys Arg Leu Pro Ser Gly Ser Asp Pro
                20                  25                  30 gcc ttt tcg cag ccc aag tcg gtg ctc gat gcg ggt ctg acc tgc cag    144
Ala Phe Ser Gln Pro Lys Ser Val Leu Asp Ala Gly Leu Thr Cys Gln
            35                  40                  45 ggt gct tcg cca tcc tcg gtc tcc aaa ccc atc ctt ctc gtc ccc gga    192
Gly Ala Ser Pro Ser Ser Val Ser Lys Pro Ile Leu Leu Val Pro Gly
50                  55                  60
```

| | | |
|---|---|---|
| acc ggc acc aca ggt cca cag tcg ttc gac tcg aac tgg atc ccc ctc<br>Thr Gly Thr Thr Gly Pro Gln Ser Phe Asp Ser Asn Trp Ile Pro Leu<br>65                               70                       75                     80 | | 240 |
| tca acg cag ttg ggt tac aca ccc tgc tgg atc tca ccc ccg ccg ttc<br>Ser Thr Gln Leu Gly Tyr Thr Pro Cys Trp Ile Ser Pro Pro Pro Phe<br>                   85                   90                  95 | | 288 |
| atg ctc aac gac acc cag gtc aac acg gag tac atg gtc aac gcc atc<br>Met Leu Asn Asp Thr Gln Val Asn Thr Glu Tyr Met Val Asn Ala Ile<br>                 100                 105               110 | | 336 |
| acc gcg ctc tac gct ggt tcg ggc aac aac aag ctt ccc gtg ctt acc<br>Thr Ala Leu Tyr Ala Gly Ser Gly Asn Asn Lys Leu Pro Val Leu Thr<br>    115                 120                 125 | | 384 |
| tgg tcc cag ggt ggt ctg gtt gca cag tgg ggt ctg acc ttc ttc ccc<br>Trp Ser Gln Gly Gly Leu Val Ala Gln Trp Gly Leu Thr Phe Phe Pro<br>130                           135                 140 | | 432 |
| agt atc agg tcc aag gtc gat cga ctt atg gcc ttt gcg ccc gac tac<br>Ser Ile Arg Ser Lys Val Asp Arg Leu Met Ala Phe Ala Pro Asp Tyr<br>145                     150                 155               160 | | 480 |
| aag ggc acc gtc ctc gcc ggc cct ctc gat gca ctc gcg gtt agt gca<br>Lys Gly Thr Val Leu Ala Gly Pro Leu Asp Ala Leu Ala Val Ser Ala<br>               165                 170               175 | | 528 |
| ccc tcc gta tgg cag caa acc acc ggt tcg gca ctc acc acc gca ctc<br>Pro Ser Val Trp Gln Gln Thr Thr Gly Ser Ala Leu Thr Thr Ala Leu<br>           180                 185               190 | | 576 |
| cga aac gca ggt ggt ctg acc cag atc gtg ccc acc acc aac ctc tac<br>Arg Asn Ala Gly Gly Leu Thr Gln Ile Val Pro Thr Thr Asn Leu Tyr<br>    195                 200                 205 | | 624 |
| tcg gcg acc gac gag atc gtt cag cct cag gtg tcc aac tcg cca ctc<br>Ser Ala Thr Asp Glu Ile Val Gln Pro Gln Val Ser Asn Ser Pro Leu<br>210                           215                 220 | | 672 |
| gac tca tcc tac ctc ttc aac gga aag aac gtc cag gca cag gcc gtg<br>Asp Ser Ser Tyr Leu Phe Asn Gly Lys Asn Val Gln Ala Gln Ala Val<br>225                     230                 235               240 | | 720 |
| tgt ggg ccg ctg ttc gtc atc gac cat gca ggc tcg ctc acc tcg cag<br>Cys Gly Pro Leu Phe Val Ile Asp His Ala Gly Ser Leu Thr Ser Gln<br>                   245                 250               255 | | 768 |
| ttc tcc tac gtc gtc ggt cga tcc gcc ctg cgc tcc acc acg ggc cag<br>Phe Ser Tyr Val Val Gly Arg Ser Ala Leu Arg Ser Thr Thr Gly Gln<br>           260                 265               270 | | 816 |
| gct cgt agt gca gac tat ggc att acg gac tgc aac cct ctt ccc gcc<br>Ala Arg Ser Ala Asp Tyr Gly Ile Thr Asp Cys Asn Pro Leu Pro Ala<br>    275                 280                 285 | | 864 |
| aat gat ctg act ccc gag caa aag gtc gcc gcg gct gcg ctc ctg gcg<br>Asn Asp Leu Thr Pro Glu Gln Lys Val Ala Ala Ala Ala Leu Leu Ala<br>290                           295                 300 | | 912 |
| ccg gca gct gca gcc atc gtg gcg ggt cca aag cag aac tgc gag ccc<br>Pro Ala Ala Ala Ala Ile Val Ala Gly Pro Lys Gln Asn Cys Glu Pro<br>305                     310                 315               320 | | 960 |
| gac ctc atg ccc tac gcc cgc ccc ttt gca gta ggc aaa agg acc tgc<br>Asp Leu Met Pro Tyr Ala Arg Pro Phe Ala Val Gly Lys Arg Thr Cys<br>                   325                 330               335 | | 1008 |
| tcc ggc atc gtc acc ccc tga<br>Ser Gly Ile Val Thr Pro<br>                 340 | | 1029 |

<210> SEQ ID NO 10
<211> LENGTH: 342
<212> TYPE: PRT
<213> ORGANISM: Candida antarctica

<400> SEQUENCE: 10

| | | | | | | | | | | | | | | | |
|---|---|---|---|---|---|---|---|---|---|---|---|---|---|---|---|
|Met|Lys|Leu|Leu|Ser|Leu|Thr|Gly|Val|Ala|Gly|Val|Leu|Ala|Thr|Cys|
|1| | | |5| | | | |10| | | | |15| |

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
                35                  40                  45

Gly Ala Ser Pro Ser Ser Val Ser Lys Pro Ile Leu Val Pro Gly
 50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Phe
             85                  90                  95

Met Leu Asn Asp Thr Gln Val Asn Thr Glu Tyr Met Val Asn Ala Ile
               100                 105                 110

Thr Ala Leu Tyr Ala Gly Ser Gly Asn Asn Lys Leu Pro Val Leu Thr
             115                 120                 125

Trp Ser Gln Gly Gly Leu Val Ala Gln Trp Gly Leu Thr Phe Phe Pro
130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
             180                 185                 190

Arg Asn Ala Gly Gly Leu Thr Gln Ile Val Pro Thr Thr Asn Leu Tyr
                195                 200                 205

Ser Ala Thr Asp Glu Ile Val Gln Pro Gln Val Ser Asn Ser Pro Leu
210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
             260                 265                 270

Ala Arg Ser Ala Asp Tyr Gly Ile Thr Asp Cys Asn Pro Leu Pro Ala
            275                 280                 285

Asn Asp Leu Thr Pro Glu Gln Lys Val Ala Ala Ala Leu Leu Ala
290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 11
<211> LENGTH: 1650
<212> TYPE: DNA
<213> ORGANISM: Candida rugosa
<220> FEATURE:
<221> NAME/KEY: CDS
<222> LOCATION: (1)..(1650)

-continued

<400> SEQUENCE: 11

```
atg gag ctc gct ctt gcg ctc ctg ctc att gcc tcg gtg gct gct gcc      48
Met Glu Leu Ala Leu Ala Leu Leu Leu Ile Ala Ser Val Ala Ala Ala
1               5                   10                  15 ccc acc gcc acg ctc gcc aac ggc gac acc atc acc ggt ctc aac gcc      96
Pro Thr Ala Thr Leu Ala Asn Gly Asp Thr Ile Thr Gly Leu Asn Ala
            20                  25                  30 atc atc aac gag gcg ttc ctc ggc att ccc ttt gcc gag ccg ccg gtg     144
Ile Ile Asn Glu Ala Phe Leu Gly Ile Pro Phe Ala Glu Pro Pro Val
        35                  40                  45 ggc aac ctc cgc ttc aag gac ccc gtg ccg tac tcc ggc tcg ctc gat     192
Gly Asn Leu Arg Phe Lys Asp Pro Val Pro Tyr Ser Gly Ser Leu Asp
    50                  55                  60 ggc cag aag ttc acg ctg tac ggc ccg ctg tgc atg cag cag aac ccc     240
Gly Gln Lys Phe Thr Leu Tyr Gly Pro Leu Cys Met Gln Gln Asn Pro
65                  70                  75                  80 gag ggc acc tac gag gag aac ctc ccc aag gca gcg ctc gac ttg gtg     288
Glu Gly Thr Tyr Glu Glu Asn Leu Pro Lys Ala Ala Leu Asp Leu Val
                85                  90                  95 atg cag tcc aag gtg ttt gag gcg gtg ctg ccg ctg agc gag gac tgt     336
Met Gln Ser Lys Val Phe Glu Ala Val Leu Pro Leu Ser Glu Asp Cys
            100                 105                 110 ctc acc atc aac gtg gtg cgg ccg ccg ggc acc aag gcg ggt gcc aac     384
Leu Thr Ile Asn Val Val Arg Pro Pro Gly Thr Lys Ala Gly Ala Asn
        115                 120                 125 ctc ccg gtg atg ctc tgg atc ttt ggc ggc ggg ttt gag gtg ggt ggc     432
Leu Pro Val Met Leu Trp Ile Phe Gly Gly Gly Phe Glu Val Gly Gly
    130                 135                 140 acc agc acc ttc cct ccc gcc cag atg atc acc aag agc att gcc atg     480
Thr Ser Thr Phe Pro Pro Ala Gln Met Ile Thr Lys Ser Ile Ala Met
145                 150                 155                 160 ggc aag ccc atc atc cac gtg agc gtc aac tac cgc gtg tcg tcg tgg     528
Gly Lys Pro Ile Ile His Val Ser Val Asn Tyr Arg Val Ser Ser Trp
                165                 170                 175 ggg ttc ttg gct ggc gac gag atc aag gcc gag ggc agt gcc aac gcc     576
Gly Phe Leu Ala Gly Asp Glu Ile Lys Ala Glu Gly Ser Ala Asn Ala
            180                 185                 190 ggt ttg aag gac cag cgc ttg ggc atg cag tgg gtg gcg gac aac att     624
Gly Leu Lys Asp Gln Arg Leu Gly Met Gln Trp Val Ala Asp Asn Ile
        195                 200                 205 gcg gcg ttt ggc ggc gac ccg acc aag gtg acc atc ttt ggc gag ctg     672
Ala Ala Phe Gly Gly Asp Pro Thr Lys Val Thr Ile Phe Gly Glu Leu
    210                 215                 220 gcg ggc agc atg tcg gtc atg tgc cac att ctc tgg aac gac ggc gac     720
Ala Gly Ser Met Ser Val Met Cys His Ile Leu Trp Asn Asp Gly Asp
225                 230                 235                 240 aac acg tac aag ggc aag ccg ctc ttc cgc gcg ggc atc atg cag ctg     768
Asn Thr Tyr Lys Gly Lys Pro Leu Phe Arg Ala Gly Ile Met Gln Leu
                245                 250                 255 ggg gcc atg gtg ccg ctg gac gcc gtg gac ggc atc tac ggc aac gag     816
Gly Ala Met Val Pro Leu Asp Ala Val Asp Gly Ile Tyr Gly Asn Glu
            260                 265                 270 atc ttt gac ctc ttg gcg tcg aac gcg ggc tgc ggc agc gcc agc gac     864
Ile Phe Asp Leu Leu Ala Ser Asn Ala Gly Cys Gly Ser Ala Ser Asp
        275                 280                 285 aag ctt gcg tgc ttg cgc ggt gtg ctg agc gac acg ttg gag gac gcc     912
Lys Leu Ala Cys Leu Arg Gly Val Leu Ser Asp Thr Leu Glu Asp Ala
    290                 295                 300
```

| | | |
|---|---|---|
| acc aac aac acc cct ggg ttc ttg gcg tac tcc tcg ttg cgg ttg ctg<br>Thr Asn Asn Thr Pro Gly Phe Leu Ala Tyr Ser Ser Leu Arg Leu Leu<br>305                  310                    315                320 | | 960 |
| tac ctc ccc cgg ccc gac ggc gtg aac atc acc gac gac atg tac gcc<br>Tyr Leu Pro Arg Pro Asp Gly Val Asn Ile Thr Asp Asp Met Tyr Ala<br>              325                    330                    335 | | 1008 |
| ttg gtg cgc gag ggc aag tat gcc aac atc cct gtg atc atc ggc gac<br>Leu Val Arg Glu Gly Lys Tyr Ala Asn Ile Pro Val Ile Ile Gly Asp<br>        340                    345                    350 | | 1056 |
| cag aac gac gag ggc acc ttc ttt ggc acc ctg ctg aac gtg acc<br>Gln Asn Asp Glu Gly Thr Phe Phe Gly Thr Leu Leu Asn Val Thr<br>355                  360                    365 | | 1104 |
| acg gat gcc cag gcc cgc gag tac ttc aag cag ctg ttt gtc cac gcc<br>Thr Asp Ala Gln Ala Arg Glu Tyr Phe Lys Gln Leu Phe Val His Ala<br>    370                    375                    380 | | 1152 |
| agc gac gcg gag atc gac acg ttg atg acg gcg tac ccc ggc gac atc<br>Ser Asp Ala Glu Ile Asp Thr Leu Met Thr Ala Tyr Pro Gly Asp Ile<br>385                  390                    395                400 | | 1200 |
| acc cag ggc ctg ccg ttc gac acg ggt att ctc aac gcc ctc acc ccg<br>Thr Gln Gly Leu Pro Phe Asp Thr Gly Ile Leu Asn Ala Leu Thr Pro<br>              405                    410                    415 | | 1248 |
| cag ttc aag aga atc ctg gcg gtg ctc ggc gac ctt ggc ttt acg ctt<br>Gln Phe Lys Arg Ile Leu Ala Val Leu Gly Asp Leu Gly Phe Thr Leu<br>        420                    425                    430 | | 1296 |
| gct cgt cgc tac ttc ctc aac cac tac acc ggc ggc acc aag tac tca<br>Ala Arg Arg Tyr Phe Leu Asn His Tyr Thr Gly Gly Thr Lys Tyr Ser<br>435                    440                    445 | | 1344 |
| ttc ctc ctg aag cag ctc ctg ggc ttg ccg gtg ctc gga acg ttc cac<br>Phe Leu Leu Lys Gln Leu Leu Gly Leu Pro Val Leu Gly Thr Phe His<br>    450                    455                    460 | | 1392 |
| tcc aac gac att gtc ttc cag gac tac ttg ttg ggc agc ggc tcg ctc<br>Ser Asn Asp Ile Val Phe Gln Asp Tyr Leu Leu Gly Ser Gly Ser Leu<br>465                  470                    475                480 | | 1440 |
| atc tac aac aac gcg ttc att gcg ttt gcc acg gac ttg gac ccc aac<br>Ile Tyr Asn Asn Ala Phe Ile Ala Phe Ala Thr Asp Leu Asp Pro Asn<br>              485                    490                    495 | | 1488 |
| acc gcg ggg ttg ttg gtg aag tgg ccc gag tac acc agc agc ctg cag<br>Thr Ala Gly Leu Leu Val Lys Trp Pro Glu Tyr Thr Ser Ser Leu Gln<br>        500                    505                    510 | | 1536 |
| ctg ggc aac aac ttg atg atg atc aac gcc ttg ggc ttg tac acc ggc<br>Leu Gly Asn Asn Leu Met Met Ile Asn Ala Leu Gly Leu Tyr Thr Gly<br>515                  520                    525 | | 1584 |
| aag gac aac ttc cgc acc gcc ggc tac gac gcg ttg ttc tcc aac ccg<br>Lys Asp Asn Phe Arg Thr Ala Gly Tyr Asp Ala Leu Phe Ser Asn Pro<br>    530                    535                    540 | | 1632 |
| ccg ctg ttc ttt gtg taa<br>Pro Leu Phe Phe Val<br>545 | | 1650 |

```
<210> SEQ ID NO 12
<211> LENGTH: 549
<212> TYPE: PRT
<213> ORGANISM: Candida rugosa

<400> SEQUENCE: 12
```

Met Glu Leu Ala Leu Ala Leu Leu Ile Ala Ser Val Ala Ala
1               5                     10                    15

Pro Thr Ala Thr Leu Ala Asn Gly Asp Thr Ile Thr Gly Leu Asn Ala
              20                    25                    30

Ile Ile Asn Glu Ala Phe Leu Gly Ile Pro Phe Ala Glu Pro Pro Val
        35                    40                    45

-continued

```
Gly Asn Leu Arg Phe Lys Asp Pro Val Pro Tyr Ser Gly Ser Leu Asp
     50                  55                  60

Gly Gln Lys Phe Thr Leu Tyr Gly Pro Leu Cys Met Gln Gln Asn Pro
 65                  70                  75                  80

Glu Gly Thr Tyr Glu Glu Asn Leu Pro Lys Ala Ala Leu Asp Leu Val
                 85                  90                  95

Met Gln Ser Lys Val Phe Glu Ala Val Leu Pro Leu Ser Glu Asp Cys
            100                 105                 110

Leu Thr Ile Asn Val Val Arg Pro Gly Thr Lys Ala Gly Ala Asn
        115                 120                 125

Leu Pro Val Met Leu Trp Ile Phe Gly Gly Phe Glu Val Gly Gly
    130                 135                 140

Thr Ser Thr Phe Pro Pro Ala Gln Met Ile Thr Lys Ser Ile Ala Met
145                 150                 155                 160

Gly Lys Pro Ile Ile His Val Ser Val Asn Tyr Arg Val Ser Ser Trp
                165                 170                 175

Gly Phe Leu Ala Gly Asp Glu Ile Lys Ala Glu Gly Ser Ala Asn Ala
            180                 185                 190

Gly Leu Lys Asp Gln Arg Leu Gly Met Gln Trp Val Ala Asp Asn Ile
        195                 200                 205

Ala Ala Phe Gly Gly Asp Pro Thr Lys Val Thr Ile Phe Gly Glu Leu
    210                 215                 220

Ala Gly Ser Met Ser Val Met Cys His Ile Leu Trp Asn Asp Gly Asp
225                 230                 235                 240

Asn Thr Tyr Lys Gly Lys Pro Leu Phe Arg Ala Gly Ile Met Gln Leu
                245                 250                 255

Gly Ala Met Val Pro Leu Asp Ala Val Asp Gly Ile Tyr Gly Asn Glu
            260                 265                 270

Ile Phe Asp Leu Leu Ala Ser Asn Ala Gly Cys Gly Ser Ala Ser Asp
        275                 280                 285

Lys Leu Ala Cys Leu Arg Gly Val Leu Ser Asp Thr Leu Glu Asp Ala
    290                 295                 300

Thr Asn Asn Thr Pro Gly Phe Leu Ala Tyr Ser Ser Leu Arg Leu Leu
305                 310                 315                 320

Tyr Leu Pro Arg Pro Asp Gly Val Asn Ile Thr Asp Asp Met Tyr Ala
                325                 330                 335

Leu Val Arg Glu Gly Lys Tyr Ala Asn Ile Pro Val Ile Ile Gly Asp
            340                 345                 350

Gln Asn Asp Glu Gly Thr Phe Phe Gly Thr Leu Leu Leu Asn Val Thr
        355                 360                 365

Thr Asp Ala Gln Ala Arg Glu Tyr Phe Lys Gln Leu Phe Val His Ala
    370                 375                 380

Ser Asp Ala Glu Ile Asp Thr Leu Met Thr Ala Tyr Pro Gly Asp Ile
385                 390                 395                 400

Thr Gln Gly Leu Pro Phe Asp Thr Gly Ile Leu Asn Ala Leu Thr Pro
                405                 410                 415

Gln Phe Lys Arg Ile Leu Ala Val Leu Gly Asp Leu Gly Phe Thr Leu
            420                 425                 430

Ala Arg Arg Tyr Phe Leu Asn His Tyr Thr Gly Gly Thr Lys Tyr Ser
        435                 440                 445

Phe Leu Leu Lys Gln Leu Leu Gly Leu Pro Val Leu Gly Thr Phe His
    450                 455                 460

Ser Asn Asp Ile Val Phe Gln Asp Tyr Leu Leu Gly Ser Gly Ser Leu
465                 470                 475                 480
```

```
Ile Tyr Asn Asn Ala Phe Ile Ala Phe Ala Thr Asp Leu Asp Pro Asn
            485                 490                 495
Thr Ala Gly Leu Leu Val Lys Trp Pro Glu Tyr Thr Ser Ser Leu Gln
        500                 505                 510
Leu Gly Asn Asn Leu Met Met Ile Asn Ala Leu Gly Leu Tyr Thr Gly
    515                 520                 525
Lys Asp Asn Phe Arg Thr Ala Gly Tyr Asp Ala Leu Phe Ser Asn Pro
530                 535                 540
Pro Leu Phe Phe Val
545

<210> SEQ ID NO 13
<211> LENGTH: 1647
<212> TYPE: DNA
<213> ORGANISM: Candida rugosa
<220> FEATURE:
<221> NAME/KEY: CDS
<222> LOCATION: (1)..(1647)

<400> SEQUENCE: 13
```

| | | | | | | | | | | | | | | | | |
|---|---|---|---|---|---|---|---|---|---|---|---|---|---|---|---|---|
| atg | aag | ctc | tgt | ttg | ctt | gct | ctt | ggt | gct | gcg | gtg | gcg | gca | gcc | ccc | 48 |
| Met | Lys | Leu | Cys | Leu | Leu | Ala | Leu | Gly | Ala | Ala | Val | Ala | Ala | Ala | Pro | |
| 1 | | | | 5 | | | | | 10 | | | | | 15 | | |
| acg | gcc | acc | ctc | gcc | aac | ggc | gac | acc | atc | acc | ggt | ctc | aac | gcc | att | 96 |
| Thr | Ala | Thr | Leu | Ala | Asn | Gly | Asp | Thr | Ile | Thr | Gly | Leu | Asn | Ala | Ile | |
| | | | 20 | | | | | 25 | | | | | 30 | | | |
| gtc | aac | gaa | aag | ttt | ctc | ggc | ata | ccg | ttt | gcc | gag | ccg | ccc | gtg | ggc | 144 |
| Val | Asn | Glu | Lys | Phe | Leu | Gly | Ile | Pro | Phe | Ala | Glu | Pro | Pro | Val | Gly | |
| | | 35 | | | | | 40 | | | | | 45 | | | | |
| acg | ctc | cgc | ttc | aag | ccg | ccc | gtg | ccg | tac | tcg | gcg | tcg | ctc | aac | ggc | 192 |
| Thr | Leu | Arg | Phe | Lys | Pro | Pro | Val | Pro | Tyr | Ser | Ala | Ser | Leu | Asn | Gly | |
| | 50 | | | | | 55 | | | | | 60 | | | | | |
| cag | cag | ttt | acc | ctg | tac | ggc | ccg | ctg | tgc | atg | cag | atg | aac | cct | atg | 240 |
| Gln | Gln | Phe | Thr | Leu | Tyr | Gly | Pro | Leu | Cys | Met | Gln | Met | Asn | Pro | Met | |
| 65 | | | | | 70 | | | | | 75 | | | | | 80 | |
| ggc | tcg | ttt | gag | gac | aca | ctt | ccc | aag | aat | gcg | cgg | cat | ttg | gtg | ctc | 288 |
| Gly | Ser | Phe | Glu | Asp | Thr | Leu | Pro | Lys | Asn | Ala | Arg | His | Leu | Val | Leu | |
| | | | | 85 | | | | | 90 | | | | | 95 | | |
| cag | tcc | aag | atc | ttc | caa | gtg | gtg | ctt | ccc | aac | gac | gag | gac | tgt | ctc | 336 |
| Gln | Ser | Lys | Ile | Phe | Gln | Val | Val | Leu | Pro | Asn | Asp | Glu | Asp | Cys | Leu | |
| | | | 100 | | | | | 105 | | | | | 110 | | | |
| acc | atc | aac | gtg | atc | cgg | ccg | ccc | ggc | acc | agg | gcc | agt | gct | ggt | ctc | 384 |
| Thr | Ile | Asn | Val | Ile | Arg | Pro | Pro | Gly | Thr | Arg | Ala | Ser | Ala | Gly | Leu | |
| | | 115 | | | | | 120 | | | | | 125 | | | | |
| ccg | gtg | atg | ctc | tgg | atc | ttt | ggc | ggt | ggg | ttt | gag | ctt | ggc | ggc | tcc | 432 |
| Pro | Val | Met | Leu | Trp | Ile | Phe | Gly | Gly | Gly | Phe | Glu | Leu | Gly | Gly | Ser | |
| | 130 | | | | | 135 | | | | | 140 | | | | | |
| agc | ctc | ttt | cca | gga | gac | cag | atg | gtg | gcc | aag | agc | gtg | ctc | atg | ggt | 480 |
| Ser | Leu | Phe | Pro | Gly | Asp | Gln | Met | Val | Ala | Lys | Ser | Val | Leu | Met | Gly | |
| 145 | | | | | 150 | | | | | 155 | | | | | 160 | |
| aaa | ccg | gtg | atc | cac | gtg | agc | atg | aac | tac | cgc | gtg | gcg | tca | tgg | ggg | 528 |
| Lys | Pro | Val | Ile | His | Val | Ser | Met | Asn | Tyr | Arg | Val | Ala | Ser | Trp | Gly | |
| | | | | 165 | | | | | 170 | | | | | 175 | | |
| ttc | ttg | gcc | ggc | ccc | gac | atc | cag | aac | gaa | ggc | agc | ggg | aac | gcc | ggc | 576 |
| Phe | Leu | Ala | Gly | Pro | Asp | Ile | Gln | Asn | Glu | Gly | Ser | Gly | Asn | Ala | Gly | |
| | | | 180 | | | | | 185 | | | | | 190 | | | |
| ttg | cat | gac | cag | cgc | ttg | gcc | atg | cag | tgg | gtg | gcg | gac | aac | att | gct | 624 |
| Leu | His | Asp | Gln | Arg | Leu | Ala | Met | Gln | Trp | Val | Ala | Asp | Asn | Ile | Ala | |
| | | 195 | | | | | 200 | | | | | 205 | | | | |

```
ggg ttt ggc ggc gac ccg agc aag gtg acc ata tac ggc gag ctg gcg      672
Gly Phe Gly Gly Asp Pro Ser Lys Val Thr Ile Tyr Gly Glu Leu Ala
210                 215                 220 ggc agc atg tcg acg ttt gtg cac ctt gtg tgg aac gac ggc gac aac      720
Gly Ser Met Ser Thr Phe Val His Leu Val Trp Asn Asp Gly Asp Asn
225                 230                 235                 240 acg tac aac ggc aag ccg ttg ttc cgc gcc gcc atc atg cag ctg ggc      768
Thr Tyr Asn Gly Lys Pro Leu Phe Arg Ala Ala Ile Met Gln Leu Gly
                245                 250                 255 tgc atg gtg ccg ctg gac ccg gtg gac ggc acg tac ggc acc gag atc      816
Cys Met Val Pro Leu Asp Pro Val Asp Gly Thr Tyr Gly Thr Glu Ile
            260                 265                 270 tac aac cag gtg gtg gcg tct gcc ggg tgt ggc agt gcc agc gac aag      864
Tyr Asn Gln Val Val Ala Ser Ala Gly Cys Gly Ser Ala Ser Asp Lys
        275                 280                 285 ctc gcg tgc ttg cgc ggc ctt ctg cag gac acg ttg tac cag gcc acg      912
Leu Ala Cys Leu Arg Gly Leu Leu Gln Asp Thr Leu Tyr Gln Ala Thr
    290                 295                 300 agc gac acg ccc ggc gtg ttg gcg tac ccg tcg ttg cgg ttg ctg tat      960
Ser Asp Thr Pro Gly Val Leu Ala Tyr Pro Ser Leu Arg Leu Leu Tyr
305                 310                 315                 320 ctc ccg cgg ccc gac ggc acc ttc atc acc gac gac atg tat gcc ttg     1008
Leu Pro Arg Pro Asp Gly Thr Phe Ile Thr Asp Asp Met Tyr Ala Leu
                325                 330                 335 gtg cgg gac ggc aag tac gca cac gtg ccg gtg atc atc ggc gac cag     1056
Val Arg Asp Gly Lys Tyr Ala His Val Pro Val Ile Ile Gly Asp Gln
            340                 345                 350 aac gac gag ggc act ttg ttt ggg ctc ctg ctg aac gtg acc aca         1104
Asn Asp Glu Gly Thr Leu Phe Gly Leu Leu Leu Asn Val Thr Thr
        355                 360                 365 gat gct cag gca cgg gcg tac ttc aag cag ctg ttc atc cac gcc agc     1152
Asp Ala Gln Ala Arg Ala Tyr Phe Lys Gln Leu Phe Ile His Ala Ser
    370                 375                 380 gat gcg gag atc gac acg ttg atg gcg gcg tac acc agc gac atc acc     1200
Asp Ala Glu Ile Asp Thr Leu Met Ala Ala Tyr Thr Ser Asp Ile Thr
385                 390                 395                 400 cag ggt ctg ccg ttc gac acc ggc atc ttc aat gcc atc acc ccg cag     1248
Gln Gly Leu Pro Phe Asp Thr Gly Ile Phe Asn Ala Ile Thr Pro Gln
                405                 410                 415 ttc aaa cgg atc ctg gcg ttg ctt ggc gac ctt gcg ttc acg ctt gcg     1296
Phe Lys Arg Ile Leu Ala Leu Leu Gly Asp Leu Ala Phe Thr Leu Ala
            420                 425                 430 cgt cgc tac ttc ctc aac tac tac cag ggc ggc acc aag tac tcg ttt     1344
Arg Arg Tyr Phe Leu Asn Tyr Tyr Gln Gly Gly Thr Lys Tyr Ser Phe
        435                 440                 445 ctc ctg aag cag ctt ctg ggg ttg ccc gtc ttg ggc acc ttc cac ggc     1392
Leu Leu Lys Gln Leu Leu Gly Leu Pro Val Leu Gly Thr Phe His Gly
    450                 455                 460 aac gac atc atc tgg cag gac tac ttg gtg ggc agc ggc agt gtg atc     1440
Asn Asp Ile Ile Trp Gln Asp Tyr Leu Val Gly Ser Gly Ser Val Ile
465                 470                 475                 480 tac aac aac gcg ttc att gcg ttt gcc aac gac ctc gac ccg aac aag     1488
Tyr Asn Asn Ala Phe Ile Ala Phe Ala Asn Asp Leu Asp Pro Asn Lys
                485                 490                 495 gcg ggc ttg tgg acc aac tgg ccc acg tac acc agc agt ctg cag ctg     1536
Ala Gly Leu Trp Thr Asn Trp Pro Thr Tyr Thr Ser Ser Leu Gln Leu
            500                 505                 510 ggc aac aac ttg atg cag atc aac ggc ttg ggg ttg tac acc ggc aag     1584
Gly Asn Asn Leu Met Gln Ile Asn Gly Leu Gly Leu Tyr Thr Gly Lys
        515                 520                 525
```

```
gac aac ttc cgc ccg gat gcg tac agc gcc ctc ttt tcc aac ccg cca    1632
Asp Asn Phe Arg Pro Asp Ala Tyr Ser Ala Leu Phe Ser Asn Pro Pro
            530                 535                 540 ctg ttc ttt gtg tag                                                 1647
Leu Phe Phe Val
545
```

<210> SEQ ID NO 14
<211> LENGTH: 548
<212> TYPE: PRT
<213> ORGANISM: Candida rugosa

<400> SEQUENCE: 14

```
Met Lys Leu Cys Leu Leu Ala Leu Gly Ala Ala Val Ala Ala Ala Pro
1               5                   10                  15

Thr Ala Thr Leu Ala Asn Gly Asp Thr Ile Thr Gly Leu Asn Ala Ile
                20                  25                  30

Val Asn Glu Lys Phe Leu Gly Ile Pro Phe Ala Glu Pro Pro Val Gly
            35                  40                  45

Thr Leu Arg Phe Lys Pro Pro Val Pro Tyr Ser Ala Ser Leu Asn Gly
        50                  55                  60

Gln Gln Phe Thr Leu Tyr Gly Pro Leu Cys Met Gln Met Asn Pro Met
65                  70                  75                  80

Gly Ser Phe Glu Asp Thr Leu Pro Lys Asn Ala Arg His Leu Val Leu
                85                  90                  95

Gln Ser Lys Ile Phe Gln Val Val Leu Pro Asn Asp Glu Asp Cys Leu
            100                 105                 110

Thr Ile Asn Val Ile Arg Pro Pro Gly Thr Arg Ala Ser Ala Gly Leu
        115                 120                 125

Pro Val Met Leu Trp Ile Phe Gly Gly Gly Phe Glu Leu Gly Gly Ser
130                 135                 140

Ser Leu Phe Pro Gly Asp Gln Met Val Ala Lys Ser Val Leu Met Gly
145                 150                 155                 160

Lys Pro Val Ile His Val Ser Met Asn Tyr Arg Val Ala Ser Trp Gly
                165                 170                 175

Phe Leu Ala Gly Pro Asp Ile Gln Asn Glu Gly Ser Gly Asn Ala Gly
            180                 185                 190

Leu His Asp Gln Arg Leu Ala Met Gln Trp Val Ala Asp Asn Ile Ala
        195                 200                 205

Gly Phe Gly Gly Asp Pro Ser Lys Val Thr Ile Tyr Gly Glu Leu Ala
210                 215                 220

Gly Ser Met Ser Thr Phe Val His Leu Val Trp Asn Asp Gly Asp Asn
225                 230                 235                 240

Thr Tyr Asn Gly Lys Pro Leu Phe Arg Ala Ala Ile Met Gln Leu Gly
                245                 250                 255

Cys Met Val Pro Leu Asp Pro Val Asp Gly Thr Tyr Gly Thr Glu Ile
            260                 265                 270

Tyr Asn Gln Val Val Ala Ser Ala Gly Cys Gly Ser Ala Ser Asp Lys
        275                 280                 285

Leu Ala Cys Leu Arg Gly Leu Leu Gln Asp Thr Leu Tyr Gln Ala Thr
290                 295                 300

Ser Asp Thr Pro Gly Val Leu Ala Tyr Pro Ser Leu Arg Leu Leu Tyr
305                 310                 315                 320

Leu Pro Arg Pro Asp Gly Thr Phe Ile Thr Asp Asp Met Tyr Ala Leu
                325                 330                 335
```

-continued

```
Val Arg Asp Gly Lys Tyr Ala His Val Pro Val Ile Ile Gly Asp Gln
            340                 345                 350

Asn Asp Glu Gly Thr Leu Phe Gly Leu Leu Leu Asn Val Thr Thr
            355                 360                 365

Asp Ala Gln Ala Arg Ala Tyr Phe Lys Gln Leu Phe Ile His Ala Ser
370                 375                 380

Asp Ala Glu Ile Asp Thr Leu Met Ala Ala Tyr Thr Ser Asp Ile Thr
385                 390                 395                 400

Gln Gly Leu Pro Phe Asp Thr Gly Ile Phe Asn Ala Ile Thr Pro Gln
                405                 410                 415

Phe Lys Arg Ile Leu Ala Leu Leu Gly Asp Leu Ala Phe Thr Leu Ala
            420                 425                 430

Arg Arg Tyr Phe Leu Asn Tyr Tyr Gln Gly Gly Thr Lys Tyr Ser Phe
        435                 440                 445

Leu Leu Lys Gln Leu Leu Gly Leu Pro Val Leu Gly Thr Phe His Gly
            450                 455                 460

Asn Asp Ile Ile Trp Gln Asp Tyr Leu Val Gly Ser Gly Ser Val Ile
465                 470                 475                 480

Tyr Asn Asn Ala Phe Ile Ala Phe Ala Asn Asp Leu Asp Pro Asn Lys
                485                 490                 495

Ala Gly Leu Trp Thr Asn Trp Pro Thr Tyr Thr Ser Ser Leu Gln Leu
            500                 505                 510

Gly Asn Asn Leu Met Gln Ile Asn Gly Leu Gly Leu Tyr Thr Gly Lys
        515                 520                 525

Asp Asn Phe Arg Pro Asp Ala Tyr Ser Ala Leu Phe Ser Asn Pro Pro
            530                 535                 540

Leu Phe Phe Val
545

<210> SEQ ID NO 15
<211> LENGTH: 720
<212> TYPE: DNA
<213> ORGANISM: Escherichia coli
<220> FEATURE:
<221> NAME/KEY: CDS
<222> LOCATION: (1)..(717)

<400> SEQUENCE: 15 atg gtc att aag gcg caa agc ccg gcg ggt ttc gcg gaa gag tac att      48
Met Val Ile Lys Ala Gln Ser Pro Ala Gly Phe Ala Glu Glu Tyr Ile
1               5                   10                  15 att gaa agt atc tgg aat aac cgc ttc cct ccc ggg act att ttg ccc      96
Ile Glu Ser Ile Trp Asn Asn Arg Phe Pro Pro Gly Thr Ile Leu Pro
            20                  25                  30 gca gaa cgt gaa ctt tca gaa tta att ggc gta acg cgt act acg tta    144
Ala Glu Arg Glu Leu Ser Glu Leu Ile Gly Val Thr Arg Thr Thr Leu
        35                  40                  45 cgt gaa gtg tta cag cgt ctg gca cga gat ggc tgg ttg acc att caa    192
Arg Glu Val Leu Gln Arg Leu Ala Arg Asp Gly Trp Leu Thr Ile Gln
    50                  55                  60 cat ggc aag ccg acg aag gtg aat aat ttc tgg gaa act tcc ggt tta    240
His Gly Lys Pro Thr Lys Val Asn Asn Phe Trp Glu Thr Ser Gly Leu
65                  70                  75                  80 aat atc ctt gaa aca ctg gcg cga ctg gat cac gaa agt gtg ccg cag    288
Asn Ile Leu Glu Thr Leu Ala Arg Leu Asp His Glu Ser Val Pro Gln
                85                  90                  95 ctt att gat aat ttg ctg tcg gtg cgt acc aat att tcc act att ttt    336
Leu Ile Asp Asn Leu Leu Ser Val Arg Thr Asn Ile Ser Thr Ile Phe
            100                 105                 110
```

```
att cgc acc gcg ttt cgt cag cat ccc gat aaa gcg cag gaa gtg ctg        384
Ile Arg Thr Ala Phe Arg Gln His Pro Asp Lys Ala Gln Glu Val Leu
        115                 120                 125 gct acc gct aat gaa gtg gcc gat cac gcc gat gcc ttt gcc gag ctg        432
Ala Thr Ala Asn Glu Val Ala Asp His Ala Asp Ala Phe Ala Glu Leu
    130                 135                 140 gat tac aac ata ttc cgc ggc ctg gcg ttt gct tcc ggc aac ccg att        480
Asp Tyr Asn Ile Phe Arg Gly Leu Ala Phe Ala Ser Gly Asn Pro Ile
145                 150                 155                 160 tac ggt ctg att ctt aac ggg atg aaa ggg ctg tat acg cgt att ggt        528
Tyr Gly Leu Ile Leu Asn Gly Met Lys Gly Leu Tyr Thr Arg Ile Gly
                165                 170                 175 cgt cac tat ttc gcc aat ccg gaa gcg cgc agt ctg gcg ctg ggc ttc        576
Arg His Tyr Phe Ala Asn Pro Glu Ala Arg Ser Leu Ala Leu Gly Phe
            180                 185                 190 tac cac aaa ctg tcg gcg ttg tgc agt gaa ggc gcg cac gat cag gtg        624
Tyr His Lys Leu Ser Ala Leu Cys Ser Glu Gly Ala His Asp Gln Val
        195                 200                 205 tac gaa aca gtg cgt cgc tat ggg cat gag agt ggc gag att tgg cac        672
Tyr Glu Thr Val Arg Arg Tyr Gly His Glu Ser Gly Glu Ile Trp His
    210                 215                 220 cgg atg cag aaa aat ctg ccg ggt gat tta gcc att cag ggg cga taa       720
Arg Met Gln Lys Asn Leu Pro Gly Asp Leu Ala Ile Gln Gly Arg
225                 230                 235

<210> SEQ ID NO 16
<211> LENGTH: 63
<212> TYPE: DNA
<213> ORGANISM: Artificial Sequence
<220> FEATURE:
<223> OTHER INFORMATION: Primer for fadR amplification

<400> SEQUENCE: 16
tatgatgagt ccaactttgt tttgctgtgt tatggaaatc tcacttgaag cctgcttttt      60
tat                                                                   63

<210> SEQ ID NO 17
<211> LENGTH: 63
<212> TYPE: DNA
<213> ORGANISM: Artificial Sequence
<220> FEATURE:
<223> OTHER INFORMATION: Primer for fadR amplification

<400> SEQUENCE: 17 caaaaaccc ctcgtttgag gggtttgctc tttaaacgga agggacgctc aagttagtat      60
aaa                                                                   63
```